US012201379B2

(12) United States Patent
Greenwood et al.

(10) Patent No.: US 12,201,379 B2
(45) Date of Patent: Jan. 21, 2025

(54) X-WING ENHANCED GUIDANCE SYSTEM FOR DISTAL TARGETING

(71) Applicant: DePuy Synthes Products, Inc., Raynham, MA (US)

(72) Inventors: Megan Greenwood, Houston, TX (US); William E. Cohn, Bellaire, TX (US); Jorge Salazar, Houston, TX (US); Emir Kamaric, Houston, TX (US); Nicolo Garbin, Houston, TX (US); Abdul Umaru, Houston, TX (US); Scott Sloss, Katy, TX (US)

(73) Assignee: DePuy Synthes Products, Inc., Raynham, MA (US)

( * ) Notice: Subject to any disclaimer, the term of this patent is extended or adjusted under 35 U.S.C. 154(b) by 371 days.

(21) Appl. No.: 17/679,580

(22) Filed: Feb. 24, 2022

(65) Prior Publication Data
US 2023/0218348 A1 Jul. 13, 2023

Related U.S. Application Data

(60) Provisional application No. 63/298,996, filed on Jan. 12, 2022.

(51) Int. Cl.
*A61B 34/20* (2016.01)
*A61B 17/16* (2006.01)
(Continued)

(52) U.S. Cl.
CPC .......... *A61B 34/20* (2016.02); *A61B 17/1615* (2013.01); *A61B 17/164* (2013.01);
(Continued)

(58) Field of Classification Search
CPC . A61B 34/20; A61B 17/16155; A61B 17/164; A61B 17/72; A61B 34/10;
(Continued)

(56) References Cited

U.S. PATENT DOCUMENTS

| 6,221,007 B1 | 4/2001 | Green |
| 6,697,664 B2 | 2/2004 | Kienzle et al. |

(Continued)

FOREIGN PATENT DOCUMENTS

| CN | 113349929 A | 9/2021 |
| DE | 102008023760 A1 | 12/2009 |

(Continued)

OTHER PUBLICATIONS

Hosseinian et al, Toward an End-to-End Calibration for Mobile C-Arm in Combination with a Depth Sensor for Surgical Augmented Reality Applications, Sensors (Basel), 2019;20(I):36, published Dec. 2019, 16 pages.

(Continued)

*Primary Examiner* — Joseph M Santos Rodriguez
*Assistant Examiner* — Amy Shafqat
(74) *Attorney, Agent, or Firm* — BakerHostetler

(57) ABSTRACT

A surgical instrument assembly configured to display a representation of the surgical instrument relative to a trajectory (e.g., a desired trajectory for drilling into an implant) based image data from an image sensor (e.g., a camera). For example, the surgical instrument assembly may be configured to determine a desired trajectory (e.g., a central axis of a distal hole of an intramedullary nail) based on X-ray image data representing at least one fiducial marker (e.g., an array of ArUco markers) and representing an anatomical structure and/or an implant. The surgical instrument assembly may in real time display a representation of the orientation and/or position of the surgical instrument (e.g., the orientation and position of a drill bit of the surgical instrument) in relation to the desired trajectory based on image sensor data that is generated based on an orientation of the at least one fiducial marker detected by an image sensor.

20 Claims, 28 Drawing Sheets

(51) Int. Cl.
*A61B 17/72* (2006.01)
*A61B 34/10* (2016.01)
*A61B 90/00* (2016.01)

(52) U.S. Cl.
CPC .............. *A61B 17/72* (2013.01); *A61B 34/10* (2016.02); *A61B 90/37* (2016.02); *A61B 90/39* (2016.02); *A61B 2034/102* (2016.02); *A61B 2034/105* (2016.02); *A61B 2034/2057* (2016.02); *A61B 2090/363* (2016.02); *A61B 2090/372* (2016.02); *A61B 2090/3937* (2016.02)

(58) Field of Classification Search
CPC ... A61B 90/37; A61B 90/39; A61B 2034/102; A61B 2034/105; A61B 2034/2057; A61B 2090/363; A61B 2090/372; A61B 2090/3937; A61B 2090/062; A61B 17/1622; A61B 2034/2065; A61B 2034/252; A61B 17/1703; A61B 17/1725; A61B 2034/107; A61B 2034/2048; A61B 2090/376; A61B 2090/3966; A61B 2090/3983
See application file for complete search history.

(56) References Cited

U.S. PATENT DOCUMENTS

| | | | |
|---|---|---|---|
| 8,118,818 | B2 | 2/2012 | Zheng et al. |
| 8,332,012 | B2 | 12/2012 | Kienzle, III |
| 8,382,759 | B2 | 2/2013 | Tuma et al. |
| 8,444,645 | B2 | 5/2013 | Zheng et al. |
| 8,560,047 | B2 | 10/2013 | Haider et al. |
| 9,782,183 | B1 | 10/2017 | Rich |
| 10,499,996 | B2 | 12/2019 | de Almeida Barreto |
| 10,736,644 | B2 | 8/2020 | Windolf et al. |
| 11,071,596 | B2 | 7/2021 | Ryan et al. |
| 11,116,574 | B2 | 9/2021 | Haider et al. |
| 2005/0020909 | A1 | 1/2005 | Moctezuma et al. |
| 2007/0274584 | A1 | 11/2007 | Leow et al. |
| 2013/0281884 | A1 | 10/2013 | Mullaney et al. |
| 2014/0148808 | A1* | 5/2014 | Inkpen .................. A61B 90/06 73/866.5 |
| 2018/0049622 | A1 | 2/2018 | Ryan et al. |
| 2019/0298451 | A1* | 10/2019 | Wong ...................... A61B 1/05 |
| 2019/0328466 | A1 | 10/2019 | Schwägli et al. |
| 2020/0188058 | A1 | 6/2020 | Mata |
| 2020/0275988 | A1 | 9/2020 | Johnson et al. |
| 2021/0038178 | A1 | 2/2021 | Mata et al. |
| 2021/0077194 | A1 | 3/2021 | Wahl et al. |
| 2021/0228220 | A1 | 7/2021 | Bettenga |
| 2022/0015835 | A1 | 1/2022 | Behera et al. |
| 2024/0041558 | A1* | 2/2024 | Siewerdsen ............ A61B 90/94 |

FOREIGN PATENT DOCUMENTS

| | | |
|---|---|---|
| JP | 6372784 B2 | 8/2018 |
| WO | 2020/160120 A1 | 8/2020 |

OTHER PUBLICATIONS

Sheth et al., Pre-clinical evaluation of a video-based drill guidance system for orthopaedic trauma surgery, Proc. SPIE 11598, Medical Imaging 2021: Image-Guided Procedures, Robotic Interventions, and Modeling, 1159806, Feb. 17, 2021, 8 pages.

Vagdargi et al., Drill-mounted video guidance for orthopaedic trauma surgery, Journal of Medical Imaging, vol. 8(1), 015002-1, Jan./Feb. 2021, 21 pages.

Vagdargi, Calibration and registration of a freehand video-guided surgical drill for orthopaedic trauma, Proc. SPIE 11315, Medical Imaging 2020: Image-Guided Procedures, Robotic Interventions, and Modeling, 113150G, Mar. 16, 2020, 8 pages.

Zhang, A Flexible New Technique for Camera Calibration, Pattern Analysis and Machine Intelligence, IEEE Transactions, vol. 22, No. 11, 1330-1334, Nov. 2000.

* cited by examiner

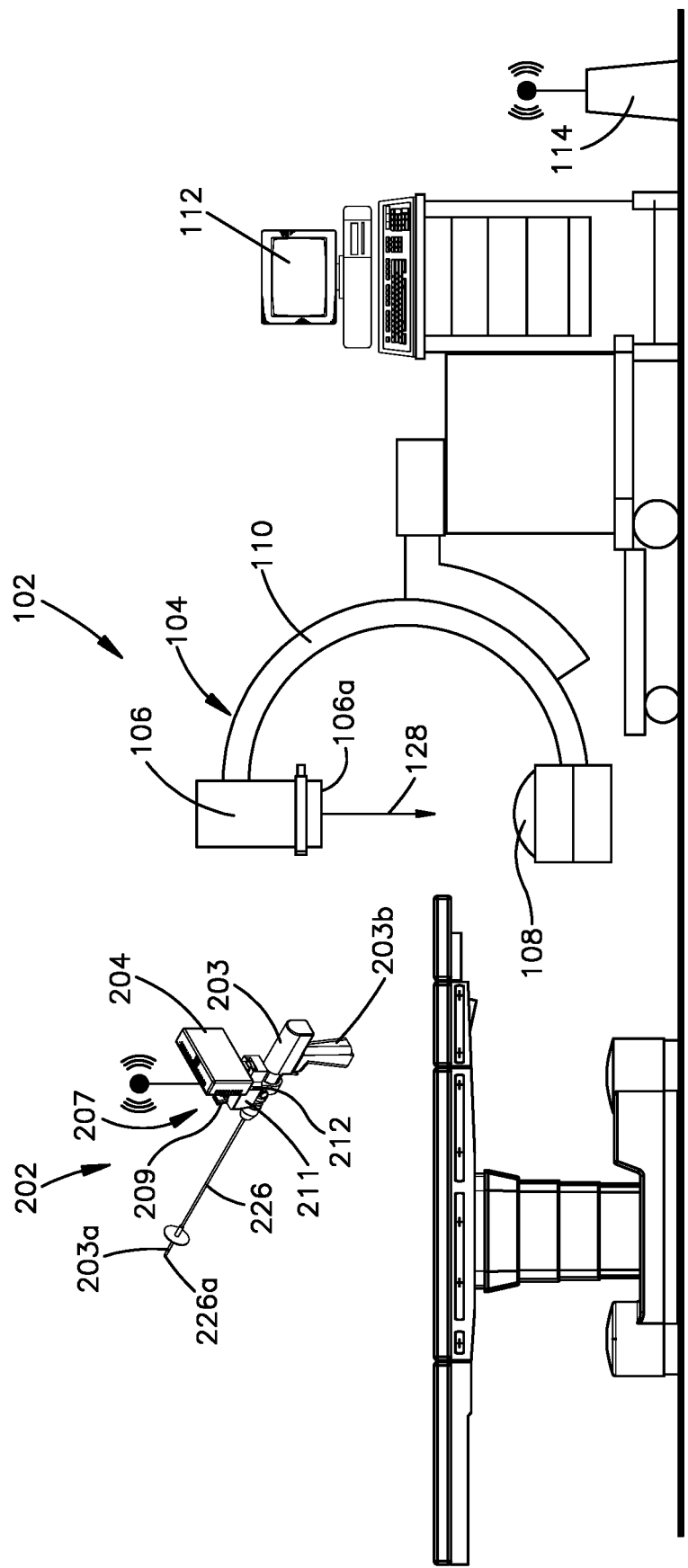

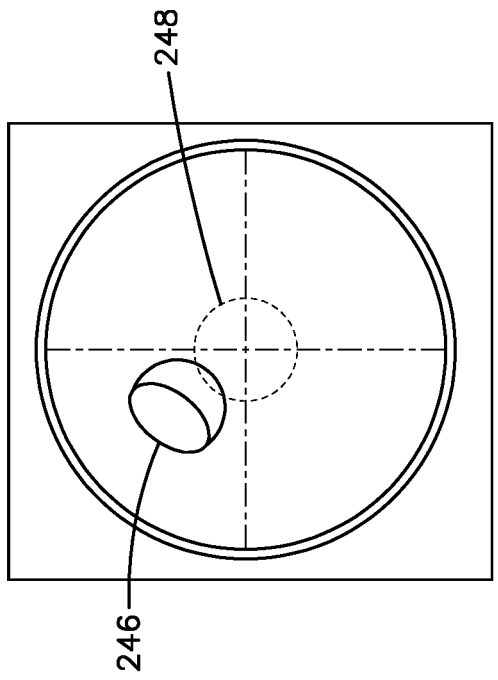
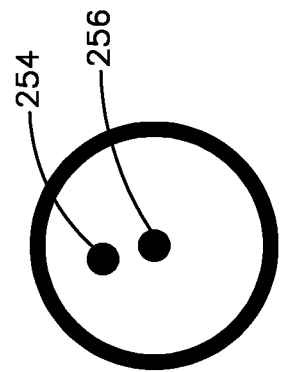
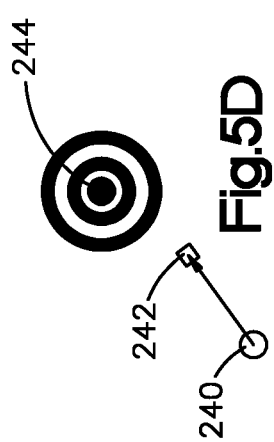
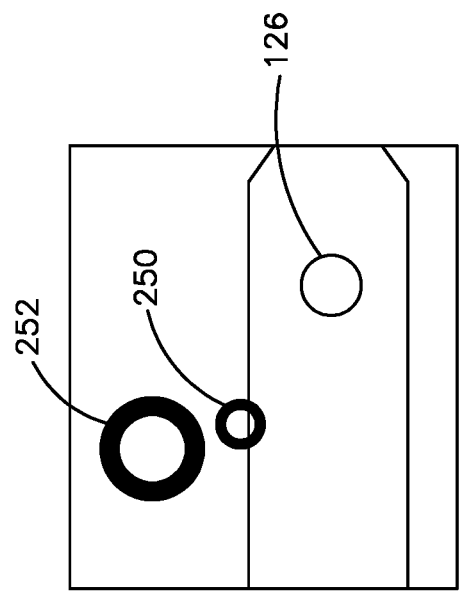

X-WING ENHANCED GUIDANCE SYSTEM FOR DISTAL TARGETING

CROSS-REFERENCE TO RELATED APPLICATIONS

This Application claims the benefit of U.S. Provisional Application Ser. No. 63/298,996 filed Jan. 12, 2022, the contents of which is hereby incorporated by reference as if set forth in its entirety herein.

JOINT RESEARCH AGREEMENT

The present disclosure was made by or on behalf of the below listed parties to a joint research agreement. The joint research agreement was in effect on or before the date the present disclosure was made and the present disclosure was made as a result of activities undertaken within the scope of the joint research agreement. The parties to the joint research agreement are 1) Depuy Synthes Products, Inc. and 2) HCL Technologies Limited.

TECHNICAL FIELD

The present invention relates to systems for targeting, particularly to guidance systems for distal targeting of an intramedullary nail, and related methods.

BACKGROUND

Various medical imaging devices, such as a C-arm device, can perform fluoroscopy, which is a type of medical imaging that shows a continuous X-ray image on a monitor. During a fluoroscopy procedure, the X-ray source or transmitter emits X-rays that penetrate a patient's body. The X-ray detector or image intensifier converts the X-rays that pass through the body into a visible image that is displayed on a monitor of the medical imaging device. Because such medical imaging devices can display high-resolution X-ray images in real time, a physician can monitor progress at any time during an operation, and thus can take appropriate actions based on the displayed images.

Monitoring the images, however, is often challenging during certain procedures, for instance during procedures in which attention must be paid to the patient's anatomy as well as the display of the medical imaging device. For example, aligning a drill bit to a distal locking hole can be difficult if a medical professional is required to maneuver the drill while viewing the display of the medical imaging device. Additionally, monitoring a procedure with medical imaging devices that emit X-rays can increasingly expose a patient to X-ray radiation.

SUMMARY

The present application provides for a surgical instrument assembly configured to display a representation of the surgical instrument relative to a trajectory (e.g., a desired trajectory for drilling into an implant) based image data from an image sensor (e.g., a camera). For example, the surgical instrument assembly may be configured to determine a desired trajectory (e.g., a central axis of a distal hole of an intramedullary nail) based on X-ray image data representing at least one fiducial marker (e.g., an array of ArUco markers) and representing an anatomical structure and/or an implant. The surgical instrument assembly may in real time display a representation of the orientation and/or position of the surgical instrument (e.g., the orientation and position of a drill bit of the surgical instrument) in relation to the desired trajectory based on image sensor data that is generated based on an orientation of the at least one fiducial marker detected by an image sensor.

For example, a single X-ray image of a target area of a patient's internal anatomy and the at least one fiducial marker—external to the patient such that the fiducial marker is detectable by the image sensor—may be generated. The desired trajectory relative to the target area and the at least one fiducial marker may be determined based X-ray image data representing the single X-ray image. The image sensor (e.g., a camera) may be configured to detect the orientation of the at least one fiducial marker relative to the image sensor. A display of the surgical instrument assembly may be configured to display in real time a representation of the orientation and/or position of the surgical instrument (e.g., a drill bit of the surgical instrument) relative to the desired trajectory based on real time image sensor data from the image sensor.

For example, memory of the surgical instrument assembly may determine and store an orientation and position of the drill bit relative to the image sensor. The memory may be configured to instruct a processor of the surgical instrument assembly to determine and store the desired trajectory relative to the target area and the at least one fiducial marker based the X-ray image data representing the single X-ray image. The memory may be configured to instruct the processor to determine in real time the orientation and/or position of the drill bit relative to the desired trajectory based on the image sensor data and the stored orientation of the of the drill bit relative to the image sensor. The memory may be configured to instruct the processor to output, to the display in real time, the representation of the orientation and/or position of the drill bit relative to the desired trajectory.

A single X-ray image may be sufficient to generate the X-ray image data. Thus, a second X-ray image, may not be necessary before surgery is completed. The surgical instrument assembly, thus, may provide for a reduction in the patient's exposure to X-rays compared to alternatives in which the patient is continually exposed to X-rays (e.g., during a fluoroscopic procedure).

In some embodiments, a second X-ray image may be taken to confirm the orientation and/or position of the surgical instrument. In such embodiments, a third X-ray image may not be necessary.

The trajectory may define a point of entry and the surgical instrument may display a representation of the position of a tip of the drill bit relative to the point of entry.

In an embodiment, the display is configured to display a representation of the drill bit tip and a point along a shaft of the drill bit. Each point may be represented by, for example, circles such that when the drill bit is aligned with the desired trajectory on a navigation display, the circles appear to be concentric circles.

The display may show a navigation target representing the center of a perfect circle and may show, for example, X-coordinates and Y-coordinates of the drill bit tip relative to the X-coordinates and Y-coordinates of the navigation target. When the drill bit tip is located at the center of the target, the circle representing the drill bit tip may be centered at the navigation target.

A navigation graphic displayed by the display may provide visual indicators to let the user know when the drill is acceptably oriented and/or positioned. For example, when the drill bit tip is located within a predetermined distance from the target center, the center of the target may change. When both the drill bit tip and the alignment of the drill bit axis are within a predetermined range, the outline of the display may change color.

During the actual drilling activity, the drill or camera may experience significant vibrations or deflections that cause noise in the navigational output. The memory may store instructions for the processor to reduce the impact of such noise. For example, the memory may store instructions for smoothing algorithms, such as a running average, for the drill bit position relative to the image sensor.

In some embodiments, the navigation graphic may switch from a detailed view (in which a representation of the drill tip and its axis are displayed) to a simple view in which an indication of whether the drill bit is aligned or not aligned is displayed. The memory may store instructions for the processor to automatically switch between the detailed view and the simple view based on whether drilling and/or a predetermined amount of vibrational movements of the camera is detected. Moreover, the memory may store predetermined thresholds for determining whether the drill bit is aligned or not aligned, and such predetermined thresholds may be based on expected noise due to drilling.

According to an embodiment of the present disclosure, A surgical instrument assembly comprises a surgical instrument configured to operate on an anatomical structure. An image sensor that is attached to the surgical instrument, wherein the image sensor is configured to detect an orientation of at least one fiducial marker relative to the image sensor, and the image sensor is configured to generate image sensor data that is based on the orientation of the at least one fiducial marker detected by the image sensor. The surgical instrument assembly includes a processor and a memory. The memory is in communication with the processor, the memory having stored therein instructions that, upon execution of the processor, cause the processor to 1) receive X-ray image data representing the at least one fiducial marker and representation an anatomical structure and/or an implant, 2) determine, based on the X-ray image data, a trajectory, relative to the at least one fiducial marker and relative to the anatomical structure and/or the implant, wherein the trajectory extends toward the anatomical structure and/or the implant, and 3) determine an orientation of the surgical instrument relative to the trajectory based on the image sensor data. The surgical instrument assembly includes a display coupled to the processor. The display is configured to display a representation of the orientation of the surgical instrument relative to the trajectory.

According to another embodiment of the present disclosure, a method of displaying an orientation of a surgical instrument comprises receiving an X-ray image data representing at least one fiducial marker and representing an anatomical structure and/or an implant. The method comprises determining, based on the X-ray image data, a trajectory, relative to the at least one fiducial marker, that extends toward the anatomical structure and/or the implant. The method comprises generating image sensor data, with an image sensor, that is based on an orientation of the at least one fiducial marker relative to the image sensor. The method comprises determining an orientation of the surgical instrument relative to the trajectory based upon the image sensor data. The method comprises displaying, with a display, a representation of the orientation of the surgical instrument relative to the trajectory.

BRIEF DESCRIPTION OF THE DRAWINGS

The foregoing summary, as well as the following detailed description of illustrative embodiments of the surgical instrument assembly of the present application, will be better understood when read in conjunction with the appended drawings. For the purposes of illustrating the expandable intervertebral implant of the present application, there is shown in the drawings illustrative embodiments. It should be understood, however, that the application is not limited to the precise arrangements and instrumentalities shown. In the drawings:

FIG. 1 depicts an example imaging system in accordance with an example embodiment, wherein the example imaging system includes an imaging device in electrical communication with a surgical instrument assembly.

FIG. 5D depicts an example screen shot of the display of the surgical instrument assembly, showing a circle and arrow visual indication of an alignment of the cutting instrument with respect to the desired drilling trajectory, wherein the cutting instrument is out of alignment.

FIG. 5E depicts an example screen shot of the display of the surgical instrument assembly, showing a bubble level visual indication of an alignment of the cutting instrument with respect to the desired drilling trajectory, wherein the cutting instrument is out of alignment.

FIG. 5F depicts an example screen shot of the display of the surgical instrument assembly, showing a pair of circles to visually indicate alignment of the cutting instrument with respect to the desired drilling trajectory, wherein the cutting instrument is out of alignment.

FIG. 5G depicts an example screen shot of the display of the surgical instrument assembly, showing dot and a movable dot that visually indicates alignment of the cutting instrument with respect to the desired drilling trajectory, wherein the cutting instrument is out of alignment.

DETAILED DESCRIPTION OF ILLUSTRATIVE EMBODIMENTS

Figure 2A:
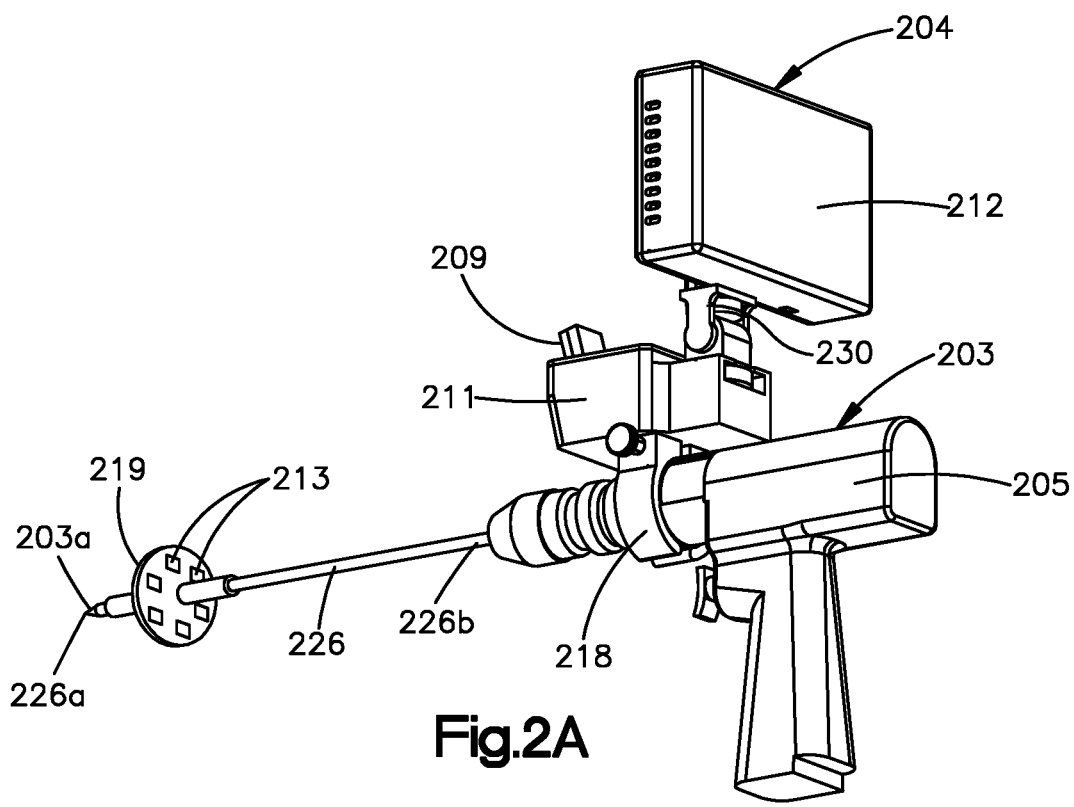
FIG. 2A is a rear perspective view of the surgical instrument assembly of FIG. 1, which includes a display attached to a surgical instrument.
Figure 2B:
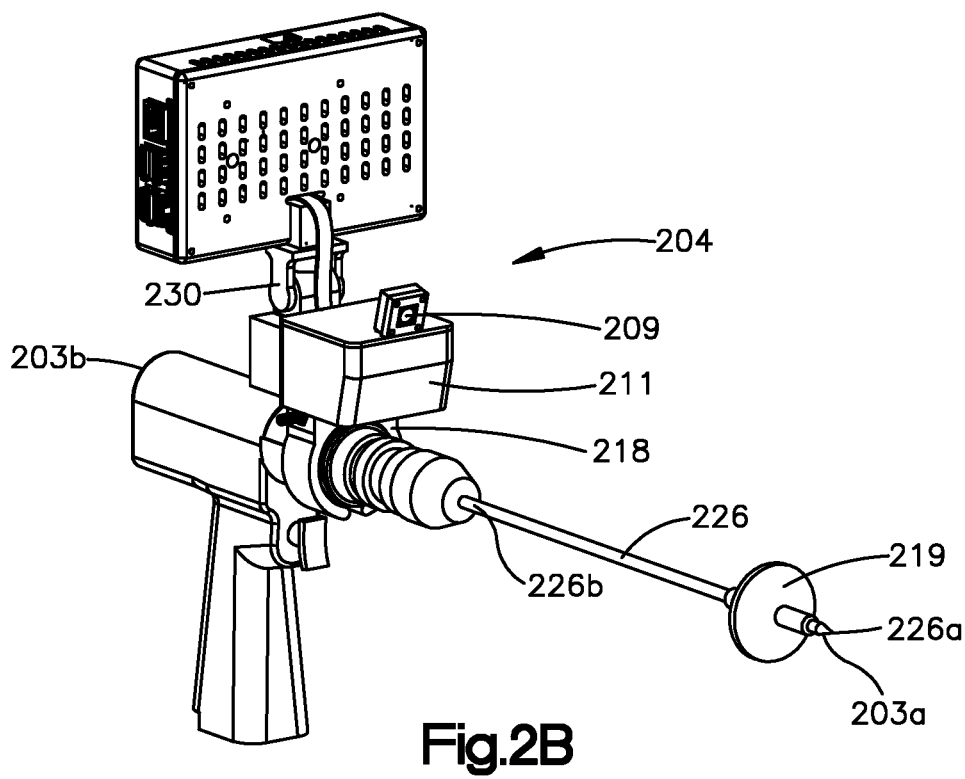
FIG. 2B is a front perspective view of the surgical instrument assembly of in FIG. 1.
Figure 2C:
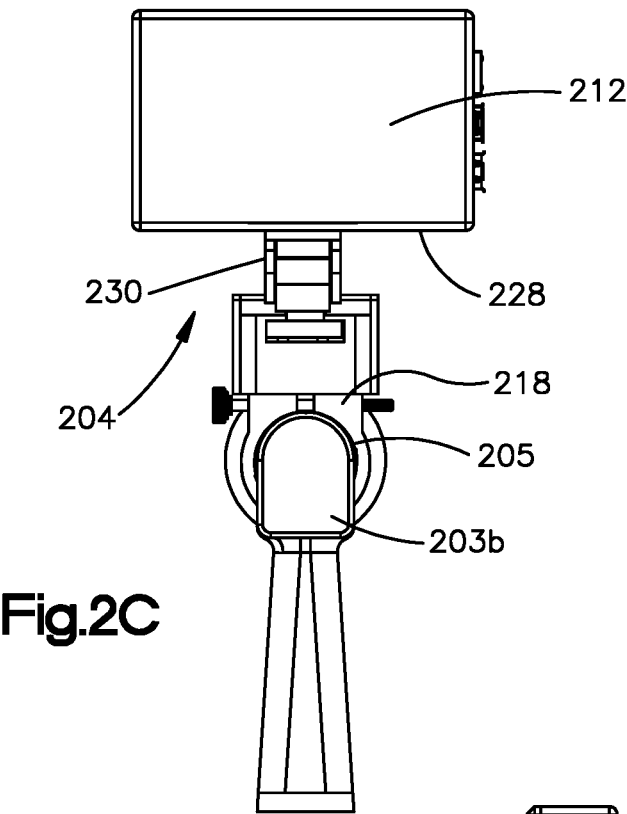
FIG. 2C is a rear elevation view of the surgical instrument assembly of FIG. 1.
Figure 2D:
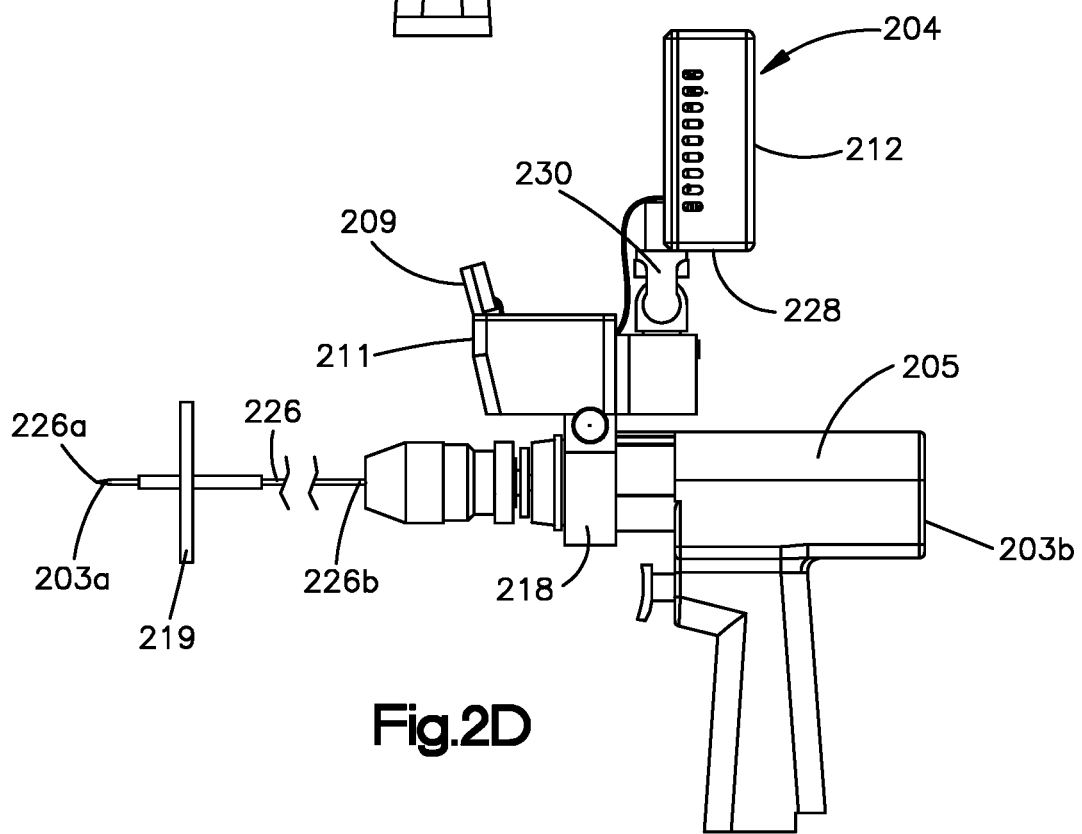
FIG. 2D is a side elevation view of the surgical instrument assembly of FIG. 1.

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a," "an," and "the" include the plural, and reference to a particular numerical value includes at least that particular value, unless the context clearly dictates otherwise.

The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

A medical professional can use a medical imaging device, for instance a C-arm device, to perform various medical procedures on a patient. For example, medical professionals can use imaging devices to assess bone fractures, guide surgical procedures, or verify results of surgical repairs. C-arm devices, for example, provide spot imaging and fluoroscopic imaging, which allows the generation of continuous real-time moving images. Such images may be provided to a display of the C-arm device.

It is recognized herein that, in some cases, the display of the C-arm system is not positioned in a manner that adequately assists a medical professional during surgery. In various embodiments described herein, images provided by imaging devices may be transmitted in real-time prior to the start of surgery to a display that can be mounted to a surgical instrument, such that fluoroscopic imaging provided by the imaging device can be processed in combination with image sensor data so that alignment of the surgical instrument is based on such image sensor data, as discussed further below.

The display can receive images in real-time, such that the images are displayed by the display in real time (e.g., at the same time that the images are generated by the imaging device). Displaying in real time includes updating the displayed image at least every 0.2 seconds. For example, the display may be updated with the current image every 0.001 to 0.2 seconds. In some embodiments, displaying the orientation in real time includes updating the displayed image at least every 1 second, 0.1 seconds, 0.01 seconds, 0.001, and/or 0.0001 seconds.

In one example, the display is mounted to a surgical drill, such that a representation of fluoroscopic images provided by the imaging device can be viewed before, during, and/or after an intramedullary (IM) nailing procedure. In some embodiments, a representation of the alignment of the surgical instrument can be displayed the display mounted to the surgical instrument, so as to guide the medical professional during the IM nailing procedure, when the display is displaying a representation of image sensor data instead of X-ray image data.

The display can be interactive and can aid in various aspects of an IM nailing procedure. For example, the display can aid in determining and enabling the proper entry point trajectory of a given IM nail, as well as determining and enabling the proper location and orientation for distal locking screws for the IM nail.

As an initial matter, because fluoroscopy is a type of medical imaging that shows a continuous X-ray image on a monitor, the terms fluoroscopic data, fluoroscopic image, video data, and X-ray image may be used interchangeably herein, without limitation, unless otherwise specified. Thus, an X-ray image may refer to an image generated during a fluoroscopic procedure in which an X-ray beam is passed through the anatomy of a patient. Further, it will be understood that fluoroscopic data can include an X-ray image, video data, or computer-generated visual representations. Thus, fluoroscopic data can include still images or moving images.

Referring to FIG. 1, a medical imaging system 102 can include a medical imaging device 104 and a surgical instrument assembly 202 in electrical communication with the imaging device 104. The medical imaging device 104, which can be a C-arm device, can include an X-ray generator or transmitter 106 configured to transmit X-rays through a body (e.g., bone) and an X-ray detector or receiver 108 configured to receive the X-rays from the X-ray transmitter 106. Thus, the medical imaging device 104 can define a direction of X-ray travel 128 from the X-ray transmitter 106 to the X-ray receiver 108. The X-ray transmitter 106 can define a flat surface 106*a* that faces the X-ray receiver 108. The medical imaging device 104 can further include an arm 110 that physically connects the X-ray transmitter 106 with the X-ray receiver 108. The medical imaging device 104 can further be communication with a medical imaging device display 112 that is configured to display X-ray images from the X-ray detector 108. In some cases, the medical imaging device display 112 can be hard-wired with the X-ray detector 108, such that the display 112 can be in a fixed position relative to the arm 110.

The medical imaging device 104 is presented as a C-arm device to facilitate description of the disclosed subject matter, and is not intended to limit the scope of this disclosure. Further, the imaging system 102 and the imaging device 104 are presented as a medical imaging system and a medical imaging device, respectively, to facilitate description of the disclosed subject matter, and are not intended to limit the scope of this disclosure. Thus, it will be appreciated that other devices, systems, and configurations may be used to implement the embodiments disclosed herein in addition to, or instead of, a system such as the system 102, and all such embodiments are contemplated as within the scope of the present disclosure. It is recognized herein that the position of the display 112 can create problems for a medical professional. For example, in some cases, the medical professional may need to view images or data rendered by the display 112 while viewing a patient positioned between the X-ray generator 106 and the X-ray detector 108.

In an example, a medical professional may face challenges placing distal locking screws during an IM nailing procedure due to insufficient assistive instruments or guidance systems, such as an aiming arm used in placement of proximal screws. Distal screws are commonly inserted in a freehand technique under fluoroscopic guidance. The freehand technique is commonly referred to as the perfect circle technique. For example, once a perfect circle is established during an IM nailing procedure, it may be difficult to properly align a drill bit to the axis of the distal locking hole due to lack of visibility while using radiographic images. Improper alignment can lead to breaching or cracking of an implant during the drilling of a pilot hole, which can result in implant breakage, poor reduction/fixation, delay of surgery, or the like. It is further recognized herein that an orientation of an X-ray image rendered by the display 112 might not match the orientation of the patient's anatomy, thereby creating further challenges for a medical professional.

As another example of a technical problem addressed by embodiments described herein, before the distal locking screws are placed, a medical professional may face challenges placing the IM nail due to insufficient assistive instruments or guidance systems. IM nails are commonly inserted in a freehand technique under fluoroscopic guidance. Improper placement, however, may result in pain to the patient. For example, different bones and different IM nails require the IM nails to be inserted into the bone at different points of entry and different trajectories, so as to minimize pain. Further, current approaches to determining the appropriate point of entry and trajectory for a specific bone, for instance by consulting a technique guide, can result in errors or delays. In various examples described herein, a surgical instrument assembly can be configured so as guide and help a medical professional during various operations, such as an IM nailing procedure.

The surgical instrument assembly 202 may include a surgical instrument 203 and a sensing unit 207 that is attached to a front portion of the surgical instrument 203. The sending unit 207 may include an image sensor 209 attached to a top of a measuring device 211, which may be attached to the surgical instrument. The image sensor 209 may be configured to face forward, away from the display 212. For example, the image sensor 209 may face forward at a downward angle toward a longitudinal axis A (e.g., about 30° relative to a plane defined by aa lateral axis L and a transverse axis T, each of which are perpendicular to one another and to the longitudinal axis A).

The surgical instrument assembly 202 may include a display 212 that faces away from the image sensor 209 and the measuring device 211. For example, the display 212 may face rearward.

In some embodiments, the sensing unit includes a second image sensor (e.g., a second camera). The second image sensor may be configured to provide for stereovision, redundant monocular-vision, or a combination of the two to achieve greater accuracy or confidence in the image data generated by the image sensors.

In the illustrated embodiment, the image sensor is in electronic communication with the processor via a wired connection. In an embodiment, the image sensor is in electronic communication with the processor via a wireless connection.

The image sensor 209 may be small and light enough to add to the drill without interfering with the mobility of the user. The image sensor 209 may be configured to generate image sensor data with sufficient image quality to be able to detect fiducial markers (e.g., ArUco markers 213 illustrated in FIG. 4D) accurately. For example, the image sensor 209 may be configured to detect visible light, and examples of characteristics of the image sensor 209 are provided in the table below. The image sensor 209 may have any one or combination of the characteristics identified in the table below. The characteristics of the image sensor 209 may be balanced with size, cost, and other considerations when selecting for the surgical instrument assembly 202.

| Example Image Sensor Characteristics | First Option | Preferred Option | Range |
| --- | --- | --- | --- |
| Resolution in Megapixels (MP) | 5 | 16 | 5-16 |
| Frame Rate Per Second (fps) | 7.5 | 30 | 7.5-30 |
| Field of View (degrees) | 60 | 90 | 60-110 |
| Focusing Min Range in millimeters (mm) | 100 | 150 | 100-200 |
| Power Supply in Volts (V) | 5 | 5 | 5 |
| Working Current in milliamps (mA) | 180 | 200 | 180-220 |

In an embodiment, the image sensor 209 may be combined with a lens to achieve one or more of the characteristics identified in the table above.

Figure 3:
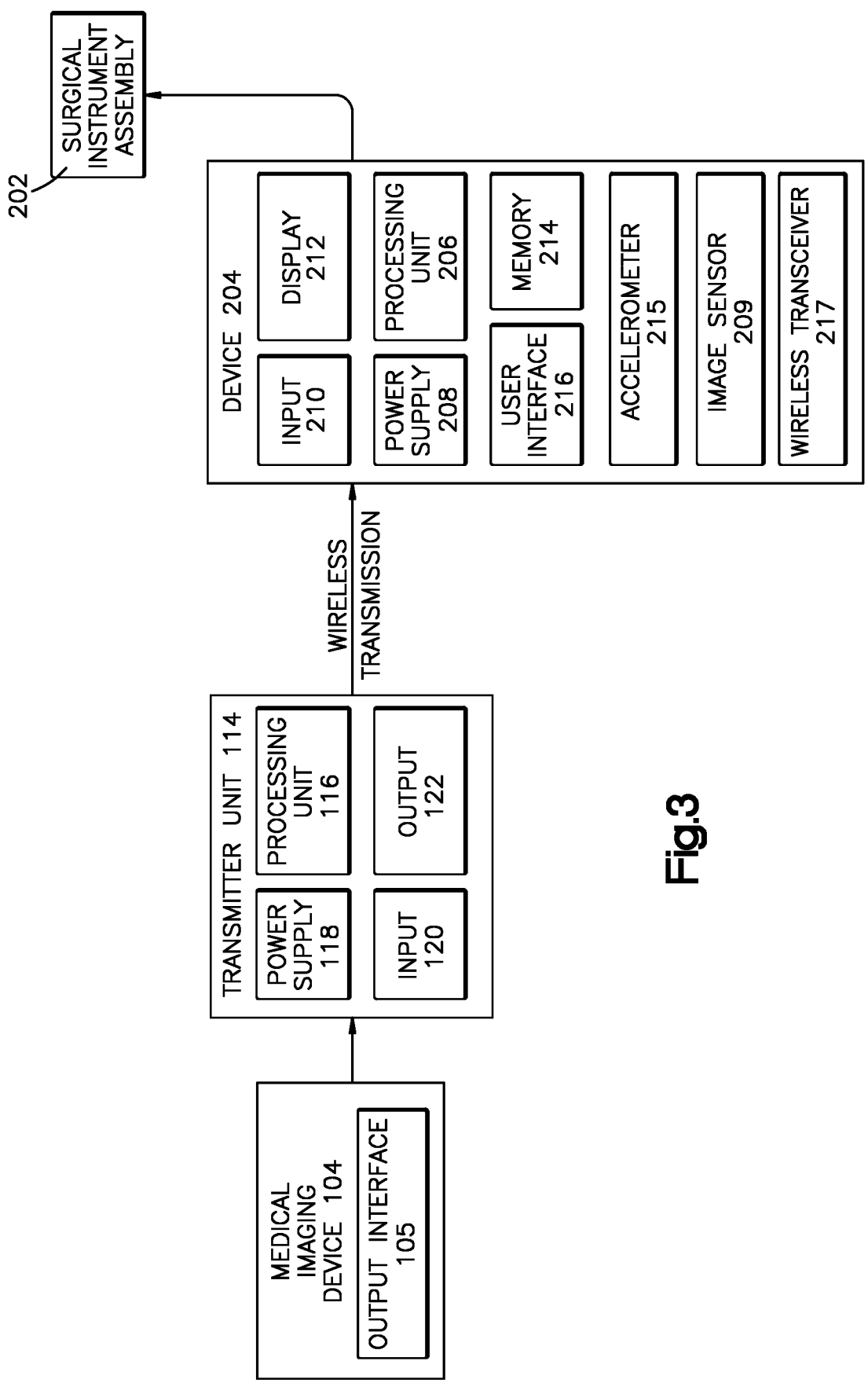
FIG. 3 is a block diagram of a computing device for use in the imaging system shown in FIG. 1.

Referring now to FIG. 3, in one embodiment, data (e.g., video or still images) (an example of X-ray image data) provided by the medical imaging device 104 can be received by an instrument application, for instance an alignment application, which can be a program, such as a software or hardware or combination of both, that can be run on any suitable computing device. As discussed further below, a user can use the instrument application to view representations of an alignment of the surgical instrument 203 and/or representations of images generated by the medical imaging device 104. The instrument application can receive, process, and/or display representations of the alignment and representations of the fluoroscopic images at various locations, for instance at a location that is aligned with a desired trajectory for drilling.

Referring to FIGS. 2 and 3, any suitable computing device 204 can be configured to host the instrument application. It will be understood that the computing device 204 can include any appropriate device, examples of which include a portable computing device, such as a laptop, tablet, or smart phone. In another example, the computing device 204 can be internal to the surgical instrument 203.

In an example configuration, the computing device 204 may include a processing portion or unit 206 (an example of a processor), a power supply 208, the image sensor 209, an input portion 210, the display 212, a memory portion 214, a user interface portion 216, a wireless transceiver 217, and/or an accelerometer 215. It is emphasized that the block diagram depiction of computing device 204 is an example and not intended to imply a specific implementation and/or configuration. The processing portion 206, the image sensor 209, the input portion 210, the display 212, memory 214, user interface 216, the wireless transceiver 217, and/or the accelerometer 215 may be coupled together to allow communications therebetween. The accelerometer 215 can be configured to generate accelerometer information that corresponds to an orientation of the computing device 204. As should be appreciated, any of the above components may be distributed across one or more separate devices and/or locations.

In various embodiments, the input portion 210 includes a receiver of the computing device 204, a transmitter of the computing device 204, or a combination thereof. The input portion 210 is capable of receiving information, for instance fluoroscopic data in real-time, from the medical imaging device 104. As should be appreciated, transmit and receive functionality may also be provided by one or more devices external to the computing device 204, and thus the surgical instrument assembly 202. The input portion 210 may receive and send information via the wireless transceiver 217 to another component, for example, to and from the image sensor 209.

Depending upon the exact configuration and type of processor, the memory portion 214 can be volatile (such as some types of RAM), non-volatile (such as ROM, flash memory, etc.), or a combination thereof. The computing device 204 can include additional storage (e.g., removable storage and/or non-removable storage) including, but not limited to, tape, flash memory, smart cards, CD-ROM, digital versatile disks (DVD) or other optical storage, magnetic cassettes, magnetic tape, magnetic disk storage or other magnetic storage devices, universal serial bus (USB) compatible memory, or any other medium which can be used to store information and which can be accessed by the computing device 204.

The computing device 204 also can contain the user interface portion 216 allowing a user to communicate with the computing device 204. The user interface 216 can include inputs that provide the ability to control the computing device 204, via, for example, buttons, soft keys, a mouse, voice actuated controls, a touch screen, movement of the computing device 204, visual cues (e.g., moving a hand in front of a camera on the computing device 204), or the like. The user interface portion 216 can provide outputs, including visual information (e.g., via a display), audio information (e.g., via speaker), mechanically (e.g., via a vibrating mechanism), or a combination thereof. In various configurations, the user interface portion 216 can include a display, a touch screen, a keyboard, a mouse, an accelerometer, a motion detector, a speaker, a microphone, a camera, a tilt sensor, or any combination thereof. The user interface portion 216 can further include any suitable device for inputting biometric information, such as, for example, fingerprint information, retinal information, voice information, and/or facial characteristic information. Thus, a computer system such as the computing device 204 can include a processor, a display coupled to the processor, and a memory in communication with the processor. The memory can have stored therein instructions that, upon execution by the processor, cause the computer system to perform operations, such as the operations described herein. The display 212 can be configured to display visual information, such as described with reference to FIGS. 4A-4O, FIGS. 5A-G, and FIGS. 10A to 20.

Referring to FIGS. 1 and 3, a transmitter unit 114 can be electrically coupled to, or can be part of, the medical imaging device 104. The transmitter unit 114 can be any suitable computing device configured to receive and send images, for instance video signals including fluoroscopic images. It will be understood that the transmitter unit 114 can include any appropriate device, examples of which include a portable computing device, such as a laptop, tablet, or smart phone.

Referring in particular to FIG. 3, in an example configuration, the transmitter unit 114 can include a processing portion or unit 116, a power supply 118, an input portion 120, and an output portion 122. It is emphasized that the block diagram depiction of transmitter unit 114 is an example and not intended to imply a specific implementation and/or configuration. The processing portion 116, input portion 120, and output portion 122 can be coupled together to allow communications therebetween. As should be appreciated, any of the above components may be distributed across one or more separate devices and/or locations.

In various embodiments, the input portion 120 includes a receiver of the transmitter unit 114, and the output portion 122 includes a transmitter of the transmitter unit 114. The input portion 120 is capable of receiving information, for instance fluoroscopic images or video data, from the medical imaging device 104, in particular an output interface 105 of the medical imaging device 104. The output interface 105 can include a coaxial output, a usb output, a component output, a wireless output, or the like. As should be appreciated, transmit and receive functionality may also be provided by the medical imaging device 104. In an example, the transmitter unit 114 is electrically coupled to the output interface 105 of the medical imaging device 104, so as to establish a wired or wireless electrical connection between the transmitter unit 114 and the display 112. The output interface 105 can include or more video output connectors using the matching input module. In an example, the processing portion 116, which can include or more processors running on an embedded operating system, can detect the presence of a signal, for instance a video signal including fluoroscopic images, from the medical imaging device 104. The processing portion 116 can process the signal as necessary for transmitting to the surgical instrument assembly 202. For example, the processing portion 116 can compress the signal so as to reduce the bandwidth that is used for transmitting the signal.

After the processing portion 116 performs processing on the video signal, as necessary, the video signal that can include fluoroscopic images can be sent by the output portion 122 of the transmitter unit 114 to the input portion 210 of the computing device 204. The output portion 122 of the transmitter unit 114 can be configured to transmit fluoroscopic images in accordance with any communication protocol as desired. For example, the output portion 122 can include a ZigBee module connected to the processing portion 206 via a universal serial bus (USB), such that the output portion 122 can send data wirelessly (via a wireless communications channel) in accordance with any ZigBee protocol. The output portion 122 can send video signals, for instance fluoroscopic images, over Wi-Fi, Bluetooth, broadcast, or any other wireless communication channels as desired. The output portion 122 can send a single X-ray image (also referred to as a "snapshot") at a time.

Accordingly, the input portion 210 of the device 204 can receive data or video signals in real-time, for instance fluoroscopic images, which are sent via a wireless communication channel from the medical imaging device 104. The input portion 210 can be configured to receive ZigBee messages, Wi-Fi messages, Bluetooth messages, broadcast messages, or messages formatted in accordance with any wireless protocol as desired. In an example, when the input portion 210 of the device 204 receives the fluoroscopic images from the medical imaging device 104, the images can be retrieved and verified by the processing portion 206 of the computing device 204. For example, the processing portion 206 can verify that the received images are from the appropriate medical imaging device. The images can be forwarded to the display 212, for example, when the images are verified. The processing portion 206 can also ensure that valid data is displayed. For example, if there is an interruption to the wireless communication channel or connection between the computing device 204 and the medical imaging device 104, the processing portion 206 can identify the interruption, and send a message to the display 212 so that the interruption is conveyed to a medical professional who views the display 212. In some cases, the processor 206 can cause the surgical instrument assembly 202 to display an indication of error on the display 212 when a quality of the communication link between the imaging device 104 and the surgical instrument assembly 202 is below a predetermined threshold. Thus, a wireless point-to-point communication channel or connection between the transmitter unit 114 and the computing device 204 can be established, and the wireless point-to-point connection can be managed by the input portion 210 and the output portion 122 on the physical layer, and the processing portions 116 and 206 at the application layer.

Referring again to FIG. 1, the image sensor 209 may provide image sensor data to a processing unit 206. The image sensor 209 may be connected to the processing unit 206 via a cable. For example, the image sensor 209 may be directly connected to the processing unit 206. In an embodiment, the image sensor is housed together with the processing unit 206.

In another embodiment, the image sensor is wirelessly connected to the processing unit 206 (e.g., via a wifi or Bluetooth module). For example, the image sensor data generated by the image sensor may be sent via wifi to a private URL which may be accessible to the processing unit 206 to obtain the image sensor data.

The processing unit 206 may receive the image sensor data from the image sensor and generate navigation graphics on the display 212 based on the image sensor data.

The display unit 212 may be reusable. For example, the display unit 212 may be sterilized before surgery. The sterilized display unit 212 may be sterilely removably attached to the surgical instrument 203 after such sterilization. For example, the display unit 212 may be removable attached via gravity, a push-lock, or a magnet that ensure the display unit 212. The display unit 212 and the surgical instrument 203 may include corresponding connectors that align with one another to ensure the display 212 is correctly attached to the surgical instrument. In an embodiment, the display and the image sensor may be sterilized and packaged together. For example, the image sensor and the display may be removed from the respective packaging and each may be separately attached to the corresponding location of the surgical instrument.

In an embodiment, the display may be able to be removed from the surgical instrument and placed elsewhere in the room for viewing. For example, the display may include a clamp, a stand, or another component configured to hold or place the display on a table or other fixture. Removing the display may provide the surgeon with flexibility by reducing drill weight and/or reducing view obstruction.

With reference to FIGS. 2A-D and 13, the display 212 may be configured to be fixed relative to the surgical device 203 (e.g., along a longitudinal axis A of the drill bit).

The surgical instrument 203 can define a proximal end 203b and a working end 203a opposite the proximal end 203b. The working end 203a can be configured to operate on, for instance cut, drill, or otherwise target, a structure, for instance the anatomical structure 124, of a medical patient. The display 212 can face the proximal end 203b. The display 212 can be positioned so as to provide a line of sight to both the working end 203a and the display 212 from a location proximate of the surgical instrument 203. Thus, in some cases, for example, a medical professional can, while operating the surgical instrument 203, view both the display 212 and the working end 203a of the surgical instrument 203.

In an example, the surgical instrument 203 includes a cutting instrument 226 that includes a proximal end 226b adjacent to the body 205 of the surgical instrument 203, and a cutting tip 226a opposite the proximal end 226b of the cutting instrument 226. The cutting tip 226a can define a terminal end of the cutting instrument that is opposite to the proximal end 226b of the cutting instrument 226. The cutting instrument 226 can have the cutting tip 226a that can be configured to remove anatomical material from an anatomical structure, for instance the anatomical structure 124. In the illustrated example, the cutting instrument 226 is a drill bit, and the cutting tip 226a is a tip of the drill bit, though it be appreciated that other instruments and configurations may be used to implement the embodiments disclosed herein in addition to, or instead of, an instrument such as the cutting instrument 226, and all such embodiments are contemplated as within the scope of the present disclosure.

The image sensor 209 may be positioned in front of the display 212 so as to have an unobstructed view of the cutting tip 226a, the fiducial markers 213, and/or fiducial markers discussed below with reference to FIGS. 4D-4Z. The image sensor 209 may be rotatable relative to the surgical instrument 203 and the display 212. The image sensor may be removable from the surgical instrument 203, which may provide for the image sensor 209 to be sterilized and reused.

In an embodiment, the image sensor may be configured for a single use. For example, the image sensor may be permanently attached to the surgical instrument.

The image sensor 209 may be calibrated. For example, the image sensor 209 may be calibrated by using a standard chessboard calibration method or any other well accepted method of obtaining the intrinsic parameters and distortion coefficients. In an embodiment, the image sensor calibration is done with calibration techniques using a chessboard or other planar pattern. For example, the technique proposed by Zhengyou Zhang wherein at least two orientations of a planar pattern are observed by the pattern to calibrate the camera in a closed-form manner. Zhang, Zhengyou. (2000). A Flexible New Technique for Camera Calibration. Pattern Analysis and Machine Intelligence, IEEE Transactions on. 22. 1330-1334. 10.1109/34.888718. In an embodiment, another suitable camera calibration method is used to calibrate the image sensor.

In an embodiment, the image sensor is calibrated to obtain the intrinsic parameters and the distortion coefficients during device manufacturing and the calibration is stored by the image sensor or another device in communication with the processing unit 206 (FIG. 3).

Figure 8:
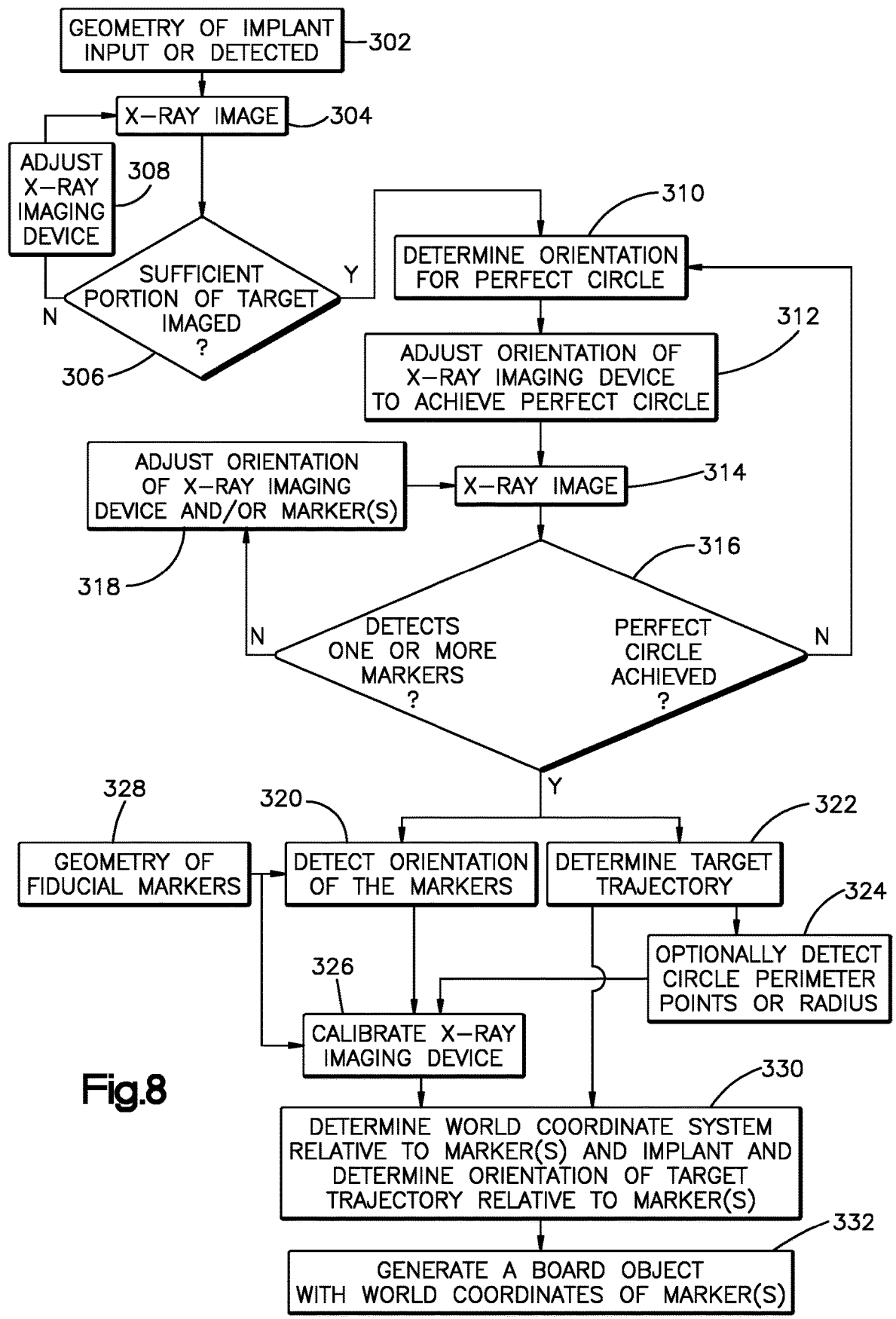
FIG. 8 depicts a flow chart of an example algorithm including determining an orientation of a desired trajectory relative to the fiducial markers.

Turning now to FIG. 8, an example flow chart of steps followed by an X-ray imaging application, for instance an orientation application, which can be a program, such as a software or hardware or combination of both, that can be run on the computing device 204 or another computing device. At step 302 a geometry of the implant may be input or detected. For example, the user may input a specific IM nail and choose a target hole in the IM nail via the user interface 216. The specific nail geometry and the target hole location may be input or detected.

In an embodiment, the user inputs the model of the C-arm that will generate an X-ray image(s) of the IM nail and adjacent anatomical structure. The X-ray imaging application may be configured to access calibration data specific to the C-arm. In an embodiment, the C-arm includes an inertial motion unit (e.g., including an accelerometer) to determined the orientation of the C-arm. The orientation may be provided by the inertial motion unit to the computing device of the surgical instrument assembly, for example.

C-arm calibration data that is model-specific for the C-arm may be stored by the computing device 204 and/or the medical imaging device 104. The calibration data may include a full volume of C-arm imagable space. Calibration of the C-arm can be done once per model and stored on the computing device 204 and/or the medical imaging device 104 for later use.

Calibration of the C-arm may include using a volumetric fixture with identifiable radiopaque markers placed throughout the fixture at predetermined locations. Fluoroscopic images may be taken of the markers and the 2D image locations of each marker mapped to the exact spatial position, which may be known from the fixture. Thereby the entire volume of imagable space between the C-arm transmitter 106 and the receiver 108 can be mapped out and output as the calibration data. X-ray images generated by the C-arm may be processed using the mapping to determine the 3D coordinates of features on the 2D image X-ray image.

The calibration may be done in one orientation and the negligible changes to the image geometry due to c-arm angle may be disregarded. In an embodiment, the calibration may be done at different angles and an angle measuring device may be integrated into the c-arm for use in selecting or interpolating to the calibration data that is most appropriate. Some modern c-arms may already have this functionality built-in. An example of the volumetric calibration is given in: Hosseinian S, Arefi H, Navab N. Toward an End-to-End Calibration for Mobile C-Arm in Combination with a Depth Sensor for Surgical Augmented Reality Applications. Sensors (Basel). 2019; 20(1):36. Published 2019 Dec. 19. doi: 10.3390/s20010036.

The user may input the model of the medical imaging device 102 (e.g., the C-arm) to the user interface 216, for example, when inputting the specific IM nail. The display 212 may display a dropdown list of stored C-arm models to be selected from. In an embodiment, the C-arm has an electronic or scannable identification label (such as a QR code) that can provide the system any necessary model-specific information.

In an embodiment, a single fluoroscopic image may be used to approximate the C-arm imaging geometry as that of a pinhole camera. Intrinsic matrix and distortion coefficients may be estimated using the pattern on rigid markers (for example, four outer corners of an ArUco marker) using Zhang's method, for example. In an embodiment, multiple fiducial markers may be detected in the single fluoroscopic image to estimate the matrix and distortion coefficients using Zhang's method. In some embodiments, the geometry of the IM nail, including holes, may be used in addition to the fiducial markers to give more calibration points for using Zhang's method.

In the case of ArUco markers, the markers may detected using OpenCV's detectMarkers function. This may provide image points for each of the four corners of each ArUco marker. Object points for each ArUco marker may be predetermined, as discussed below. Zhang's method may be used the ArUco markers using OpenCV's calibrateCamera function with the image points and the object points. For example, the ArUco markers may be detected using OpenCV's functions, such as cv::aruco::detectMarkers, cv::aruco::estimatePoseBoard, and/or cv::aruco::estimatePoseSingleMarkers.

Registering the fiducial markers to a desired trajectory (e.g., a central axis of a target hole in the IM nail) may include determining a world coordinate system at step 330. For example, a rotation matrix or a translation matrix for mapping the C-arm coordinate system (e.g., when the C-arm is modeled as a pinhole camera) to a world coordinate system centered at the desired trajectory is calculated. For the world coordinate system, a Z-axis may be aligned with the desired trajectory (e.g., the central axis of the targeted through-hole) and the X-axis may be aligned with the longitudinal axis of the implant (e.g., the IM nail).

The rotation and translation matrices may be determined by using a PnP method with the detected edges of the targeted through-hole (e.g., when depicted as a perfect circle in the fluoroscopic image). Edge detection may be done by any suitable detection process. For example, OpenCV's Canny Edge Detector may perform the edge detection. In an embodiment, OpenCV's Blob Detector may be used to find a circular shape that meets certain shape pre-requisites such as circularity and minimum/maximum area. Multiple points along the edge may be used as a 2D set of points to match with the known 3D points of the through-hole's perimeter (e.g., using a predetermined radius of the through-hole) at optional step 324.

If the fluoroscopic image does not show a perfect circle, then a transformation application may be used to determine the angles of rotation needed to align with the perfect circle and those angles can be used to create the rotation matrix. The translation matrix may also be found by identifying the center point of the detected through-hole (e.g., a circle, or circular arc in the case of the non-perfect circle image) rather than using edge points.

The 3D coordinates of each individual marker key points would be stored in the computing device 204 based on the known geometry of the fiducial markers. For example, the four corners of an ArUco marker of side length L may be saved as the following array with the origin set as the upper left hand corner [[0,0,0],[L,0,0],[L,−L,0],[0,−L,0]]. All fiducial marker information may be combined into an array of arrays, which may be referred to as an array of object points for the board of fiducial markers.

Key points of each fiducial marker may be detected using PnP. The relative pose of the c-arm (e.g., in the form of rotation and translation vectors) may be stored in the computing device 204. For example, ArUco markers may be detected thereby providing the image points of the four corners. After, the image point data may be used with the known object points to determine the rotation and translation vectors. This determination may be done at the same time as the C-arm calibration is being done using the single C-arm image. The rotation and translation vectors may be saved in an array and correlated with the specific identification of the corresponding marker.

The object points of the marker corners may then be put through a change of basis from their local coordinate system (e.g., defined in the plane of the marker with the origin at the upper left hand corner) to the C-arm coordinate system. Next the object point may be put through another change of basis from the C-arm coordinate system to the world coordinate system centered on the desired trajectory (e.g., the central axis of the target through-hole).

The object points may then be used to create an ArUco board object at step 332 (e.g., an array of arrays of each marker's world coordinates which correspond to another array of marker identifiers). The ArUco board object may be used in later marker board detection using the image sensor 209.

The resulting image sensor 209 pose may be provided relative to the world coordinate system centered at the image sensor 209. In an embodiment, the drill bit is targeted at the world origin via the navigation graphics.

Figure 4A:
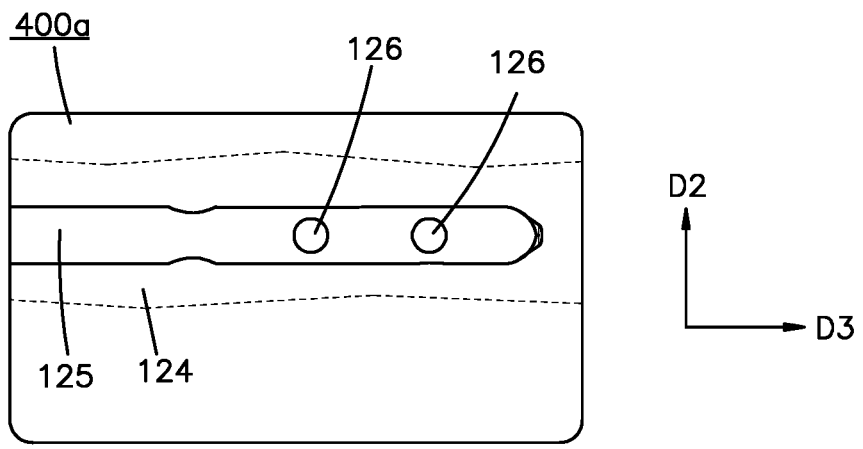
FIG. 4A depicts a representation of an anatomical structure and an implant that can be displayed by the surgical instrument assembly depicted in FIGS. 2A-D, wherein the representation includes a target location.
Figure 4B:
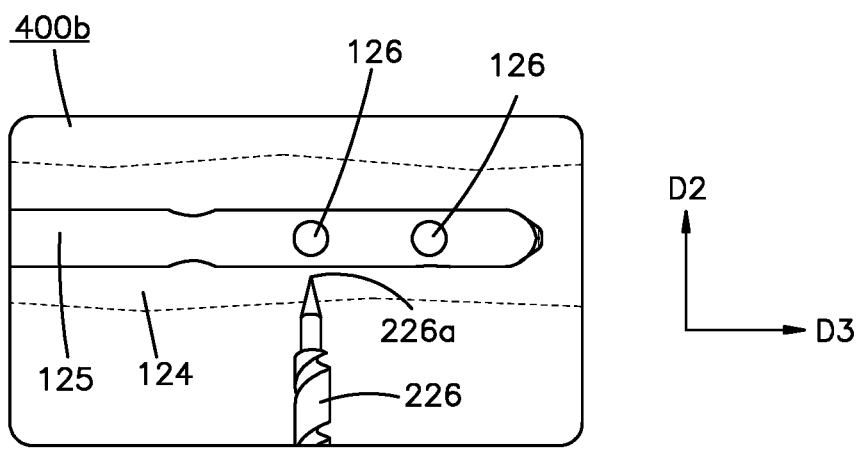
FIG. 4B depicts another representation of the anatomical structure and the implant, showing a representation of an orientation and position of a cutting instrument of the surgical instrument assembly relative to the target location of the anatomical structure.
Figure 4C:
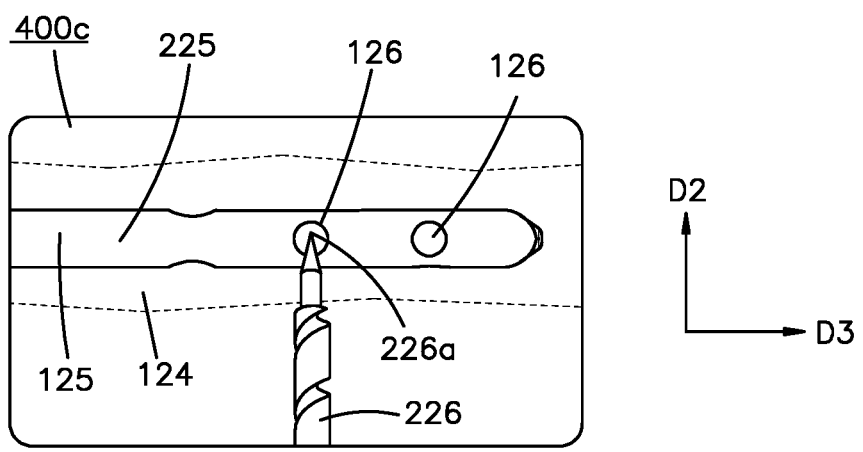
FIG. 4C depicts yet another representation of the anatomical structure and the implant, wherein a tip of the cutting instrument is positioned over the target location.

If the fiducial markers are observed in more than one fluoroscopic image (e.g., in both the first x-ray with 30% of two holes shown at step 304 and in the second perfect circle x-ray at step 316), the fiducial markers from both images may be used to more accurately calibrate the C-arm with the calibration application at step 326. In an embodiment, the C-arm image is cropped down to a central region (e.g., as exemplified in FIGS. 4G and 4L), which typically may have less distortion than the peripheral radial edges of the fluoroscopic image. The intrinsic matrix and distortion coefficients may be determined based on the cropped image of the central region, rather than the entire image or any markers or data outside of the central region.

Re-projection error may be checked for the set of points and compared against a pre-determined threshold to determine if the quality of calibration is sufficient to enable accurate navigation. The calibration may alternatively or in addition employ the same methods as used in the MaxFrame project as described in U.S. Patent Publication No. US 2021/0077194 entitled "Othopedic Fixation Control and Manipulation."

At step 304 the fluoroscopic image may be taken. At step 306 it may be determined whether a sufficient portion of the target is imaged. For example, a sufficient portion of the targeted area of the IM nail may be at least 30% of the two distal holes of the IM nail being shown in the fluoroscopic image. If so, an angular adjustment for the C-arm may be determined based on the orientation of the target (e.g., the target through-hole) in the image. For example, angular adjustments to the C-arm that will result in a perfect circle image at step 312 may be determined at step 310. The adjustment information may be conveyed to the appropriate application or user (e.g., C-arm tech or surgeon) for adjustment at step 312.

In an embodiment, the orientation of the desired trajectory (e.g., the central axis of the target through-hole) is determined without achieving the perfect circle image. For example, the orientation of the central axis of the target through-hole may be determined based on the predetermined characteristics of the IM nail and/or the target through-hole discussed above.

If a sufficient portion of the target is not imaged, the C-arm may be adjusted to a different orientation at step 308 and step 304 may be repeated with the C-arm at a different orientation relative to the implant.

In an embodiment, the fiducial marker locations in the fluoroscopic image are detected and compared to the partial holes that can be seen on the image (e.g., as shown in FIGS. 4E-4H). The spatial locations of each fiducial marker may be calculated relative to the IM nail geometry provided at step 328. Determining the relationship between the fiducial markers and the IM nail may provide for rendering steps 310-316 optional. Thus, determining the relationship between the fiducial markers and the IM nail may provide for full navigation to any distal locking hole of the IM nail, without the additional perfect circle fluoroscopic image. In this case, the entirety of the distal locking may be performed based solely on a single fluoroscopic image.

A further fluoroscopic image may be taken at step 314 after adjusting the orientation of the C-arm at step 312 to achieve the perfect circle fluoroscopic image (e.g., as shown in FIGS. 4J-4M.

If one or more fiducial markers is not detected or if the perfect circle fluoroscopic image is not achieved, the orientation of the C-arm may be adjusted at step 318 so that at least one fiducial marker is in view of the C-arm image and so that the perfect circle is achieved. In an embodiment, the orientation and/or position of the fiducial markers may be adjusted.

The orientation of the fiducial markers may be detected in the image at step 320 and the relative spatial locations compared to the desired trajectory may be determined at step 322. Depth information (e.g., in the direction parallel to the central axis of the targeted through-hole) may be determined by the processing unit based on the image sensor data. In an embodiment, the depth information is not determined (e.g., if the user is able to drill along the axis of the target hole, they will feel when they are drilling bone and do not need Z-axis visual feedback). Fiducial marker detection in the fluoroscopic image, the image sensor image, or both may be less accurate for depth (Z-axis) than for X-coordinates and Y-coordinates.

In an embodiment, C-arm intrinsic and extrinsic parameters may be determined using only the single fluoroscopic image. The C-arm calibration may be performed, as discussed above, based on the single fluoroscopic image. The origin of the world coordinate system may be placed with the X-axis parallel to the longitudinal axis of the IM nail and the Z-axis may be parallel to the desired trajectory (e.g., the central axis of the targeted distal locking through-hole).

If a fiducial marker falls off, is outside the field of view of the C-arm, or otherwise becomes obscured from view or ineffective, there may still be sufficient quantity of other fiducial markers in the array of fiducial markers to perform the steps laid out above. If there are insufficient markers remaining, one or more additional fiducial markers may be placed in the field of view to supplement the existing fiducial markers in the field of view. After placing the additional fiducial marker(s) in the field of view, one X-ray image may be taken to register the fiducial markers to the IM nail.

As shown in FIGS. 2A-2D, the measuring device 211 may be located in front of the display 212. The measuring device 211 may be releasably attached or fixed relative to the surgical instrument 203. For example, an attachment member 218 may releasably attach the measuring device 211 to the surgical instrument 203. In an embodiment, the measuring device is configured and used in the manner described in U.S. Pat. No. 10,736,644 issued on Aug. 11, 2020 and entitled "Surgical power drill including a measuring unit suitable for bone screw length determination."

A sleeve 219 may be provided to interact with the measuring device 211. The sleeve may be configured to slide onto the drill bit 226 such that the sleeve 219 is moveably along the longitudinal axis A. The sleeve 219 may include fiducial markers 213, as noted above. For example, a rearwardly facing surface of the sleeve 219 may include the fiducial markers 213.

The measuring device 211 may be configured to detect the fiducial markers 213 on the rearward facing surface of the sleeve 219. The distance between the measuring device 211 and the sleeve may be determined based on the detected fiducial markers 213 of the sleeve 219. For example, the measuring device 211 may determine the distance between the sleeve 219 and the measuring device 211 based on an orientation and/or size of the detected fiducial markers 213.

The sleeve 219 may be positioned at a predetermined location on the drill bit (e.g., spaced a predetermined distance along the longitudinal axis A from the drill tip 226a or flush with the drill tip 226a). Thus, the orientation and length of the drill tip 226 may be determined based on the orientation of the fiducial markers 213 detected by the measuring device 211.

In an embodiment, the measuring device outputs to the computing device 204 data representing the orientation and/or position of the sleeve and/or the drill tip. In an alternative embodiment, the sleeve may be displaceable an angle relative to the longitudinal axis A and the measuring device may be configured to detect such angular displacement.

In an embodiment, the sleeve is includes a reflector plate to register the drill bit (e.g., the end of drill bit tip). For example, the measuring device may include a laser device for detecting linear displacement assessment between the measuring device and the reflector plate of the sleeve. This laser device may be configured to emit light and detect the emitted light that is reflected back by the reflector plate.

The measuring device may be configured to determine linear displacement between the sleeve and the measuring device based on the detected reflected light. For example, the measuring device may perform laser triangulation for linear displacement assessment. In an embodiment, the linear displacement assessment can be performed by using ultra sound position sensors to detect ultra sound waves emitted at the reflector plate.

The orientation, size, and/or position of the drill bit 226 relative to the image sensor 209 may be determined based on the orientation, size, and/or position of the drill bit in image data, representing the drill bit 226, detected by the image sensor 209. For example, based on the orientation, size, and/or position detected by the measuring device 211. The measuring device 211 may communicate (e.g., via a wired or wireless electronic connection) the orientation, size, and/or position of the drill bit 226 to the computing device 204.

The position/location of the drill bit relative to the image sensor 209 may be determined so that it can be referenced for the navigation output to the display 212. Registering the drill bit 226 may be based on the output of the measuring device 211 The registration may be based on the orientation, size, and/or position detected by the measuring device 211 and determining the orientation and position of the image sensor relative to the drill bit 226 based on a predetermined relationship between the image sensor 209 and the measuring device 211.

In an embodiment, the image sensor is configured to determine the distance between the sleeve and the image sensor based on an orientation and/or size of the fiducial markers of the sleeve detected by the image sensor. For example, the image sensor may be configured to perform the functions of the measuring device 211 discussed above. In some embodiments, the sleeve includes a unique geometry that is detected by the image sensor instead of fiducial markers or in addition to the fiducial markers.

In an embodiment, the image sensor is configured to determine the orientation, size, and/or position of the drill bit relative to the image sensor. The image sensor may be configured to detect the drill bit and use image recognition to automatically determine the orientation, size, and/or position of the drill bit relative to the image sensor. For example, the image sensor and/or the computing device may be trained (e.g., by using neural networks) to distinguish drill bits from other objects in the environment.

The diameter of the drill bit may be determined based on the target IM nail and target through-hole input by the user (e.g., a 5.2 millimeter (mm) diameter distal locking hole may mean the user is using a 5.0 mm drill bit). The diameter may then used to fit the expected points on the drill bit outer diameter to drill bit edges detected by the image sensor. Thus, the image sensor and/or the computing device may determine the 3D coordinates of the drill bit using, for example, the Points-N-Perspective (PnP) method discussed below.

In an embodiment, the spatial relationship between the image sensor, the drill bit, and the fiducial markers may be determined using any variation of the PnP method. The PnP method may use a given set of rigidly arranged 3D points and their corresponding 2D image projections with a calibrated image sensor 209 to determine the image sensor pose. In some embodiments, one or more of the following functions or methods may be used: OpenCV's SOLVEPNP_ITERATIVE, Efficient PnP (EPnP) as proposed by Vincent Lepetit, Perspective-Three-Point (P3P) as proposed by Xiao-Shan Ga, Algebraic P3P (AP3P) as proposed by Tong Ke, or Consistently Fast and Globally OptimalSolution PnP (SQPnP) as proposed by George Terzakis.

In some embodiments, the image sensor provides sufficient information of the pose of the drill relative to the image sensor and the fiducial markers such that neither the measuring device nor the accelerometer are utilized. For example, in an embodiment, the accelerometer and measuring device may be omitted from the surgical instrument assembly.

In some embodiments, the image sensor is the only component mounted to the surgical instrument. For example, the image sensor may be configured to communicate with the computing device, which may be separate from the surgical instrument. Such communication may be wireless. In an embodiment, the image sensor and the display are the only components mounted to the surgical instrument. The image sensor and the computing device may be configured to communicate with one another and/or the display.

The surgical instrument assembly may be assembled by the user (e.g., the surgeon) or another person (e.g., a scrub technician).

Fiducial markers 213a, which may be substantially the same as those discussed above, may be fixed relative to a target area for surgery. The fiducial markers 213a may be placed at any time prior to taking the X-ray image at step 304. The fiducial markers 213a may be placed after step 304 and prior to step 314, if steps 310-316 are being performed. The fiducial markers 213a may be fixed relative to the patient's anatomy being operated on prior to the surgical procedure (e.g., while patient prep is being done). The fiducial markers 213a may not interfere with other steps of the IM nailing procedure.

For example, an array of fiducial markers 213 may be stuck to the patient's skin (e.g., as shown in FIGS. 4U and 4W-4Z). In an embodiment, the fiducial markers are adhered to a layer of material that is in contact with the patient's skin. Adhesion to the patient skin or to a layer adjacent to the patient skin (eg. drape, Ioban). May be incorporated into the drape or adhered onto the drape. May be taped onto the patient using Ioban or other tape- or strap-like devices. May use staples, tacks, or burr-like mechanisms to latch onto the skin or layer. May include protrusion(s) that can be hammered or drilled into the patient bone for securement (ie. bone tack). May attach to the proximal end of the nail or the nail handle with an extended, adjustable means to place the markers in the correct area near the distal locking portion of the nail.

Figure 4D:
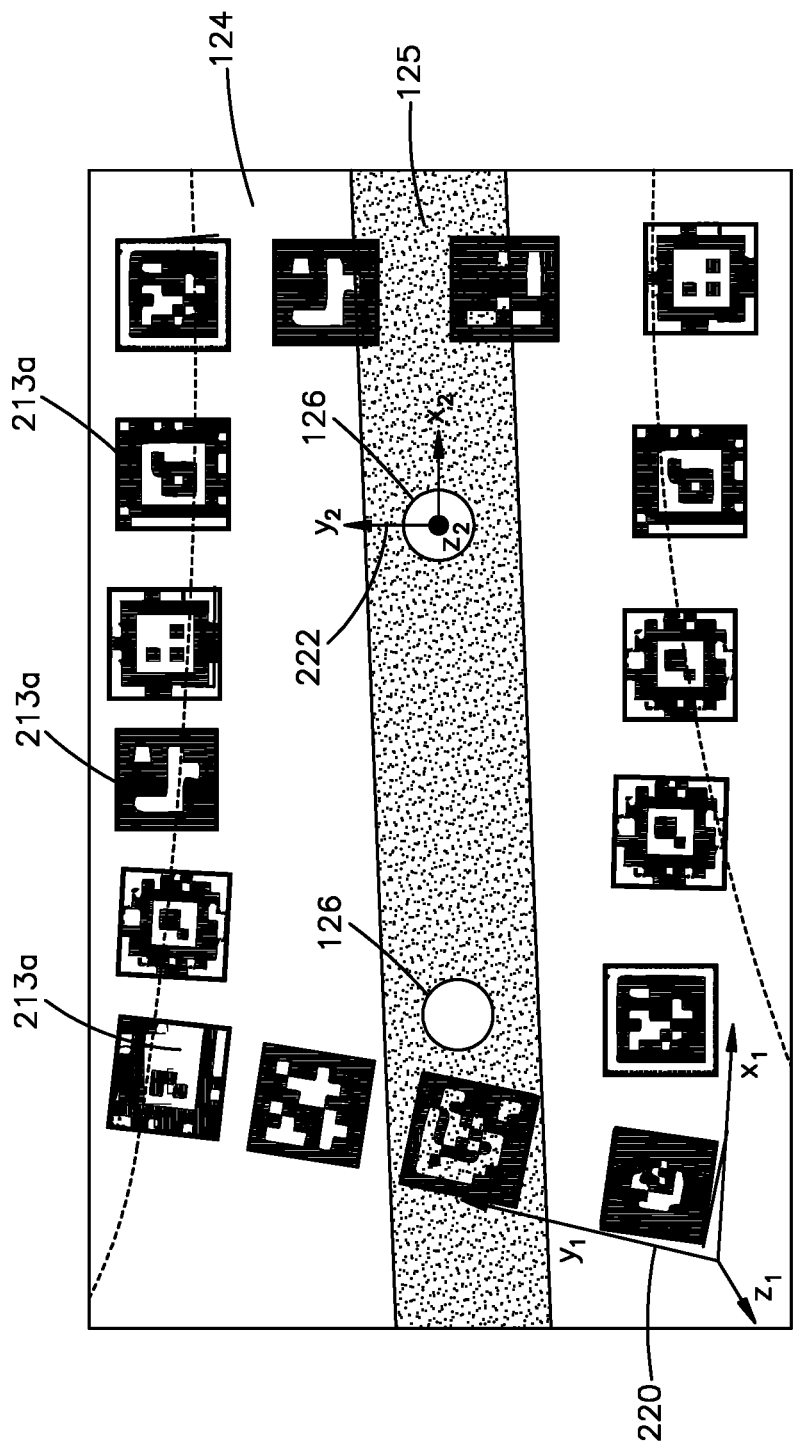
FIG. 4D depicts an X-ray image of an array of fiducial markers, the anatomical structure, and the implant, showing a world coordinate system and an image sensor coordinate system.
Figure 4E:
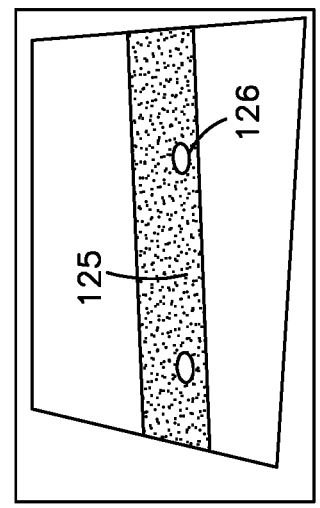
FIG. 4E depicts another X-ray image of an array of fiducial markers, the anatomical structure, and the implant.
Figure 4F:
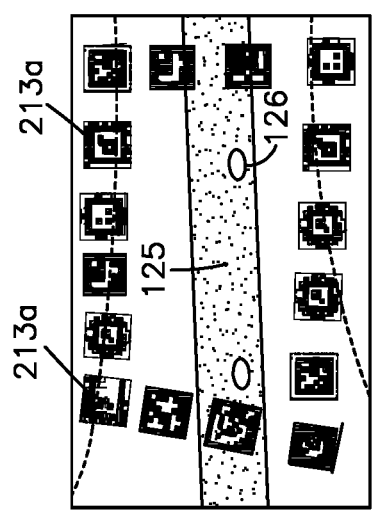
FIG. 4F depicts the X-ray image of FIG. 4E, in which the brightness and contrast may be adjusted to detect the fiducial markers.
Figure 4G:
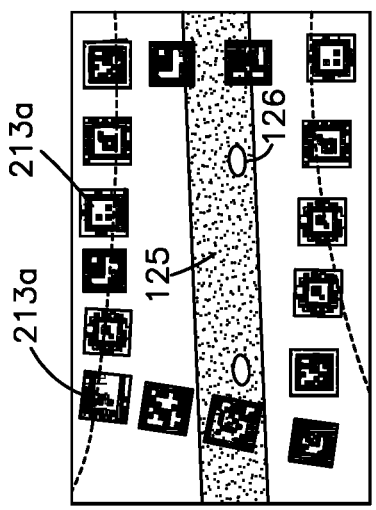
FIG. 4G depicts a cropped portion of the X-ray image of FIG. 4F.
Figure 4H:
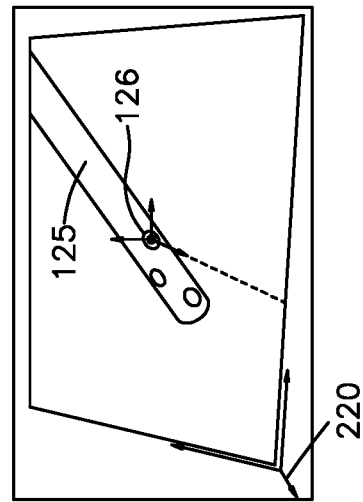
FIG. 4H depicts the X-ray image of FIG. 4F, showing a world coordinate system and a desired trajectory.
Figure 4I:
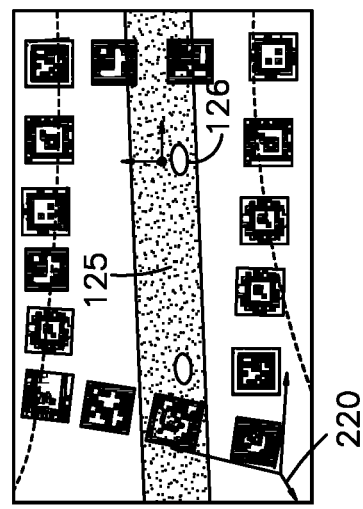
FIG. 4I depicts the X-ray image of FIG. 4H, without the fiducial markers.
Figure 4J:
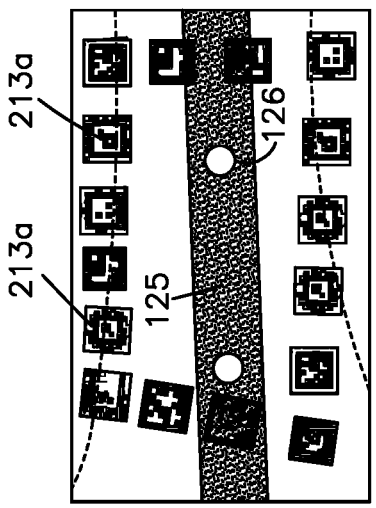
FIG. 4J depicts yet another X-ray image of an array of fiducial markers, the anatomical structure, and the implant, viewed at an angled of a desired drilling trajectory.
Figure 4K:
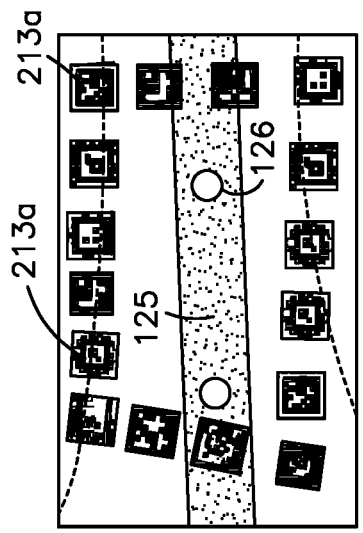
FIG. 4K depicts the X-ray image of FIG. 4J, in which the brightness and contrast may be adjusted to detect the fiducial markers.
Figure 4L:
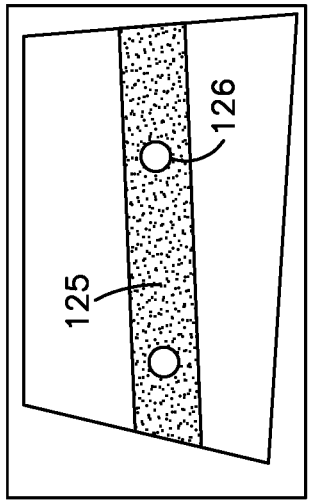
FIG. 4L depicts a cropped portion of the X-ray image of FIG. 4K.
Figure 4M:
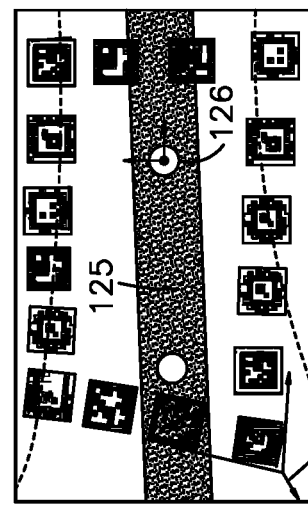
FIG. 4M depicts the X-ray image of FIG. 4K, showing a world coordinate system and a desired trajectory.
Figure 4N:
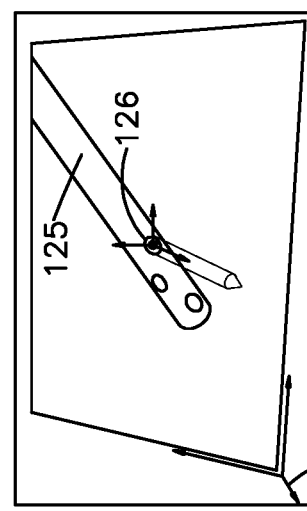
FIG. 4N depicts the X-ray image of FIG. 4K, without the fiducial markers, showing a representation of a cylinder for determining 2-dimensional coordinates of a target.
Figure 4O:
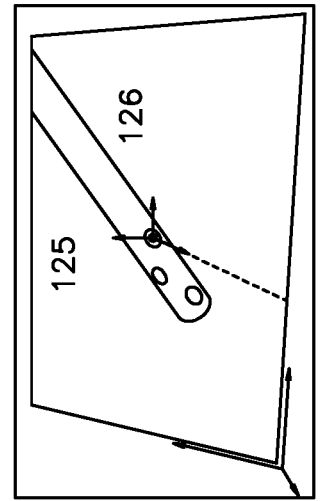
FIG. 4O depicts the X-ray image of FIG. 4K, without the fiducial markers, showing a position of a desired target.
Figure 4P:
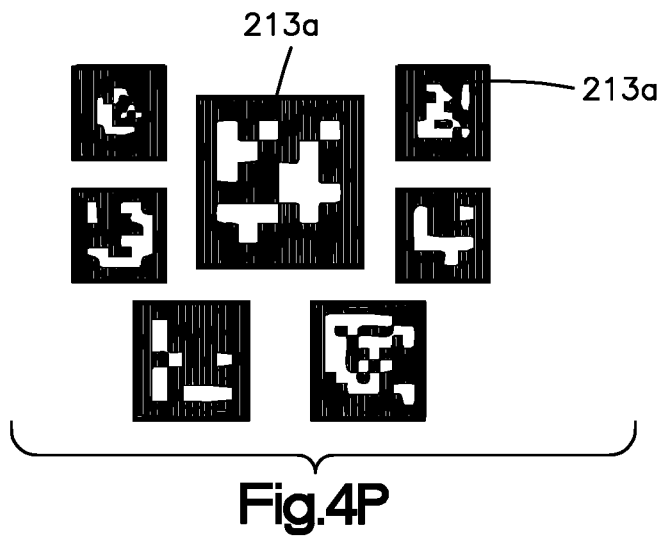
FIG. 4P depicts ArUco markers.
Figure 4Q:
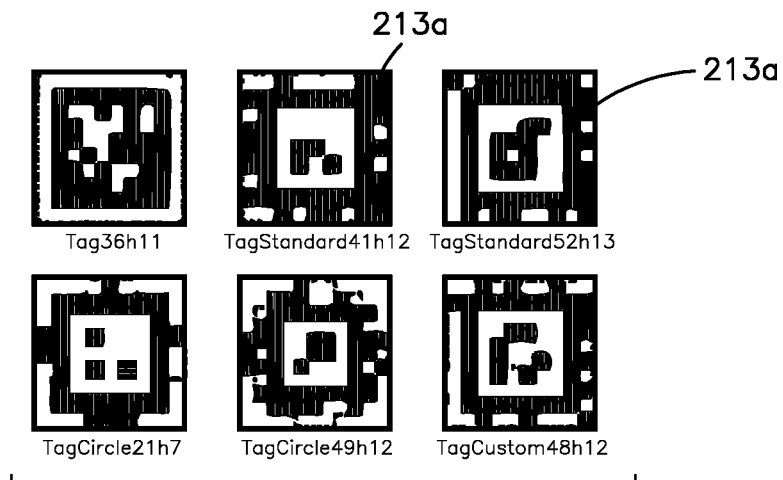
FIG. 4Q depicts ArUco markers with AprilTags.
Figure 4R:
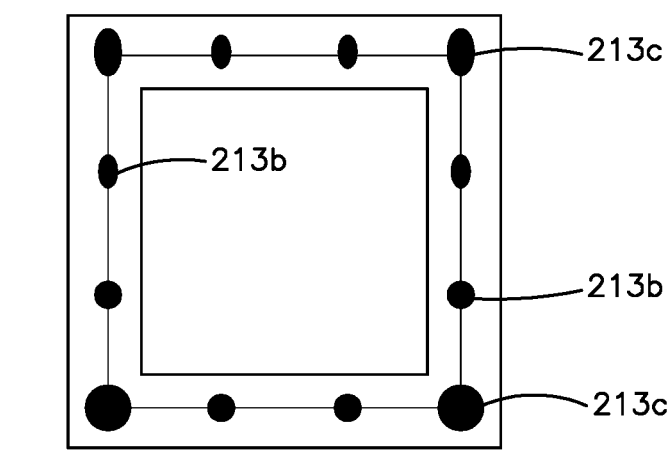
FIG. 4R depicts another array of fiducial markers.
Figure 4S:
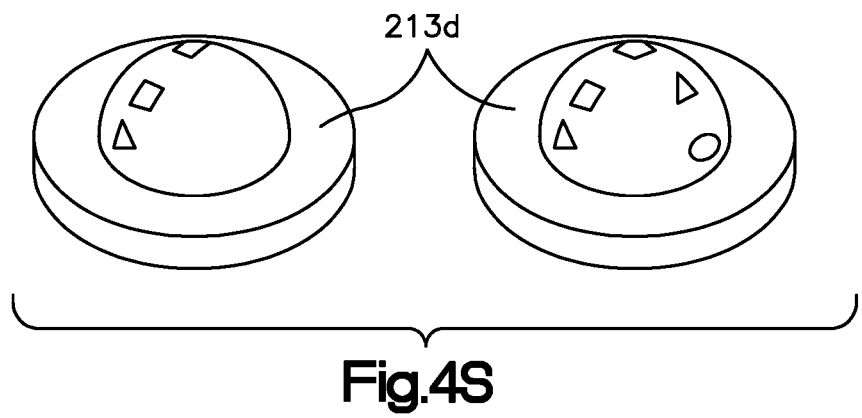
FIG. 4S depicts alternative fiducial markers.
Figures 4T, 4U, 4V:
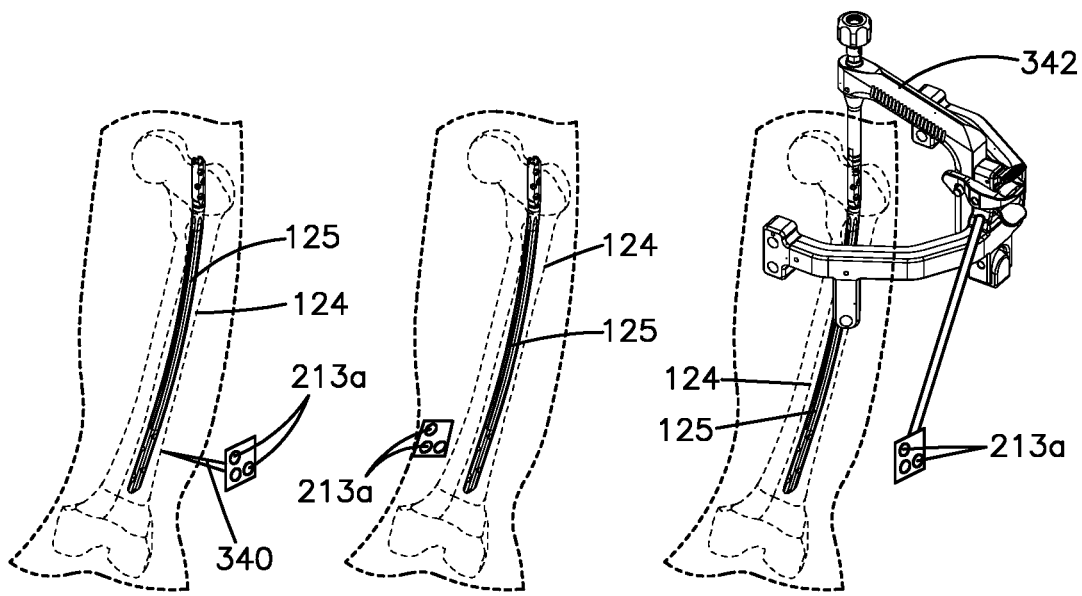
FIG. 4T depicts a perspective view of the array of fiducial markers fixed relative to the anatomical structure and the implant of FIG. 4D with a stake.
FIG. 4U depicts a perspective view of the array of fiducial markers fixed relative to the anatomical structure and the implant of FIG. 4D by sticking to the patient's skin.
FIG. 4V depicts a perspective view of the array fiducial markers fixed relative to the anatomical structure and the implant of FIG. 4D via a jig.

In an embodiment exemplified in FIG. 4T, the array of fiducial markers 213a is fixed relative to the anatomical structure 124 and the implant 125 with a stake 340. In an embodiment exemplified in FIG. 4V, the array fiducial markers 213a is fixed relative to the anatomical structure 124 and the implant 125 via a jig 342 that is attached to the implant 125 and extends externally of the anatomical structure 124.

In the illustrated embodiment in FIGS. 4D, 4P, and 4Q, for example, fiducial markers are ArUco markers. In some embodiments, other fiducial markers are provided instead of the ArUco markers to determine pose and distance. For example, an array of small rounded markers 213b and large rounded markers 213c may be provided in a rectangular pattern, as exemplified in FIG. 4R. In another embodiment, one or more spherical fiducials 213d, as exemplified in FIG. 4S, may be fixed relative to the patient. The spherical shape may provide for improved detection of the fiducial markers, for example, when arranged on a curved surface and/or the fiducial markers 213d are detected at different angles of projection.

Regardless of the fiducial marker used, each individual fiducial marker and/or the array of fiducial markers may be visually recognizable by the image sensor 209 to determine pose and distance relative to the image sensor 209. In an embodiment, the circular fiducial markers may be colored and/or have different diameters to distinguish features of the pattern to determined pose and distance. Different coloring of the markers may provide for quick identification of an area of interest, which can be focused on to decrease the amount of image data that must be processed.

The fiducial markers 213 may be individually recognizable or as an array recognizable when placed onto a curved surface. For example, when placed on the patient's skin as exemplified in FIGS. 4U and 4W-4Z. The distortion caused to the shapes and relative distances of the fiducial markers 213a may be detected by the image sensor 209. A curvature of the fiducial markers 213a may be determined based on detected distortion. The pose of the fiducial markers may be determined in part based on the curvature. For example, the pose of the fiducial markers 213a may be determined at least in part based on the detected curvature from one or more viewpoints exemplified in each of FIGS. 4W-4Z. In an embodiment, the X-ray image data may include the curvature and/or relative distance of the fiducial markers from more than one viewpoint (e.g., of the viewpoints exemplified in FIGS. 4W-4Z.

Referring now to FIGS. 4W-4Z, the image sensor 209 may generate image data representing multiple viewpoints and including fiducial markers 213a that are not represented in the X-ray image data. For example, one or more of the fiducial markers 213a may be radiopaque and represented in a single X-ray image generated by the medical imaging device 104 (shown in FIG. 1). The orientation and/or position of each radiopaque marker 213a relative to the desired trajectory (e.g., a central axis of a hole of the implant and/or a hole of an anatomical structure) may be determined in the same manner discussed above with reference to FIG. 8. The viewpoints may be perpendicular to one another such that navigation guidance may be provided for two perpendicular planes based on a single 2D X-ray image (i.e., a snapshot).

Multiple images representing different viewpoints from the image sensor 209 may be daisy-chained to determine the orientation and/or position of fiducial markers 213a, relative to the desired trajectory, that are not represented in the X-ray image data. Fiducial markers 213a that are not detected by the medical imaging device 104 (e.g., fiducial markers 213a that are not radiopaque or otherwise not detectable by the medical imaging device 104 from its viewpoint when the single X-ray image is generated) may be detected by the image sensor 209. For example, the lowest and highest fiducial markers 213a when viewing FIG. 4W and the highest fiducial markers 213a when viewing FIGS. 4X-4Z, respectively, may not be radiopaque. The image sensor 209 may detect each of the fiducial markers 213a that are not radiopaque by generating image data from multiple different viewpoints relative to the fiducial markers 213a (e.g., from the viewpoints shown in FIGS. 4W-4Z).

Figures 4W, 4X, 4Y, 4Z:
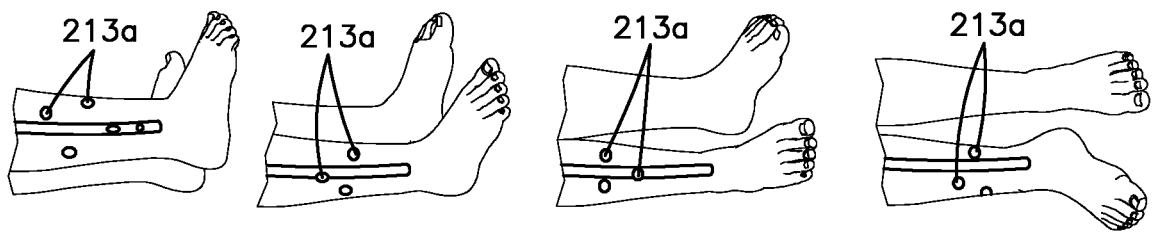
FIG. 4W depicts a perspective view of a first portion of another array of fiducial markers, an anatomical structure, and an implant.
FIG. 4X depicts a perspective view of a second portion of the array of fiducial markers, the anatomical structure, and the implant of FIG. 4W.
FIG. 4Y depicts a perspective view of a third portion of the array of fiducial markers, the anatomical structure, and the implant of FIG. 4W.
FIG. 4Z depicts a perspective view of a fourth portion of the array of fiducial markers, the anatomical structure, and the implant of FIG. 4W.

With respect to FIG. 4W, the pose of the non-radiopaque fiducial markers 213a, that are represented along with the radiopaque fiducial marker 213a (e.g., the fiducial marker 213a between the lowest and highest fiducial markers 213a in FIG. 4W), may be determined based on the image sensor data representing the fiducial markers 213a in FIG. 4W and the single X-ray image generated by the medical imaging device 104. For example, the pose of the non-radiopaque fiducial markers 213a, relative to the desired trajectory, may be determined based on the detected pose of the radiopaque fiducial marker 213a. Turning to FIG. 4X, the pose of the uppermost non-radiopaque fiducial maker 213a relative to the desired trajectory may be determined based on the determined pose of the uppermost non-radiopaque fiducial marker 213a in FIG. 4W. Turning to FIG. 4Y, the pose of the uppermost non-radiopaque fiducial maker 213a relative to the desired trajectory may be determined based on the determined pose of the uppermost non-radiopaque fiducial marker 213a in FIG. 4X. Turning to FIG. 4Z, the pose of the uppermost non-radiopaque fiducial maker 213a relative to the desired trajectory may be determined based on the determined pose of the uppermost non-radiopaque fiducial marker 213a in FIG. 4Y.

In some embodiments, image sensor generates images from the different viewpoints in a different order. For example, the image sensor may generate image data representing the viewpoint in FIG. 4Z before generating image data representing the viewpoint in FIG. 4X or the viewpoint in FIG. 4Y. For example, the pose of the of the non-radiopaque fiducial markers 213a shown in FIG. 4Z relative to one another may be determined before determining the relative pose of the non-radiopaque fiducial markers shown in FIG. 4X or 4Y.

The fiducial markers 213 may be made by cutting or machining metal, printing the pattern with radiopaque ink, and/or filling in a cavity with curable radiopaque material. The radiopaque component of the fiducial markers 213 may be relatively thin, less than 0.3 mm.

The fiducial markers 213 may each have an area of anywhere from 25 mm to 2,500 mm. For example, the fiducial markers 213 may have a square outer periphery with the sides of each fiducial marker 213 having a length of anywhere from 5 mm to 50 mm. In some embodiments, the fiducial markers may each have an area of 400 mm to 625 mm (e.g., with lengths of anywhere from 20 mm to 25 mm). In an embodiment, the fiducial markers each have a square outer periphery and have sides having a length of about 23 mm (i.e., an area of about 529 mm).

Fiducial markers with relatively large sizes may impact the ability of the C-arm and/or the image sensor 209 to accurately detect the pattern of the fiducial markers. For example, the size may be limited by the anatomical space around the surgical site (e.g., locking site for the IM nail). Larger sizes may limit the quantities of markers that can be placed within the field of view of the C-arm and/or the image sensor 209, may obstruct the surgeon's view or range of movement, and/or may be more difficult to adhere securely to the patient's skin.

In an embodiment, a single fiducial marker is provided for detection by the C-arm and the image sensor 209. One fiducial marker may be sufficient to determine the pose of the fiducial marker in the X-ray image generated by the C-arm and in the image sensor image generated by the image sensor 209. In some embodiments, more than one fiducial marker is provided. For example, at least three fiducial markers may be provided for detection by the C-arm and the image sensor 209. Detecting three fiducial markers may result in higher accuracy than when fewer fiducial markers are detected. In some embodiments, at least four fiducial marks are provided. Detecting four fiducial markers may result in higher accuracy than when fewer fiducial markers are detected.

Figure 7:
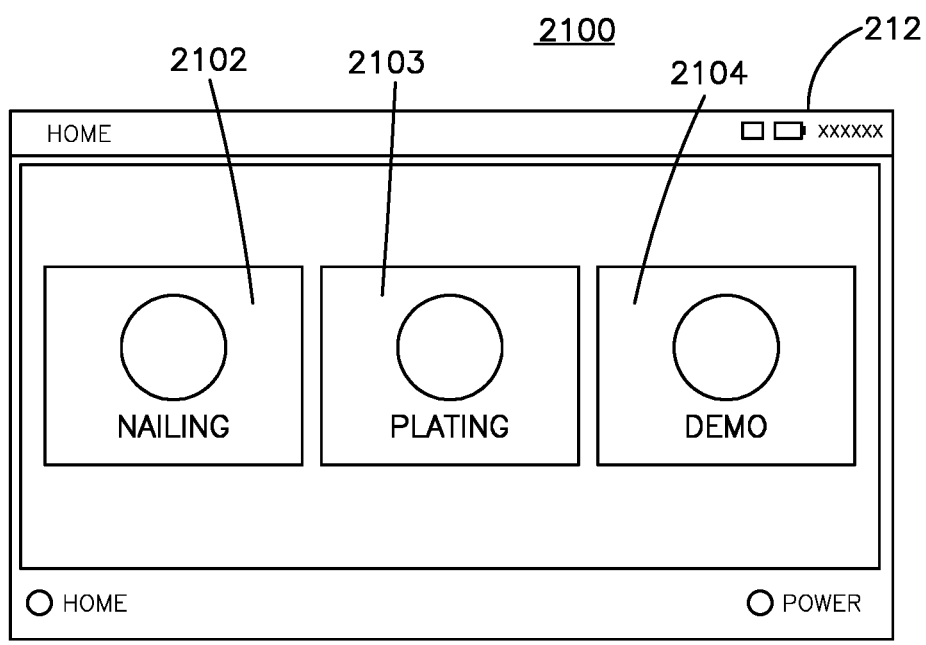
FIG. 7 is another example screen shot of the display of the surgical instrument assembly, wherein the screen shot includes options for performing different operations.

Referring to FIG. 7, a user may select one or more operations by inputting an option on an example a user interface 2100, which can be displayed by the display 212. For example, the user can select an IM trajectory option 2104 to perform IM drilling operations. The user can select a plating option 2103 to perform operations associated with securing a plate to a bone. The user can select a nailing option 2102 to perform operations associated with securing a nail with a distal locking screw. It will be understood that alternative or additional options may be rendered by the user interface 2100 as desired. Further, it will be understood that the inputting of the options may result in further displays being rendered, so as to guide the user through a particular operation.

Referring generally to FIGS. 2A-D and 13, the surgical instrument assembly 202 that can include the computing device 204 mounted to a surgical instrument 203. The surgical instrument 203 can be configured to operate on the anatomical structure 124 (shown in FIG. 4A).

The surgical instrument 203 can define a body 205, and the computing device 204 can be attached anywhere to the body 205 as desired. In an example, referring to FIGS. 2A-D, the computing device 204, and the display 212, can be supported by a mount 228. The mount 228 may be attachable to the attachment member 218. For example, the attachment member may include a rotatable base 230 that the mount 228 is attachable to (e.g., via a bolted connection). In some embodiments, the computing device 204 permanently attached to the surgical instrument.

The rotatable base 230 may be configured to remain in a fixed position regardless of the orentation of the surgical instrument 203, unless rotated by a user. In an embodiment, the rotatable base may be configured to be locked in a desired position.

While the surgical instrument 203 is depicted as a surgical drill for purposes of example, it will be appreciated that the computing device 204 can be removably attached to or permanently attached to other suitable equipment or instruments. For example, the surgical instrument assembly 202 may include an instrument or equipment configured to target an area of bone or other part of the anatomy, remove a medical implant, perform an osteotomy, or any other procedure, for instance any other procedure (e.g., using a combination of fluoroscopy and image sensor images), as desired. Thus, although the anatomical structure 124 is presented as a bone, it will be understood that structures on which the surgical instrument assembly can be configured to operate are not limited to bones.

The computing device 204 can include the display 212 that can be attached to the surgical instrument 203. The display 212 can be configured to display representations of the anatomical structure 124 (e.g., based on fluoroscopic data generated by the imaging device 104 and/or image sensor data generated by the image sensor 209). In an example configuration, the display 212 can display representations of the anatomical structure 124 in real-time, such that the representations of the anatomical structure 124 are displayed by the display 212 at the same time that corresponding image sensor data is generated by the image sensor 209 and/or that images are generated by the imaging device 104. In some embodiments, the display can include a plurality of displays, for instance a first display and a second display that has a different orientation as compared to an orientation of the first display.

Referring also to FIGS. 4A-4D, a representation of the anatomical structure 124 can include one or more target locations 126. The target locations 126 may represent locations on the anatomical structure 124 that the surgical instrument 203 can drill, cut, or otherwise target. In accordance with the illustrated example, the target locations 126 can be defined by an implant 125, for instance an IM nail or rod, in a bone. It will be understood that an example operation performed by the surgical instrument assembly is presented as an IM nailing operation to facilitate description of the disclosed subject matter, and the example IM operation is not intended to limit the scope of this disclosure. Thus, it will be appreciated that the surgical instrument assembly 202 may be used to perform other operations in addition to, or instead of, an operation such as the example IM nailing operation.

With reference to FIG. 4D, an array of fiducial markers 213a may be arranged in rectangular pattern about one or more of the target locations 126. As exemplified in FIG. 4D, the target locations 126 may be depicted as extending directly into the page when viewing FIG. 4D. The view that FIG. 4D represents may be referred to as being aligned with perfect circle. When the target locations 126 are cylindrical through holes, for example, the X-ray image aligned with perfect circle represents the target locations 126 as perfect circles.

The computing device 104 may receive the such perfect circle X-ray image and determine a world coordinate system 220. For example, the computing device 104 may determine the orientation of each fiducial marker 213a of the array of fiducial markers 213a and from such determine the world coordinate system 220 based on the X-ray image. The world coordinate system 220 may include a $X_1$-Axis, a $Y_1$-axis, and a $Z_1$-axis that are each perpendicular to one another and fixed relative to the array of fiducial markers 213a.

The world coordinate system 220 may be defined by a corner of the array of fiducial markers 213a. The $X_1$-Axis may extend along one side (e.g., a bottom side) of the rectangular array of fiducial markers 213a, the anatomical structure 124, and the implant 125. The $Y_1$-axis may extend along another side (e.g., a left side) of the rectangular array of fiducial markers 213a. The $Z_1$-axis may extend away from a corner of the rectangular array of fiducial markers 213a.

The computing device 104 may determine an image sensor coordinate system 222 based on the image sensor data. For example, the image sensor coordinate system 222 may include a $X_2$-Axis, a $Y_2$-axis, and a $Z_2$-axis that are each perpendicular to one another and determined based on the image sensor data. The image sensor coordinate system 222 may be fixed relative to array of fiducial markers 213a, the anatomical structure 124, and the implant 125. For example, $Z_2$-axis may be centered at one of the target locations 126 an $X_2$-Axis may extend along a length of the implant 125. The $Z_2$-axis may extend radially away from the center of the target location 126. A desired trajectory may extend along the $Z_2$ axis to the center of the opening of the target location 126.

In real time, the computing device 104 may determine a transformation matrix to determine orientations and/or positions of objects detected in the X-ray image in relation to objects detected in the image sensor data. For example, the computing device 104 may determine a real time pose of the surgical instrument 203 (e.g., the drill bit 226 of the surgical instrument 204) in the camera coordinate system 222 based on the real time image sensor data. The computing device 104 may use the transformation matrix in real time to determine the real time pose of the surgical instrument 203, including the drill bit 226, in the world coordinate system 220. The computing system 104 may determine the pose of the surgical instrument 203 relative to the target location 126, for example, based on the determined world coordinates of the surgical instrument 203.

The pose drill bit 226 and the drill tip 226a relative to the target location 126 may be determined by the computing system 104 in substantially the same manner described above.

In an embodiment, image sensor coordinate system may be fixed relative to the image sensor.

Turning to FIGS. 4E-4I, a non-perfect circle X-ray image of the implant 125 is illustrated and shown at various steps of processing to determine coordinates of the target location 126. FIG. 4E exemplifies an initial X-ray image of the implant 125 along with the array of fiducial markers 213a. The X-ray image may be adjusted, for example, the brightness, contract, and/or noise may be adjusted to more clearly identify the implant 125 and/or the fiducial markers 213a, for example.

The adjustment may result in an adjusted X-ray image exemplified in FIG. 4F. A portion of the X-ray image illustrated in FIG. 4F may be cropped so that the computing device 204 may focus on the area near the target location 126, for example, as exemplified in FIG. 4G. As shown in FIG. 4H, the computing device 204 may determine the world coordinate system 220 based on the cropped X-ray image in FIG. 4G. As discussed further below, the computing device 104 may determine the pose of the target location 126 based on the shape of the target location 126 depicted in the FIG. 4G or 4H in relation to the world coordinate system 220. The $X_1$-Axis, the $Y_1$-axis, and the $Z_1$-axis coordinates (e.g., true 3D coordinates) of the target location 126 (e.g., a center of the opening of the target location 126) in relation to the world coordinate system 220 may be determined by the computing system 104.

Turning to FIGS. 4J-4O, a perfect circle X-ray image of the implant 125 is illustrated and shown at various steps of processing to determine coordinates of the target location 126. FIG. 4J exemplifies an initial X-ray image of the implant 125 along with the array of fiducial markers 213a. The X-ray image may be adjusted, for example, the brightness, contract, and/or noise may be adjusted to more clearly identify the implant 125 and/or the fiducial markers 213a, for example.

The adjustment may result in an adjusted X-ray image exemplified in FIG. 4K. A portion of the X-ray image illustrated in FIG. 4K may be cropped so that the computing device 204 may focus on the area near the target location 126, for example, as exemplified in FIG. 4L. As shown in FIG. 4M, the computing device 204 may determine the world coordinate system 220 based on the cropped X-ray image in FIG. 4L. As discussed further below, the computing device 104 may determine the location of the target location 126 relative to the fiducial markers 213a depicted in FIG. 4M, for example.

As exemplified in FIG. 4N, a cylinder method may be used to determine a position of a center, for example, of an opening of the target location 126 to determine the $X_1$-Axis and $Y_1$-axis coordinates of the target location in relation to the world coordinate system. The desired trajectory for drilling may extend along a central axis of the cylinder.

As discussed above in relation to FIG. 4I and as exemplified in FIG. O, the computing system 204 may determine a depth of the target location 126 based on a detected contour of the target location 126. Thus, the $X_1$-Axis, the $Y_1$-axis, and the $Z_1$-axis coordinates (e.g., true 3D coordinates) of the target location 126 in relation to the world coordinate system 220 may be determined by the computing system 104.

The display 212 can display representations of fluoroscopic images associated with IM nailing operations, among others. Further, the display 212 can display images or data associated with a depth of the drill bit 226. Further still, the display 212 can display images or data associated with the depth at the same time that the display 212 renders representations of fluoroscopic images of the anatomical structure 124.

The display 212 can be configured to display, for example, representation images 400a-400c of the anatomical structure 124, generated by, for example, the computing device 104 based on X-ray image data received from the medical imaging device 104 and image sensor data received from the image sensor 209. Referring in particular to FIG. 4A, the display 212 can display the representation image 400a of the implant 125 in the anatomical structure 124. The implant 125 can define one or more target locations 126 at which material can be removed from the anatomical structure 124. In an example IM nailing operation, by viewing the display 212 that displays representation images based on the X-ray image data and the image sensor data, a medical professional can maneuver the patient or the surgical instrument 203 while viewing the patient and display 212 simultaneously, until the drill bit tip 226a is located at a desired entry point of the paint (e.g., as shown in FIG. 4C). In the IM nailing example, when the drill bit tip 226a is centered over the respective target location 126, the drill bit tip 226a may be at the proper entry point for locking screws.

Referring now to FIG. 4B, the display 212 can display the representation image 400b of the implant 125 and the anatomical structure 124. Thus, the display 212 can be configured to display a representation of a position of the cutting tip 226a of the cutting instrument 226 relative to the target location 126. The representation image 400b can depict, for example, the position of the cutting tip 226a that is shown in FIG. 6B.

The cutting tip 226a can be configured to remove anatomical material from the one or more target locations 126 of the anatomical structure 124. Further, as shown in FIG. 4C, the tip 226a of the cutting instrument 226 (e.g., drill bit) can be positioned on the anatomical structure 124, for instance at the center of the target location 126. The display 212 can be positioned so as to provide a line of sight to both the tip 226a and the display 212 from a location proximate of the surgical instrument 203, such that a medical professional can view both the representation images 400b and 400c, the tip 226a, and the anatomical structure 124, so as to center the tip 226a at the target location 126.

In some embodiments, for instance based on a user selection via the user interface 216, the surgical instrument assembly 202 can rotate the displayed representation images 400a-400c on the display 212 to a rotated orientation such that a vertical or horizontal direction on the display 212 corresponds with a vertical or horizontal direction, respectively, of movement of the surgical instrument 203 relative to the anatomical structure 124. Thus, such representation images may be displayed as rotated relative to the actual position of the drill bit, the implant, and/or the anatomical structure.

Figure 5A:
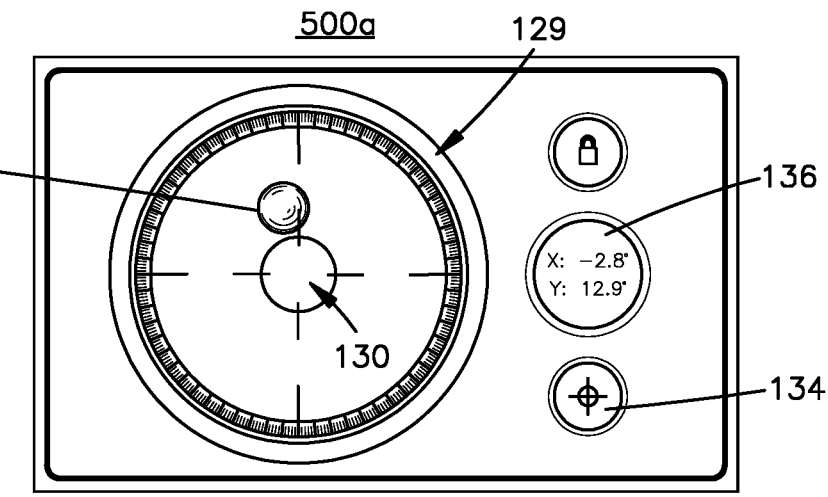
FIG. 5A depicts an example screen shot of the display of the surgical instrument assembly, showing a visual indication of an alignment of the cutting instrument with respect to the desired drilling trajectory, wherein the cutting instrument is out of alignment with respect to a first direction.
Figure 5B:
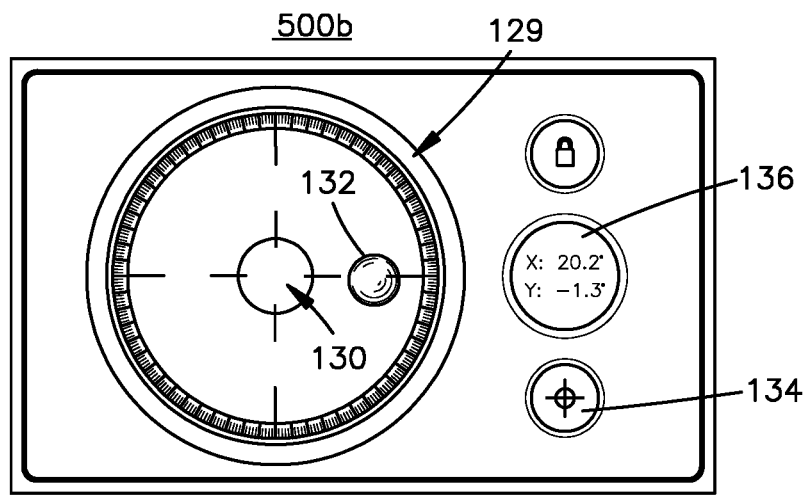
FIG. 5B depicts another example screen shot of the display of the surgical instrument assembly, showing the visual indication of the alignment of the cutting instrument with respect to the direction of X-ray travel, wherein the cutting instrument is out of alignment with the desired drilling trajectory with respect to a second direction that is substantially perpendicular to the first direction.
Figure 5C:
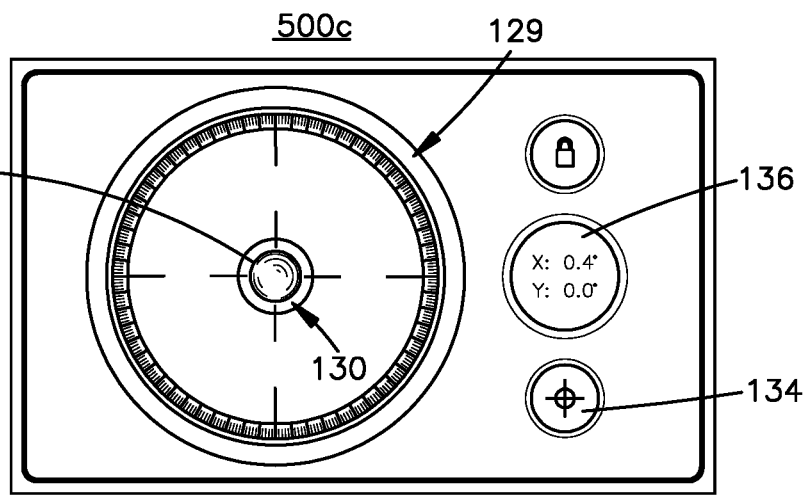
FIG. 5C depicts another example screen shot of the display of the surgical instrument assembly, showing the visual indication of the alignment of the cutting instrument with respect to the direction of X-ray travel, wherein the cutting instrument is aligned with the desired drilling trajectory such that the cutting instrument and the direction of desired drilling trajectory have the same orientation.

Referring now to FIGS. 5A-5C, the display 212 can also be configured to provide a visual indication, for instance an orientation image 129, of an alignment of the cutting tip 226a with respect to the desired trajectory (e.g., the central axis of the target hole 126) based on the X-ray image data and the image sensor data. In an example, the display 212 is configured to display the representation images 400a-400c in real time based on the image sensor data that is generated in real time by the image sensor 209, and is configured to simultaneously display the orientation screens (e.g., orientation screens 500a-500c) that include a visual indication of an orientation of the cutting instrument 226. In an embodiment, the display includes more than one display, each of which displays a different one of a representation image or an orientation screen.

In an embodiment, the user can select an option via the user interface 216 to select which of the representation images, orientation screens, or depth information are displayed by the display 212. In some embodiments, the display 212 can be separated, for instance split in half or split in thirds, such that any combination of the representation images, orientation screens, and depth information can be displayed by the display 212 at the same time. It will be understood that the examples described herein of images (e.g., FIGS. 4A-4C, 5A-5C, and 10A-20) that can be displayed by the display 212 are not exhaustive. The display 212 can provide a user with various information via a variety of arrangements or alternative visual depictions.

The visual indication of alignment, for instance the orientation image 129, can be based on real time image sensor data of an orientation of the drill bit 226 relative to the fiducial markers 213a (e.g., as shown in FIG. 4D). The visual indication of alignment may be further based on the desired trajectory relative to the fiducial markers 213a (e.g., the central axis of the target 126).

For example, referring to FIGS. 5A-5C, the orientation screens 500a-500c can include the orientation image 129 that can include a static region 130 and a movable indicator 132. The movable indicator 132 can be representative of the orientation of the cutting instrument 226. In an example, the cutting instrument 226 is oriented with the desired trajectory when the movable indicator 132 has a predetermined spatial relationship to the static region 130. In an example, a hole is drilled in the anatomical structure 124 while the tip 226a of the cutting instrument 226 (e.g., drill bit) is aligned with the target location 126, and the movable indicator 132 has the predetermined spatial relationship to the static region 130. It will be understood that the predetermined spatial relationship can vary as desired.

In some cases, for example, the cutting instrument 226 is oriented with the desired trajectory when the movable indicator 132 overlies the static region 130. As shown in FIG. 5C, for example, the cutting instrument 226 is oriented with the desired trajectory when the movable indicator 132 is within a boundary defined by the static region 130.

Turning to FIGS. 5D-5G, alternative alignment graphics are illustrated. For example, FIG. 5D illustrates circle 240 and arrow 242 visual indication of the alignment of the cutting instrument relative to the desired trajectory (and the target location 126). A bulls-eye 244 may represent an aligned orientation and the arrow 242 may guide a user to the aligned orientation. FIG. 5E illustrates a bubble level 246 visual representation, where a static center 248 represents an aligned orientation. FIG. 5F illustrates a pair of circles 250, 252 that may each represent a different portion of the drill bit 226 relative to the target location 126. When each circle 250, 252 is centered on the target location 126, the drill bit 226 may be aligned. FIG. 5G illustrates a movable dot 254 that moves, with the orientation of the drill bit 226, relative to a static dot 256. The movable dot 254 being centered on the static dot 256 may indicate the drill bit 226 is aligned with the target location.

In an embodiment, when the drill bit tip is located within a predetermined distance from the center of the target 126, the center of the static region target may change color. For example, the center of the static region may turn green. When both the drill bit tip and the alignment of the drill bit axis are within a predetermined range, the outline of the display may change color. For example, the outline of the display may turn green.

As described above with reference to FIGS. 4A-4C, the display 212 can display representation images 400a-400c and user interfaces associated with placing locking screws to secure an IM nail. Referring now to FIGS. 13 to 20, the display 212 can additionally, or alternatively, display representation images and user interfaces associated with placing the implant 125, for instance an IM nail. The display 212 can be configured to display representation images based on the image sensor data in combination with the orientation of a desired trajectory relative to the fiducial markers 213a, which are fixed relative to the anatomical structure 124 in a manner discussed above. For example, representation image 602 (FIGS. 13, 14A, 14B), representation image 604 (FIG. 15), representation image 606 (FIG. 16), representation image 608 (FIG. 17), representation image 610 (FIG. 18), and representation images 630a and 630b (FIG. 20).

Figure 14A:
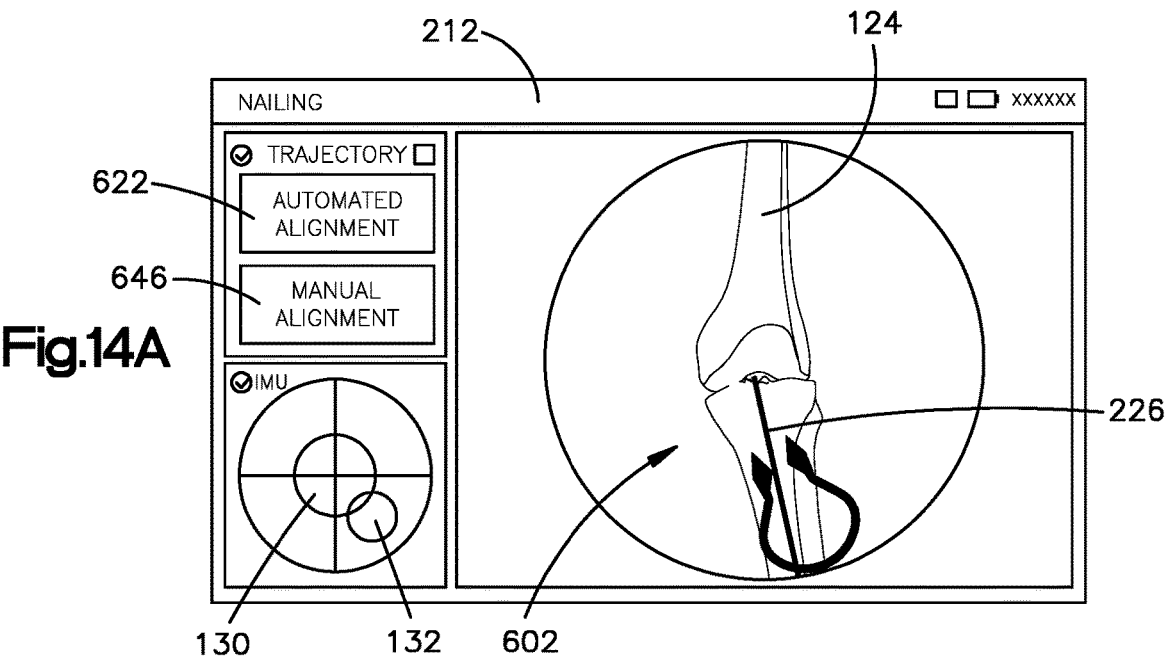
FIG. 14A is an example screen shot of the display of the surgical instrument assembly, showing representative of the anatomical structure from a first or an anteroposterior (AP) view, wherein the representation includes the cutting instrument positioned to enter the anatomical structure for a specific intramedullary (IM) nailing procedure.

As used herein, unless otherwise specified, X-ray image data and X-ray image can be used interchangeably, without limitation. Referring in particular to FIG. 14A, the display 212 can display the representation image 602 of the anatomical structure 124 (e.g., a representation of X-ray image data of the anatomical structure). In accordance with the illustrated example, the representation image 602 may include a representation of the cutting instrument 226 in real time relative to the representation of the anatomical structure 124 (e.g., based on the real time image sensor data that is based on the orientation of the fiducial markers 213a relative to the image sensor 209). The cutting instrument 226 as represented in FIG. 14A may be positioned to drill a hole in the anatomical structure 224 for the implant 125.

In an example, a hole can be drilled so as to meet the IM canal of the anatomical structure or bone 124. Thus, the hole can define a point of entry into the bone and a trajectory between the point of entry and the IM canal, and the implant 125, for instance an IM nail or rod, can be inserted into the hole that is sized so as to receive the implant 125. It is recognized herein that the desired trajectory (also referred to herein as an "appropriate trajectory") and point of entry (e.g., to minimize pain) of the drilling operation can vary depending on the type of bone and/or the implant that is to be inserted. It is further recognized herein that the appropriate trajectory and point of entry might not be readily accessible in a given operating room, so that a given medical professional might rely on personal knowledge to estimate the appropriate trajectory and point of entry. Further still, even if the appropriate trajectory and point of entry are known, the drilling operation is commonly performed freehand, such that the actual trajectory and point of entry can vary from the appropriate trajectory and point of entry.

Figure 14B:
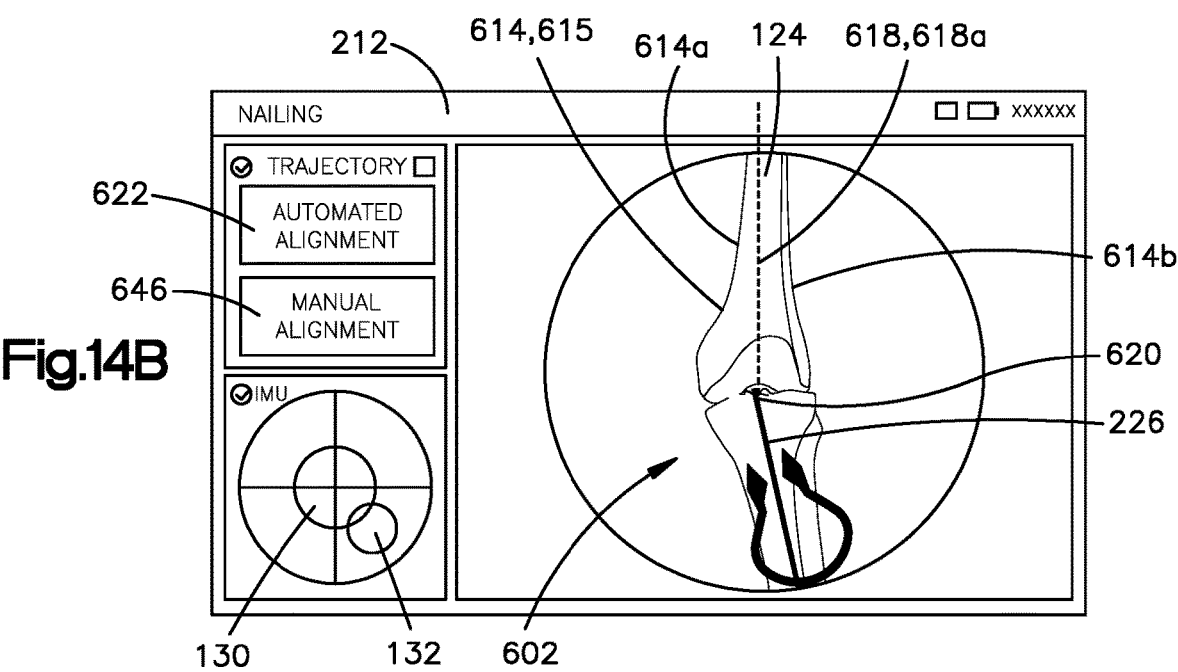
FIG. 14B is an example screen shot of the display of the surgical instrument assembly, wherein the screen shot includes the representation of FIG. 14A with an AP boundary and an AP representation of the desired trajectory for the specific IM nailing procedure overlayed on the representation of the anatomical structure.
Figure 17:
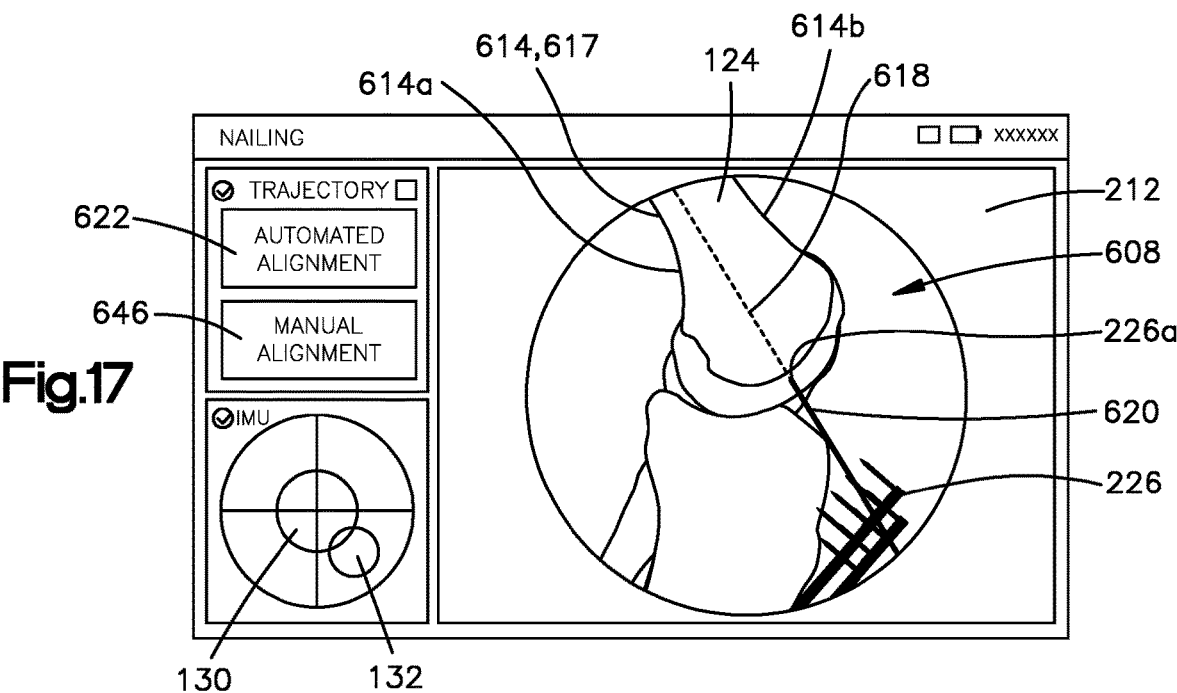
FIG. 17 is an example screen shot of the display of the surgical instrument assembly, wherein the screen shot includes the representations of FIG. 16 but with the position of the cutting instrument adjusted in accordance with the lateral representation of the desired trajectory.

In an example embodiment, referring to FIGS. 14B and 17, the processor of the surgical instrument assembly 202 can identify or determine a boundary 614, for instance a first or anteroposterior (AP) boundary 615 (FIGS. 14B and 15), or a second or lateral boundary 617 (FIGS. 16 and 17), of the anatomical structure 124. The boundary 614 can define a first outermost edge 614a of the anatomical structure 124 and a second outermost edge 614b of the anatomical structure 124 opposite the first outermost edge 614a. In some examples, the processor can determine the boundary 614 by performing an edge detection process that is described in U.S. Patent Application Publication No. 2007/0274584 published Nov. 29, 2007 and entitled "Method and System for Detection of Bone Fractures," the disclosure of which is incorporated by reference as if set forth in its entirety herein.

It will be understood that other edge detection algorithms may be performed as desired, and the edge detection processes mentioned above are presented for purposes of example. In some cases, the processor can identify the boundary 614 based on a user selection via the user interface 216. For example, the display 212 can display an option, such as a manual alignment option 646. The user, for instance a medical professional, can actuate the manual alignment option 646, for instance by touch or the like. When the manual alignment option 646 is actuated, the user can manually overlay one or more images (e.g., a longitudinal axis 618 of the anatomical structure 124) on the representation image 602, such that the display 212 displays the one or more images on the representation image.

An example of an image that the user can manually overlay is the boundary 614. By way of example, users can use a stylus, finger, or the like to manually overlay images on the X-ray data. In an example, the user can actuate the manual alignment option 646 to adjust the boundary 614 that is determined by the processing unit 206 of the surgical instrument assembly 202. For example, the processing unit 206 can perform an edge detection process to determine the boundary 614, but in some cases, the edge detection process can result in portions of the boundary 614 that are offset from the actual outermost edge of the anatomical structure 124. For instance, the edge detection process might incorrectly identify a fracture in the anatomical structure 124 as a portion of the boundary 614. In the example, the user can, via the user interface 216, adjust the portion of the boundary 614 that is incorrectly identified as representing an outermost edge of the anatomical structure 124. Thus, the surgical instrument assembly 202 can adjust at least a portion, for instance all, of the boundary 614 in response to the user actuating at least one of the options of the user interface 216.

Figure 18:
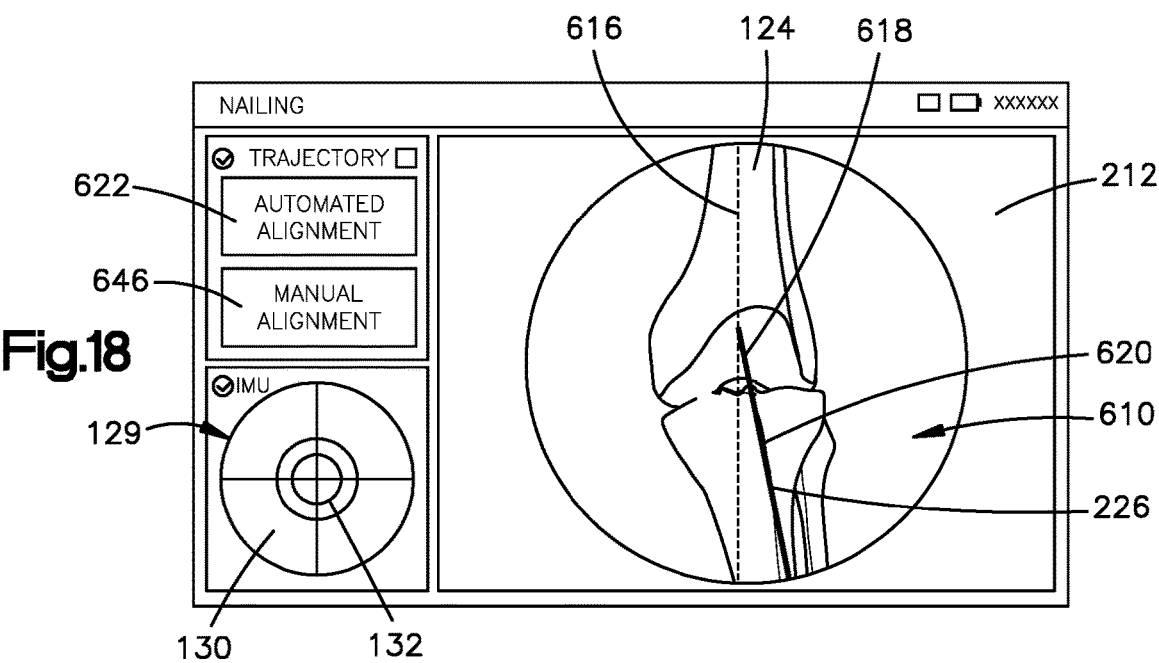
FIG. 18 is another example screen shot of the display of the surgical instrument assembly, wherein the screen shot includes 1) a representation of an anatomical structure; 2) an axis of the anatomical structure overlaying the representation of the anatomical structure; and a representation of another desired trajectory overlaying the representation of the anatomical structure, wherein the representation of the desired trajectory is offset at an angle relative to the axis.

As shown in FIGS. 14B, 15, 16, and 17, the display 212 can overlay the boundary 614 on the representation images of the anatomical structure 124, so as to display the boundaries 614 of the anatomical structure 124. Referring to FIGS. 18 and 20, the processing unit 206 of the surgical instrument assembly 202 can determine an axis 616 of the anatomical structure 124. The processing unit 206 of the surgical instrument assembly 202 can determine a representation of a trajectory 618 that defines a point of entry 620 into the anatomical structure. Referring to FIGS. 14B-18 and 20, the display 212 can overlay the representation of the trajectory 618 on the representation images of the anatomical structure 124, so as to display the representation of the trajectory 618 relative to the anatomical structure 124. The representation of the trajectory 618 can define a line along which a hole can be drilled so as to meet the IM canal of the anatomical structure 124.

The representation of the trajectory 618 can be determined based X-ray image data of the anatomical structure 124. For example, processing unit 206 may determine the trajectory 618 relative to the anatomical structure and the fiducial markers 213a.

Further, referring to FIGS. 18 and 20, the display 212 can overlay the axis 616 on the representation images 610, 630a, 630b of the anatomical structure 124, so as to display the axis 616 of the anatomical structure 124.

In some embodiments, the axis 616 may define a centerline along a length of the anatomical structure. Referring to FIGS. 14B-17, the trajectory can be coincident with the axis 616, such that the representation of the trajectory 618 and the axis 616 can overlap each other. For example, the first outermost edge 614a can be spaced from the second outermost edge 614b so as to define a width of the anatomical structure that is substantially perpendicular to the length of the anatomical structure. Thus, the axis 616 can be equidistant from the first outermost edge 614a and the second outermost edge 614b along the length of the anatomical structure 124. In some cases, the processing unit 206 can identify the axis 616 based on a user selection via the user interface 216. For example, the user, for instance a medical professional, can actuate the manual alignment option 646, for instance by touch or the like. When the manual alignment option 646 is actuated, the user can manually overlay one or more images on the X-ray data, such that the display 212 displays the one or more images on the X-ray data. An example of an image that the user can manually overlay is the axis 616. As shown, the axis 616 is represented as a dashed line, though it will be understood that that the axis 616 can be alternatively represented as desired, for instance by a solid line. By way of example, users can use a stylus, finger, or the like to manually overlay images on the X-ray data.

In an embodiment, the user can actuate the manual alignment option 646 to adjust the axis 616 that is determined by the processing unit 206 of the surgical instrument assembly 202 based on the boundary 614, in particular the first and second outermost edges 614a and 614b. Thus, the surgical instrument assembly 202 can adjust or determine at least a portion, for instance all, of the axis 616 in response to the user actuating at least one of the options of the user interface 216. Further, the surgical instrument assembly 202 can determine the axis 616 of the anatomical structure 124 based on the boundary 614 of the anatomical structure 124 such that, if the boundary 614 of the anatomical structure changes, the axis 616 of the anatomical structure 124 changes in accordance with the changes to the boundary 614. For example, the second outermost edge 614b is adjusted away from first outermost edge 614a, the surgical instrument assembly 202 can move the axis 616 toward the second outermost edge 614b, such that the axis 616 can be displayed farther away from the first outermost edge 614a as compared to where the axis 616 is displayed before the boundary 614 is adjusted.

The present disclosure provides embodiments that can lessen the number of X-ray images taken in an operating room, thereby decreasing the time it takes to perform a given operation. In some embodiments described above, only a single X-ray image may be taken before the surgeon begins surgery and is guided based on the real time image sensor data. In other embodiments, only two X-ray images may be taken before such surgery begins.

Figure 15:
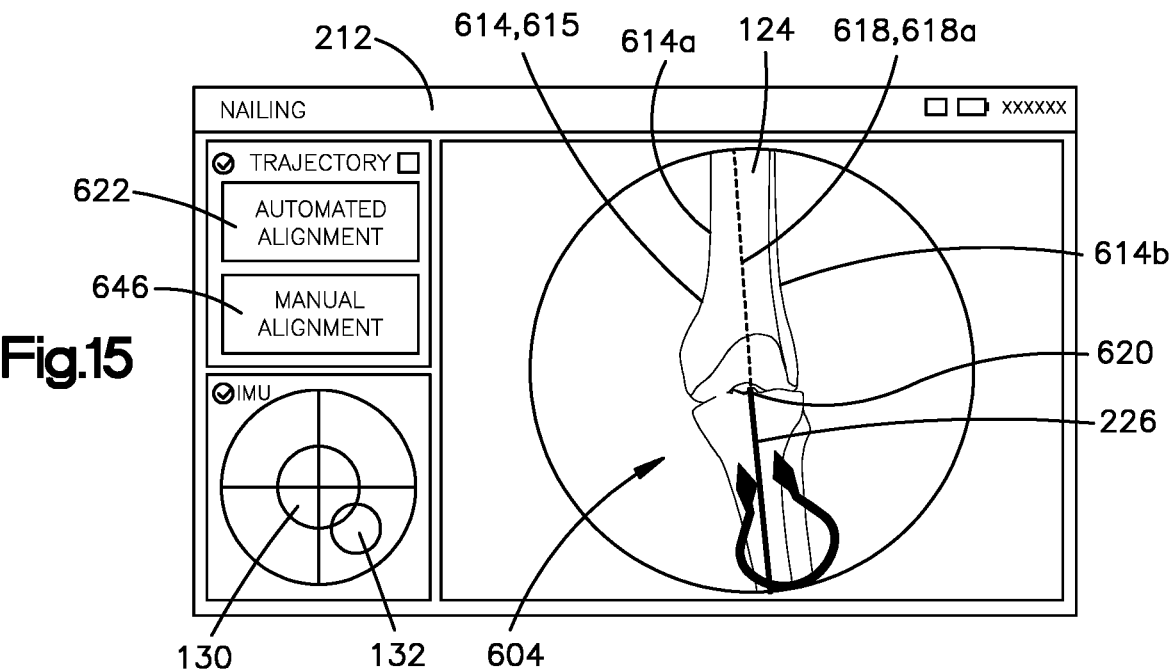
FIG. 15 is an example screen shot of the display of the surgical instrument assembly, wherein the screen shot includes the representations of FIG. 14B but with the position of the cutting instrument adjusted in accordance with the AP representation of the desired trajectory.
Figure 16:
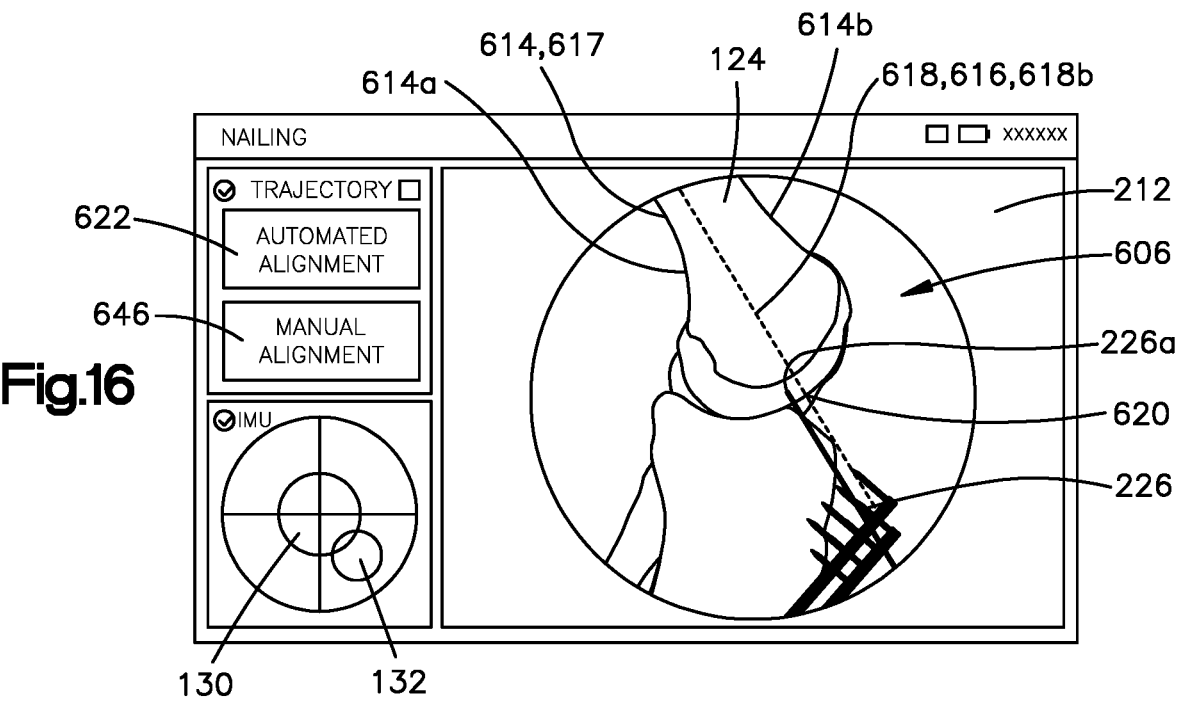
FIG. 16 is an example screen shot of the display of the surgical instrument assembly, showing a representation of the anatomical structure and the cutting instrument shown in FIG. 15, but from a second or lateral view instead of the AP view, wherein the screen shot includes the representation with a lateral boundary and a lateral representation of the desired trajectory for the specific IM nailing procedure overlayed on the representation of the anatomical structure.

In an example, with reference to FIGS. 14A-15 and representation image 630a in FIG. 20, the display 212 can display the representation of the anatomical structure 124 from a first or an anteroposterior (AP) view. The processing unit 206 can determine the representation of the trajectory 618 that defines the point of entry 620 into the anatomical structure 124. The display 212 can overlay the representation of the trajectory 618 on the representation image of the anatomical structure 124, so as to display the representation of the trajectory 618.

During use, the surgeon may indent or otherwise mark the patient's skin with the cutting instrument 225 at the point of entry (620) using the navigation based on the real time image sensor data. The surgeon may use another instrument to make an incision in the patient's skin to access the bone.

In an embodiment, the surgical instrument assembly may include a blade attached to the surgical instrument for making an incision to access the anatomical structure, while continually using the displayed navigation based on the real time image sensor data. In some embodiments, an incision tool includes a separate computer vision module that includes an incision image sensor that is configured to detect the fiducial markers and a blade of the incision tool in substantially the same manner as the image sensor described above with reference to FIG. 2A-2D. In an embodiment, the image sensor of the FIGS. 2A-2D may be configured to attach to the incision tool to detect the blade in substantially the same manner as the image sensor detects the cutting instrument. In some embodiments, the user may use the fiducial markers as landmarks to help visually inform their decision about where the incision should be made (e.g., when the X-ray image that the target hole is halfway between marker A and marker B the user may make an incision halfway between marker A and marker B).

When navigation is based on the image sensor data, the image sensor 209 may detect at least one fiducial marker 213a. The processing unit 206, for example, may determine the pose of each fiducial marker 213a within the world coordinate system.

For example, processor unit 206 may compare the detected pose of each fiducial marker 213a and compare such to the pose determined from the X-ray image data. If the location of any marker(s) 213a is outside a range of acceptable deviation (e.g., +/−0.5 mm), such marker(s) may not used for further processing or navigation steps. If sufficient markers are within the range of acceptable deviation, navigation processing may proceed or continue as usual, but without input based on the marker(s) that is outside the range of the acceptable deviation. If insufficient markers remain, the processing unit 206 may generate an alert that is provided to the user and may indicate mitigation options (e.g., by taking a new X-ray image, adjusting an orientation of the image sensor 209, and/or finishing the procedure freehand).

In an embodiment, the processing unit generates a visual alert, an audible alert, or some other feedback method to indicate to the user that the fiducial markers detected by the image sensor are no longer sufficient to provide accurate navigation. As an example, movement of any one of the fiducial markers detected by the image sensor relative to another may result in the processing unit generating the alert.

The processing unit 206 may perform a best fit algorithm to determine how the fiducial markers 213a as detected by the image sensor 209 match with a pre-determined object board. The processing unit 206 may execute a least squares algorithm to minimize re-projection error. If one or more fiducial markers 213a increase the error by more than a threshold amount, such fiducial markers 213a may be determined to have moved and as a result not included in further calculations based on the fiducial markers 213a. When the quantity of remaining (i.e., usable) fiducial markers is too low to provide accurate navigation, the processing unit 206 may generate an alert to indicate to the user to take mitigation steps. For example, the processing unit 206 may generate a visual or audible alert indicating that the user should replace the fiducial markers 213a and take a new X-ray image to generate new X-ray image data based on the newly placed fiducial makers. In some embodiments, one or more markers may be placed on a static surface, such as the OR table, to provide an immobile reference point for the markers attached to the patient.

The pose of the cutting instrument 226 may be determined in the world coordinate system based on the pose of the fiducial markers 213a detected by and relative to the image sensor 209. The processing unit 206 may determine, for example, the pose of the cutting instrument 226 in the world coordinate system based on the determined pose of the fiducial markers 213a in the world coordinate system and based on the pose of the cutting instrument 226 relative to the fiducial markers 213a that is detected by the image sensor 209. The processing unit 206 may determine in real time a distance from the cutting instrument 226 to the desired trajectory (e.g., an axis of the anatomical structure 124 or the implant 125) based on the real time image sensor data.

The navigational graphics discussed above may guide the user in real time to reduce the distance from the cutting instrument 226 and the desired trajectory. In an embodiment, the processing unit determines in real time a location of the drill tip and an axis of the cutting instrument in the world coordinate system based on the image sensor data. Thus, the processing unit may determine an orientation or position change to the cutting instrument that would align the cutting instrument with the desired trajectory. The processing unit may generate a display indicating to the user how to orient and/or position the cutting instrument to reach alignment, for example, as discussed above.

In an embodiment, only the drill tip of the cutting instrument is determined by the processing unit. The axis of the cutting instrument relative to the image sensor may be predetermined and/or the axis may be determined based on feedback data from the accelerometer of the surgical instrument assembly. In some embodiments, the orientation of the cutting instrument may be determined based on the image sensor data as a redundancy to double check the feedback data from the accelerometer, or visa versa.

During a drilling operation, the user may place the drill tip 226a on the bone and confirm based on the navigation graphics that the cutting instrument 226 is aligned with desired trajectory (e.g., represented as over the center of the target hole 126 and represented as at a desired angle relative to target hole 126 as shown in FIG. 18). If the cutting instrument 226 is oriented outside of a predetermined tolerance and/or positioned outside of a predetermined position (e.g., as exemplified in FIGS. 15 and 16), the navigational graphics may indicate to the user how to adjust the cutting instrument 226 to achieve alignment.

In some embodiments, the processing unit 206 can determine the representation of the trajectory 618 in response to a user's selection via the user interface 216. For example, the display 212 can display an option, such as an automated alignment option 622. The user, for instance a medical professional, can actuate the automated alignment option 622, for instance by touch or the like. When the automated alignment option 622 is input, the processing unit 206 of the surgical instrument assembly 202 can determine the representation of the trajectory 618 that defines the point of entry 620 into the anatomical structure 124. The surgical instrument assembly can also determine the axis 616 or the boundary 614, or both the axis 616 and the boundary 614, responsive to the automated alignment option 622 being input. Further, in response to the automated alignment option 622 being actuated, the display 212 can overlay at least one of, for instance only one of, for instance any combination of, the representation of the trajectory 618, the axis 616, and the boundary 614, on the representation images of the anatomical structure 124, so as to display the representation of the trajectory 618, the axis 616, and/or the boundary 614.

In some examples, the surgical instrument assembly 202 can determine the representation of the trajectory 618 based on technique information, for instance technique information stored in the memory 214. Such technique information can include appropriate trajectories for drilling a hole in various bones for placing an IM nail. Based on the technique information, the surgical instrument assembly 202 can determine the representation of the trajectory. By way of example, the technique information may stipulate that the trajectory for a given bone viewed from the AP perspective is 5 degrees lateral of an axis that is measured from a point just below the lesser trochanter. Continuing with the example, the technique information may stipulate that the trajectory for the given bone from the lateral perspective is centered in the greater trochanter and in line with the medullary canal. In an example, the type of bone and nail can be input into the processor via the user interface 216, and the view (e.g., lateral or AP) that corresponds to a representation of an anatomical structure can be input into the processor via the user interface 216. In response, the processor can retrieve technique information that corresponds to the view of the anatomical structure, the type of bone, and the nail. Based on the technique information that is retrieved, the trajectory can be determined. In some cases, the processor first determines the boundary 614, and then determines the axis 616 based on the boundary. The representation of the trajectory 618 can be determined based on the axis 616 and the technique information. For example, the technique information may indicate that that the trajectory is coincident with the axis 616 in a first view, and angularly offset from the axis by a specific angle in a second view that is substantially perpendicular to the first view (see FIG. 19).

Figure 19:
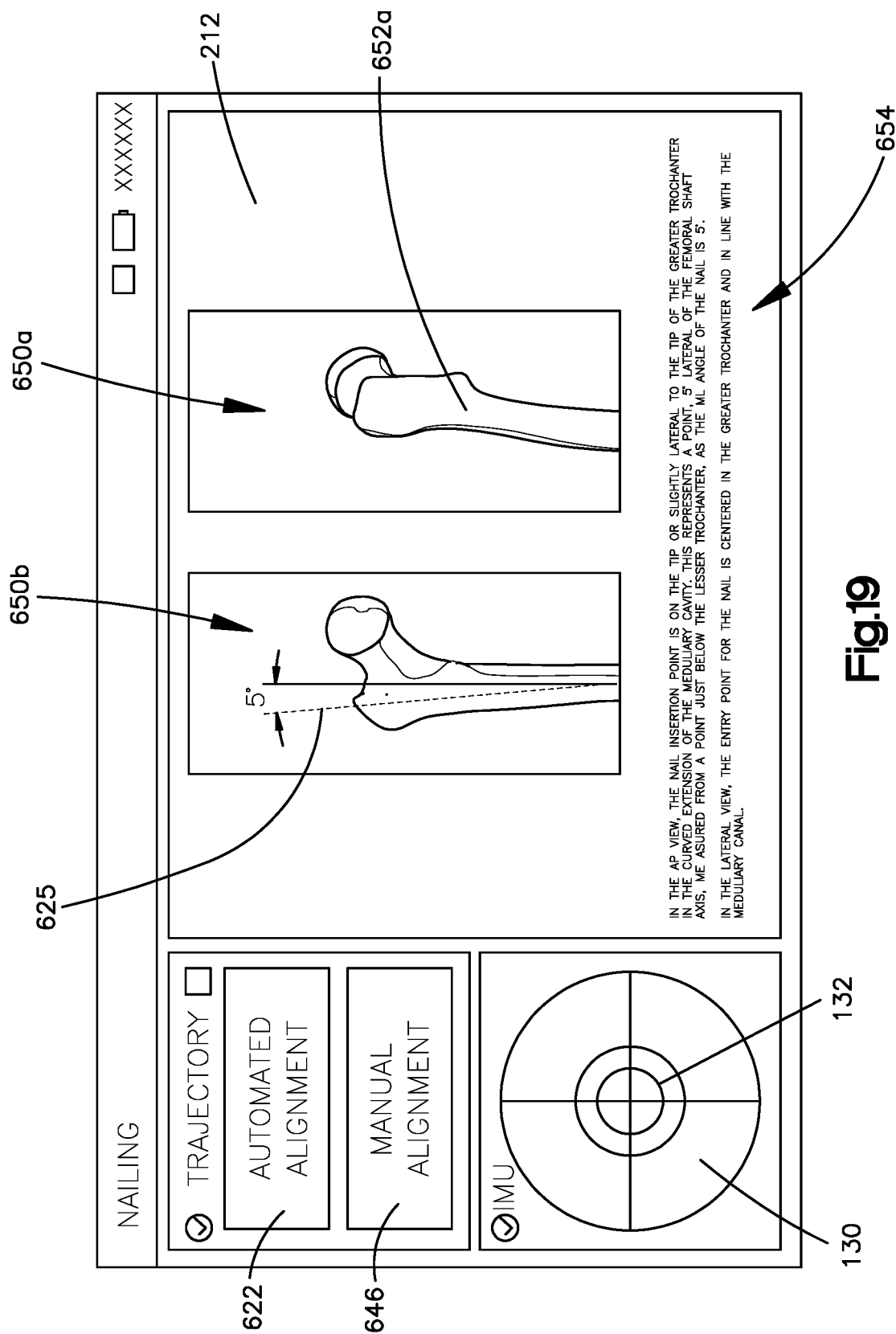
FIG. 19 is another example screenshot of the display of the surgical instrument assembly, showing example technique information associated with an IM nailing procedure.
Figure 20:
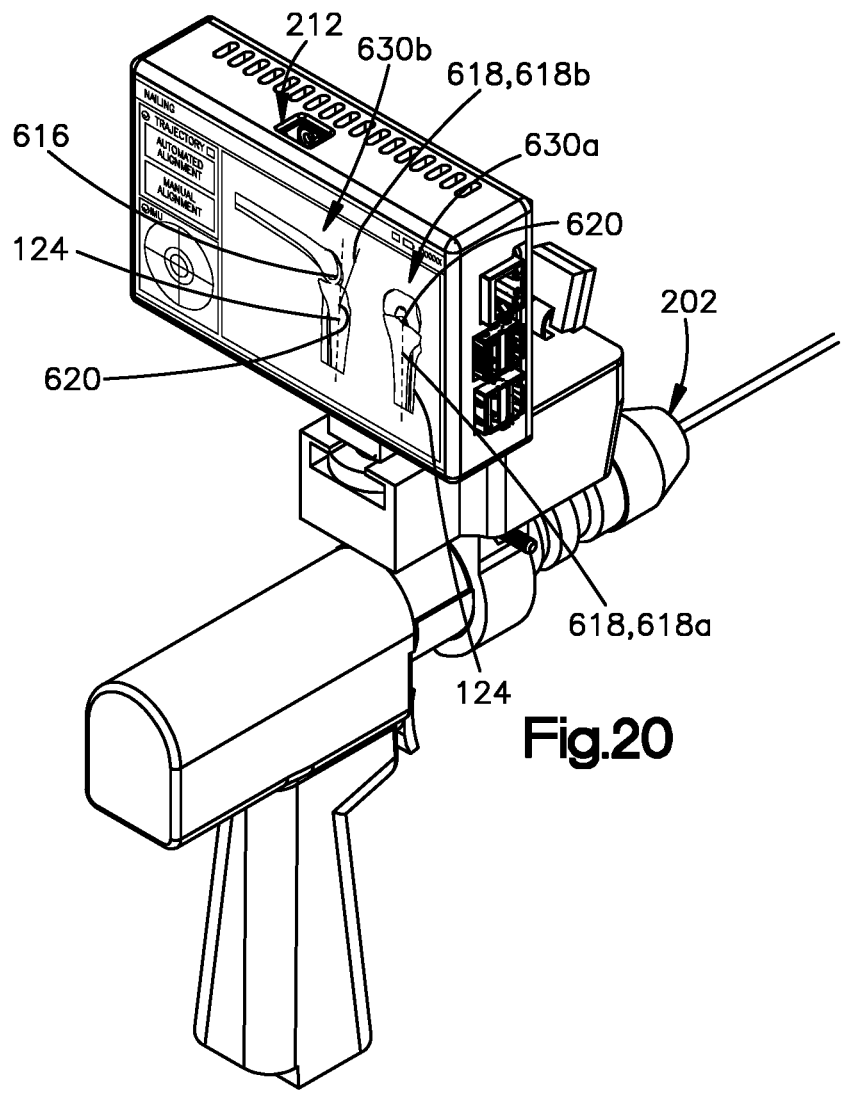
FIG. 20 is a perspective view of the surgical instrument assembly shown in FIG. 1, showing first and second representations of the anatomical structure displayed on the display, wherein a first representation of the desired trajectory overlays the first representation of the anatomical structure, and a second representation of the desired trajectory overlays the second representation of the anatomical structure.
Figure 21A:
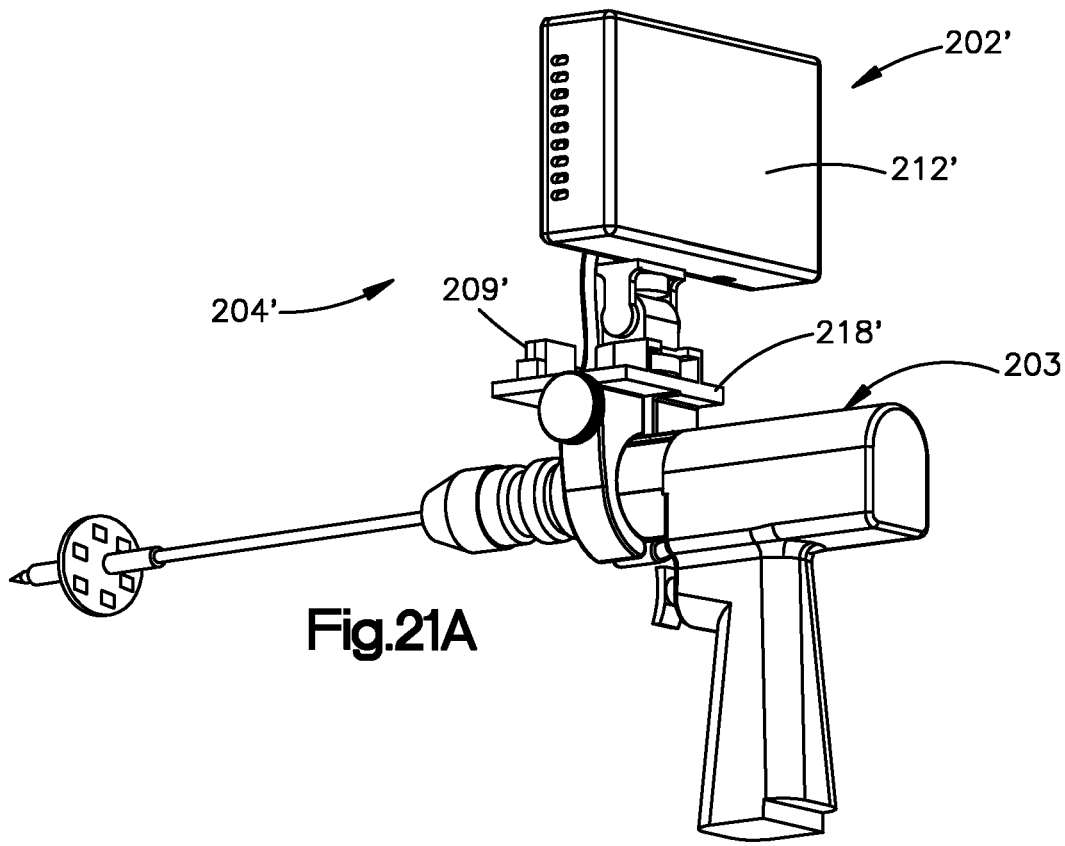
FIG. 21A is a rear perspective view of another embodiment of the surgical instrument assembly, which does not include a measuring device.
Figure 21B:
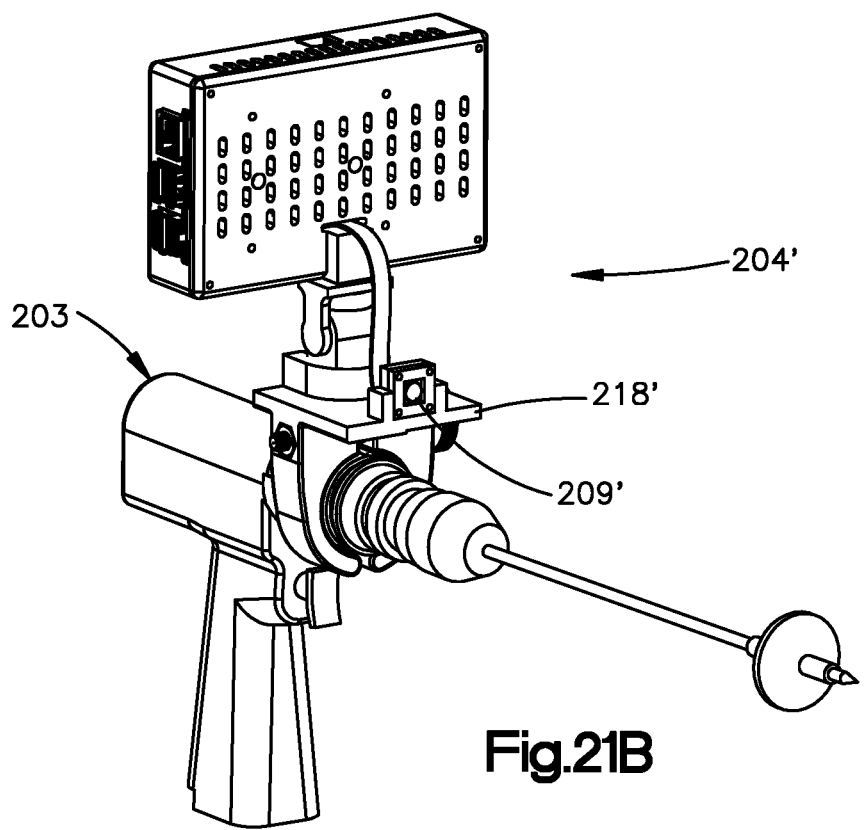
FIG. 21B is a front perspective view of the surgical instrument assembly of in FIG. 21A.
Figure 21C:
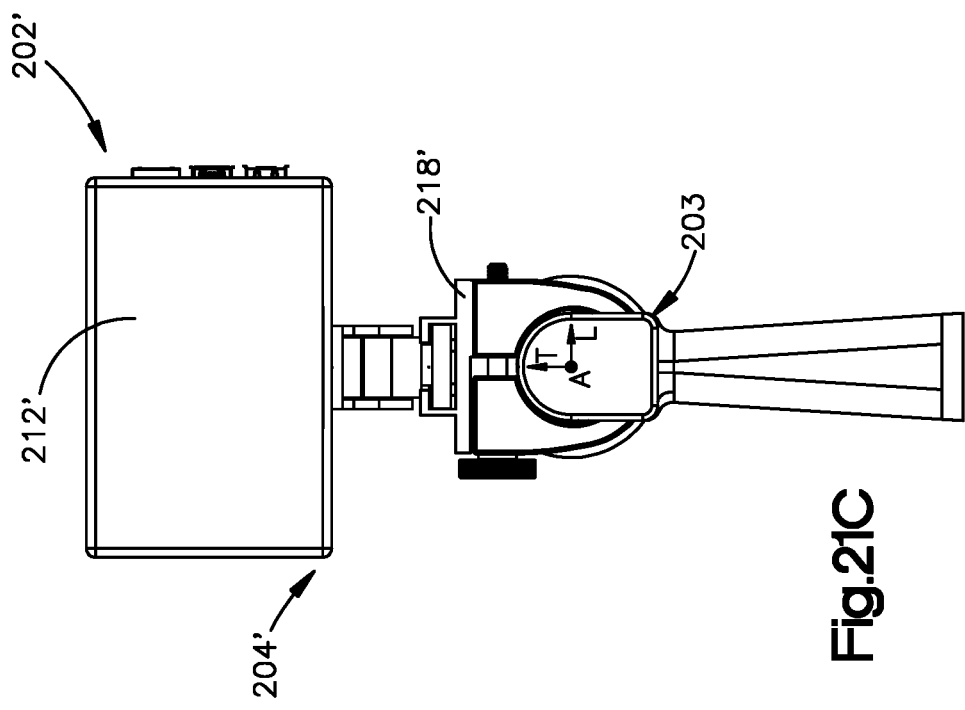
FIG. 21C is a rear elevation view of the surgical instrument assembly of FIG. 21B.
Figure 21D:
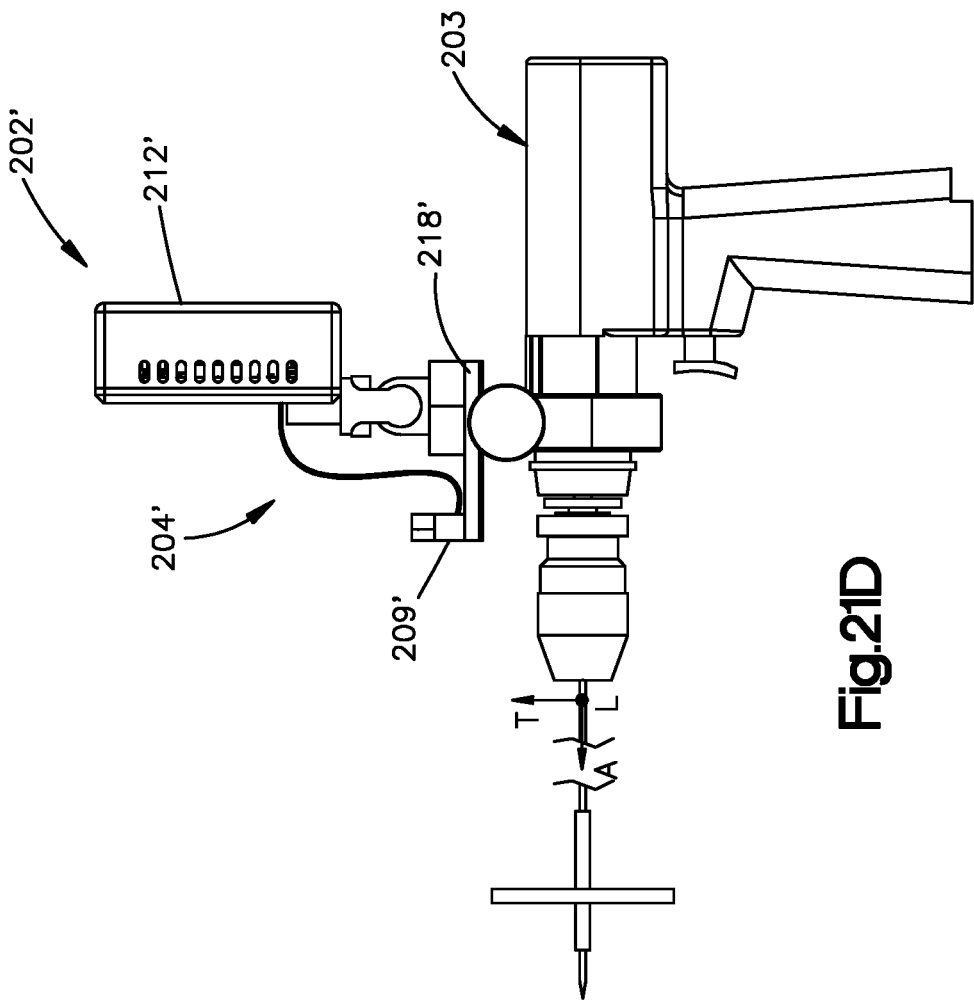
FIG. 21D is a side elevation view of the surgical instrument assembly of FIG. 21C.

Referring to FIG. 19, a given user can retrieve technique information from the surgical instrument assembly actuating a user selection via the user interface 216. For example, the user selection can cause the display 212 to display technique information 650a and 650b. The technique information 650a can include a graphical depiction of an appropriate trajectory 652a from an AP view. The technique information 650b can include a graphical depiction of an appropriate trajectory 652b from a lateral view. The technique information that can be displayed can include instructions 654 in text for placing an IM nail, among other operations. In an example, responsive to a user selection, the user interface 216 can render audible instructions associated with IM nailing operations, among others.

In some cases, a given user, for instance a medical profession, can utilize the technique information rendered by the surgical instrument assembly 202 to manually overlay the representation of the trajectory 618 on a representation image. For example, the user can actuate the manual alignment option 646, for instance by touch or the like. When the manual alignment option 646 is actuated, the user can manually overlay the representation of the trajectory 618, such that the display 212 displays the trajectory 618 on the representation image. The representation of the trajectory 618 can define a solid line, a dashed line, or the like. In an example, the user can actuate the manual alignment option 646 to adjust the axis 616 that is determined by the processor of the surgical instrument assembly 202 after the automated alignment option 622 is selected. The surgical instrument assembly 202 can adjust or determine at least a portion, for instance all, of the representation of the trajectory in response to the user actuating at least one of the options of the user interface 216. Thus, the processor of the surgical instrument assembly 202 can adjust the representation of the trajectory so as to define a new representation of the trajectory, and the display 212 can overlay the new representation of the new trajectory on the representation image of the anatomical structure, so as to display the new representation of the new trajectory. In an example, the processor can adjust the representation of the trajectory in response to the user actuating at least one of the options of the user interface 216.

In some embodiments, the processing unit determines the world coordinates of the representation of the trajectory, as discussed above with respect to the desired trajectory. The processing unit may also determine a pose of the cutting instrument relative to the representation of the trajectory based on real time image sensor data, as discussed above with respect to the desired trajectory.

Referring to FIG. 14B, by viewing the representation of the trajectory 618 and the cutting instrument 226 that is viewable on the X-ray image 602, a user can move the cutting instrument 226 to align with the representation of the trajectory, as shown in the representation image 604 of FIG. 15. In an embodiment, when the cutting instrument 226 is aligned with the representation of the trajectory 618, the processing unit 206 may instruct the display 212 to display different representation images 606 or 608, which may represent a viewpoint of the anatomical structure 124 different from that of the representation images 602 and 604. For example, the representation images 606 or 608 may represent a viewpoint that is perpendicular to the first or AP view shown in FIGS. 14B and 15.

Referring to FIGS. 14B, 15, and 20, the representation of the trajectory 618 can be referred to as a first representation 618a of the trajectory from a first perspective, for instance from an AP perspective. In an example, referring to FIGS. 16, 17 and 20, the surgical instrument assembly 202 can determine a second representation 618b of the trajectory that defines the point of entry 620 into the anatomical structure 124. The second representation 618b can be from a second perspective. By way of example, the second perspective can be approximately periocular to the first perspective, such that that first perspective can define an AP view, and the second perspective can define a lateral view. The second representation 618b of the trajectory can be determined and displayed in accordance with any of the embodiments described herein for determining and displaying the representation of the trajectory 618.

Referring to FIGS. 14B-18, the display 212 can display a position of the cutting tip 226a relative to the point of entry 620 of the anatomical structure. By viewing the second representation 618b of the trajectory and the cutting instrument 226 that is viewable on the representation images 606 and 608, a user can move the cutting instrument 226, and thus the cutting tip 226a, to align with the second representation 618 of the trajectory. Alternatively, in an automated scenario, the cutting instrument 226 can be moved automatically so as to align with the second representation 618b of the trajectory.

In some cases, when the cutting instrument 226, and thus the cutting tip 226a, is aligned with the first representation of the trajectory 618a and the second representation 618b of the trajectory, the drilling operation can begin, as the cutting instrument 226 is aligned with the appropriate point of entry and trajectory, which can be determined from the technique information described herein. The display 212 can be positioned so as to provide a line of sight to both the tip 226a and the display 212 from a location proximate of the surgical instrument 203, such that a medical professional can view both the representation images, and thus the tip 226a, and the anatomical structure 124, so as to center the tip 226a at the point of entry 620.

Referring now to FIG. 18, the display 212 can also be configured to provide a visual indication, for instance the orientation image 129, of an alignment of the cutting instrument 226 with respect to the first representation 618a of the trajectory and the second representation 618b of the trajectory. The visual indication of alignment, for instance the orientation image 129, can be based on the image sensor data representing a relative orientation of the cutting instrument 226 relative to the trajectory.

For example, referring to FIG. 18, the orientation image 129 can include the static region 130 and the movable indicator 132. The movable indicator 132 can be representative of the orientation of the cutting instrument 226. In an example, the cutting instrument 226 is oriented with the first and second representations of the trajectory 618a and 618b when the movable indicator 132 has a predetermined spatial relationship to the static region 130. In an example, a hole is drilled in the anatomical structure 124 while the cutting instrument 226 (e.g., drill bit) is aligned with first and second representations of the trajectory, and the movable indicator 132 has the predetermined spatial relationship to the static region 130. It will be understood that the predetermined spatial relationship can vary as desired. In some cases, for example, the cutting instrument 226 is oriented with the first and second representations of the trajectory when the movable indicator 132 overlies the static region 130. In some cases, the cutting instrument 226 is oriented with the first and second representations of the trajectory when the movable indicator 132 is within a boundary defined by the static region 130.

Referring now to FIGS. 10A-12, the display 212 can also be configured to provide a visual indication, for instance a depth gauge image 262, of the depth of the cutting tip 226a with respect to one or more portions of the anatomical structure 124. The processing unit 206 may determine the depth of the cutting tip 226a in real time based on the real time image sensor data. For example, the processor may determine the pose of the fiducial markers 213a relative to the one or more portions of the anatomical structure 124 in a similar manner as discussed above, based upon the X-ray image data. The processor may determine the real time position of the cutting tip 226a relative to the fiducial markers 213a based upon the real time image sensor data, and thereby determine the position of the cutting tip 226a relative to the one or more portions of the anatomical structure 124.

Figure 9:
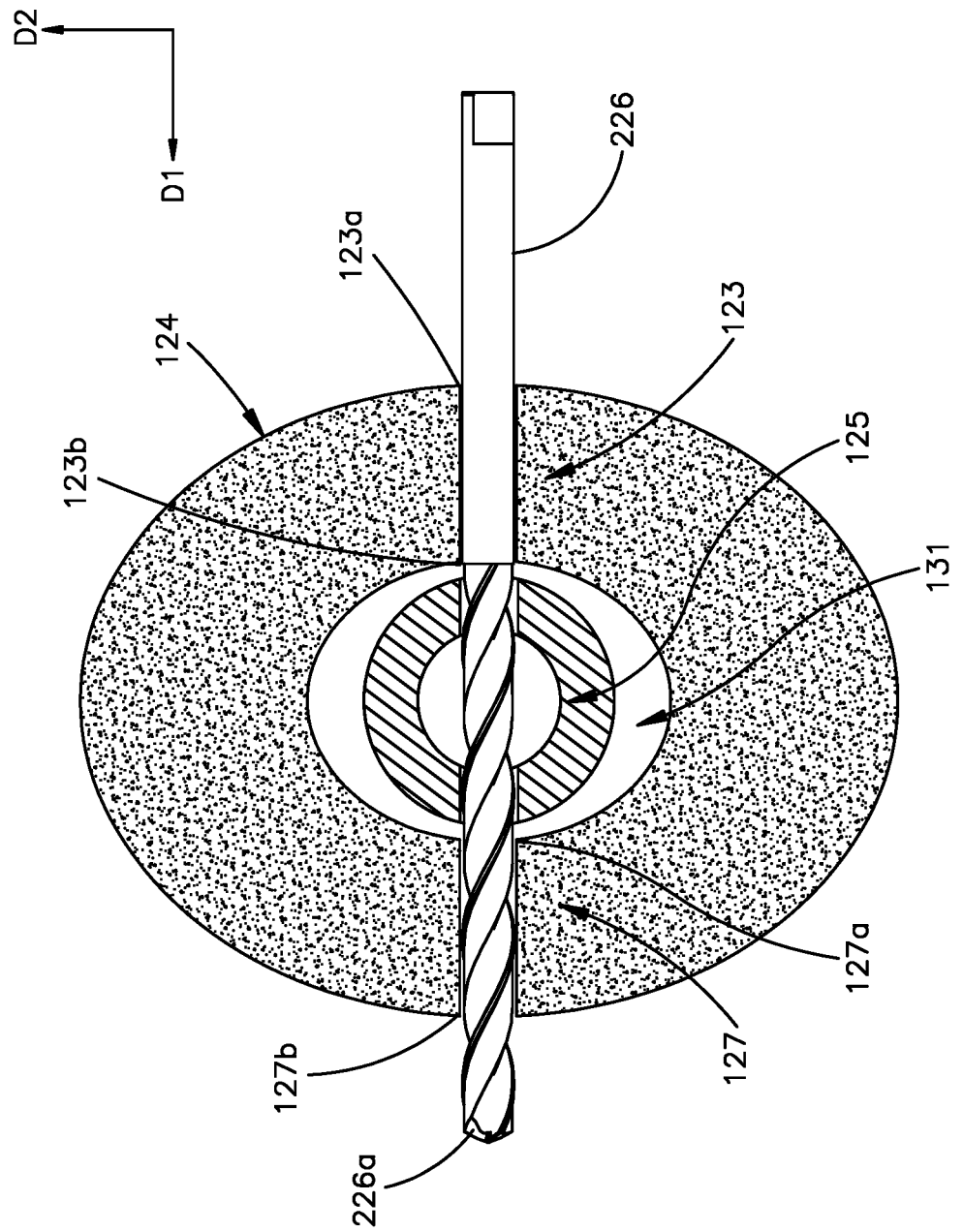
FIG. 9 is a cross section of the anatomical structure and implant, wherein the cutting instrument has traveled through the anatomical structure along a drilling direction.

In an example, referring to FIG. 9, the anatomical structure 124 may define a first or near cortex 123 and a second or far cortex 127 opposite the first cortex 123 along a first direction D1, which can be in the direction of drilling (and the desired trajectory). The first cortex 123 can define a first or near surface 123a and a second or far surface 123b opposite the first surface 123a along the first direction D1. Similarly, the second cortex 127 can define a first or near surface 127a and a second or far surface 127b opposite the first surface 127a along the first direction D1, which can also be along direction of drilling and the desired trajectory. The anatomical structure 124 can define a hollow portion 131. For example, the hollow portion 131 can be defined between the second surface 123b of the first cortex 123 and the first surface 127b of the second cortex 127.

The implant 125 may be disposed in the hollow portion 131. The target hole 126 of the implant 125 may be aligned with the cutting instrument 226 and the desired trajectory. In an embodiment, the processor determines and instructs the display to display a representation of the depth of the cutting tip with respect to one or more portions of the implant, based on the real time image sensor data.

The visual indication of depth, for instance the depth gauge image 262, can change as the cutting instrument 226, in particular the cutting tip 226a, travels into the anatomical structure 124 and/or the implant 125. In particular, the depth gauge image 262 can include data that can change when the cutting instrument tip 226a contacts the respective first and second surfaces of the first cortex 123 and the second cortex 127.

In an embodiment, the depth measurement may be done using a reflector plate system with the distance sensor, as discussed above. In some embodiments, the processing unit may track fiducial markers on the reflector plate to determine an acceleration that takes place as the cutting instrument drills through the two cortices. The processing unit may determine a length of bone drilled through based on the acceleration. In some embodiments, the distance sensor may be used in conjunction with the processor determining the acceleration to give redundant measurements. In an embodiment, the distance sensor may not be provided, and instead the processor determining the acceleration may be used for depth measurement.

Figure 10A:
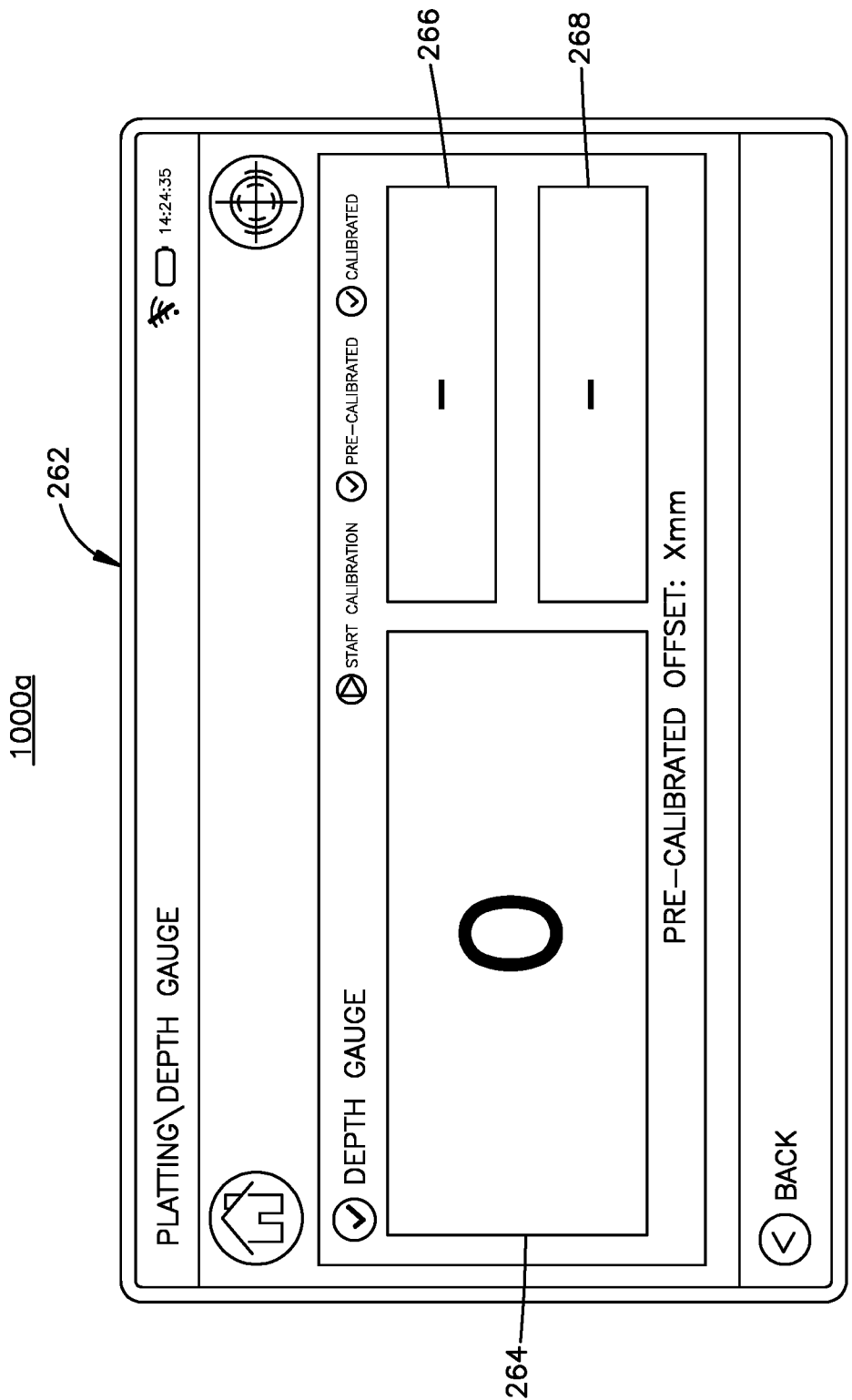
FIGS. 10A and 10B are example screen shots of the display of the surgical instrument assembly, showing visual indications of the depth of the tip of the cutting instrument with respect to portions of the anatomical structure.
Figure 12:
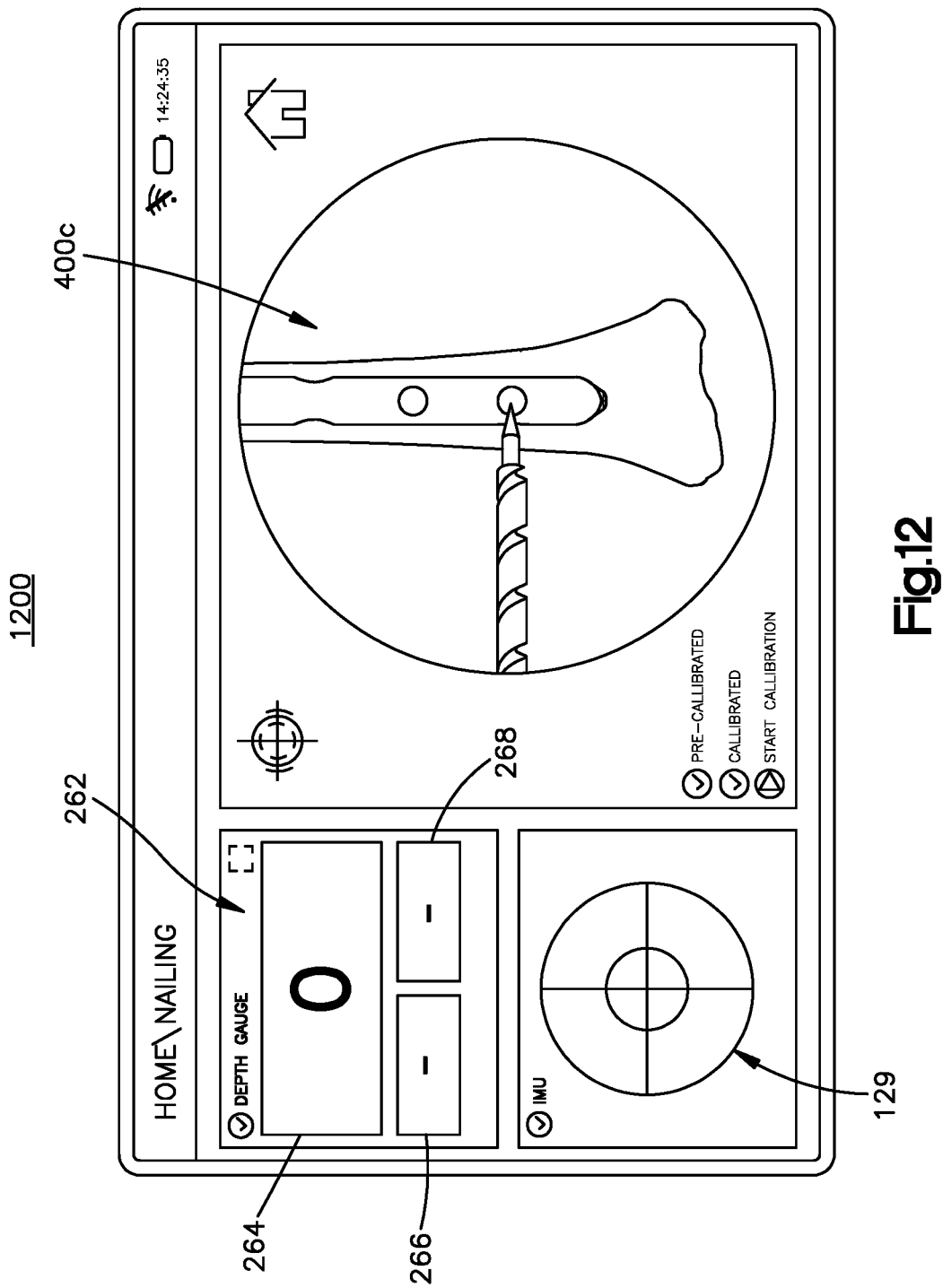
FIG. 12 is another screen shot of the display of the surgical instrument assembly, showing, at the same time: the visual indication of the alignment of the cutting instrument; the visual indication of the depth of the tip of the cutting instrument; and the cutting instrument in an X-ray image of the anatomical structure.
Figure 13:
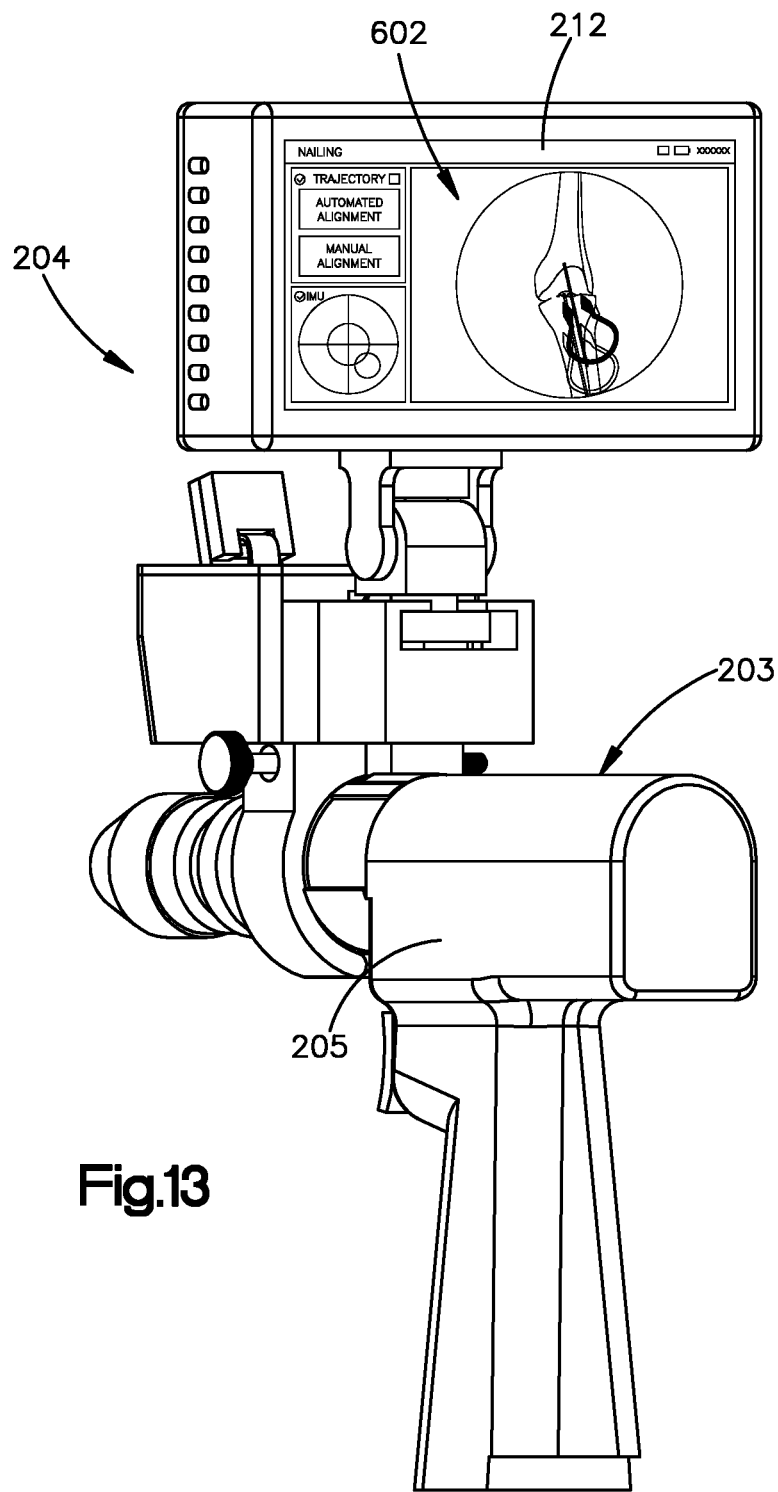
FIG. 13 is a perspective view of the surgical instrument assembly shown in FIG. 1, showing an example representation of the alignment of the cutting instrument relative to the desired trajectory, and showing an example representation of the cutting instrument relative to the patient's anatomy.

In an example operation, referring first to FIGS. 10A and 12, which depict an example depth gauge screen 1000a and an example split screen 1200, respectively, the depth gauge image 262 may be configured to measure a first distance of a reference location relative to a portion of the anatomical structure 124, and the display 212 may be configured to indicate a second distance of the cutting tip 226a relative to the portion of the anatomical structure 124. The processor may determine the depth based on the first distance as the surgical instrument 203 drills a hole. The display 212 can be configured to indicate the second distance as the surgical instrument drills a hole, so as to indicate the second distance in real-time. The first cortex 123 can define the portion of the anatomical structure 124. In an example, the first cortex 123, in particular the first surface 123a of the first cortex 123, may define the reference location from which the distance from the reference location is determined (e.g., with a distance sensor and/or based on X-ray image data and/or the image sensor data). In an example, the cutting tip defines the reference location, such that the first distance is equal to the second distance.

The display 212 can display the depth gauge screen 1000a and the example split screen 1000. In the illustrated examples, the total drill depth indication 264 indicates zero (0) when the cutting instrument tip 226a abuts the first surface 123a of the first cortex 123. In an embodiment, the processing unit may be configured such that the total drill depth indication 264 indicates zero (0) when a drill sleeve abuts the first surface 123a of the first cortex 123.

Figure 10B:
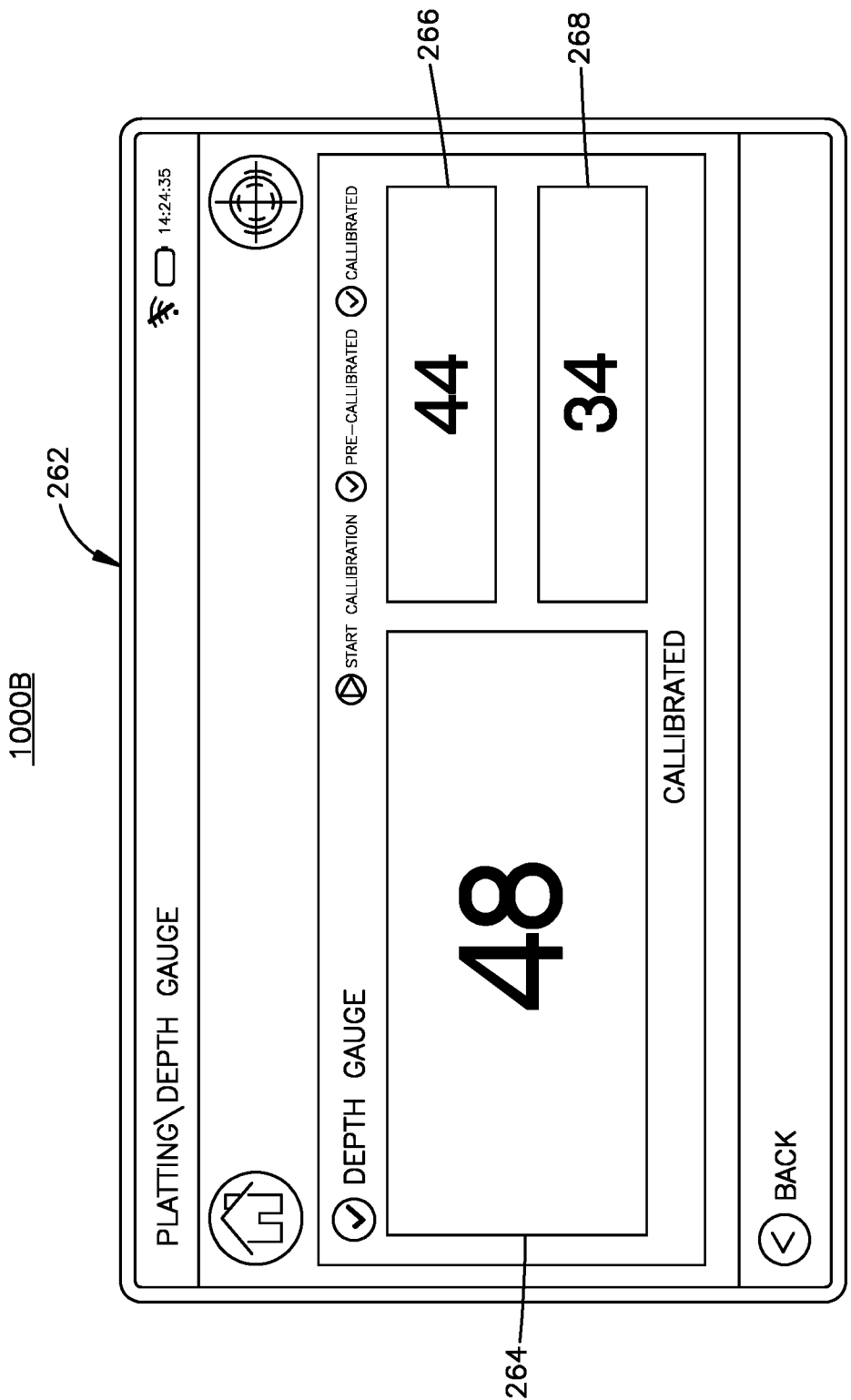
Figure 11:
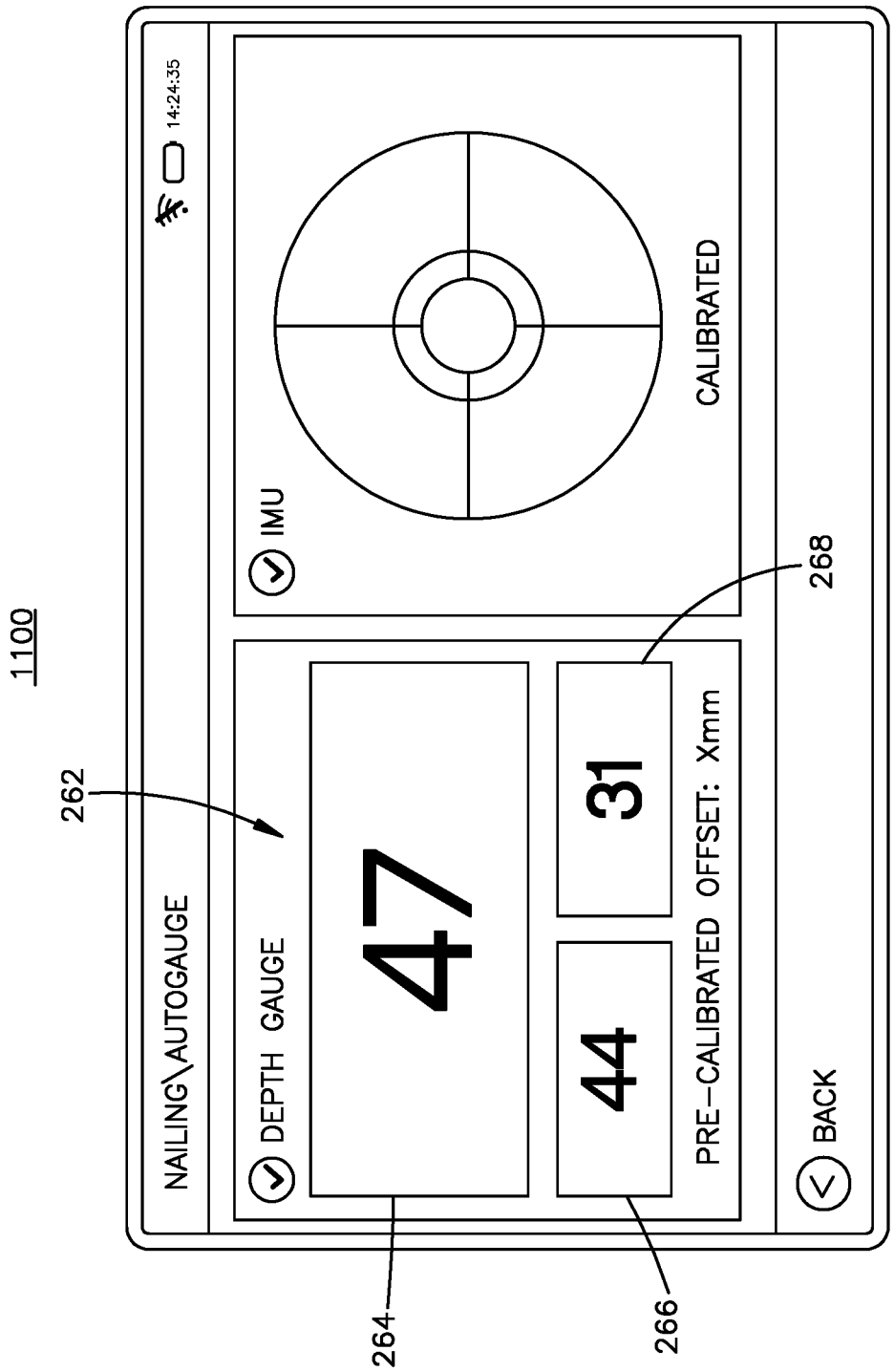
FIG. 11 is an example split screen shot of the display of the surgical instrument assembly, showing, at the same time, the visual indication of the alignment of the cutting instrument and the visual indication of the depth of the tip of the cutting instrument.

The surgical instrument 203 can be configured to drill a hole in the first direction D1 from the first cortex 123 to toward the second cortex 127. Thus, the total drill depth indication 264 can indicate zero (0) before a drilling operation, whereby the cutting instrument tip 226a enters the anatomical structure 124 during the drilling operation. Referring also to FIGS. 10B and 11, which depict an example depth gauge screen 1000b and an example split screen 1100, respectively, as the drilling operation proceeds and the cutting instrument tip 226a travels through the first cortex 123, the total drill depth indication 264 can increase so as to indicate the real-time distance that the cutting instrument tip 226a has traveled with respect to the first surface 123a of the first cortex 123. As shown, the indications of the depth gauge image 262 are rendered in millimeters, though it will be understood that the indications may be rendered in any alternative units.

The depth gauge image 262 can further include a recent cortex exit point indication 266 that indicates the distance from the cutting instrument tip 226a to the far surface of the cortex that was most recently drilled. Thus, the display 212 can be configured to indicate a third distance when the cutting tip 226a exits the first cortex 123, wherein the third distance can represent a width of the first cortex 123 along the first direction D1. As an example, when the cutting instrument tip 226a travels along the first direction D1, which can be the desired trajectory, so as to exit the second surface 123b of the first cortex 123, the recent cortex exit point indication 266 indicates the distance from the first surface 123a of the first cortex 123 to the second surface 123b of the first cortex 123. Thus, in an example, at the moment that the cutting instrument tip 226a travels through the second surface 123b of the first cortex 123, the recent cortex exit point indication 266 can indicate the same value as the total drill depth indication 264.

As drilling is performed, the processor may smooth the image sensor data to minimize errors in the navigational guidance caused by vibration, noise, or drill bit deflection. For example, the processor may determine the cutting instrument 226a pose as a rolling average. In an embodiment, the display may minimize the alignment information shown during drilling. The processor may alert the user when the cutting instrument is out of tolerance, even when the alignment information is minimized. In some embodiments, the tolerance is determined based on the typical vibration, noise, and/or drill bit deflection seen during drilling.

In some embodiments, the display only displays alignment guidance prior to drilling. For example, the display may not display alignment or other navigation guidance feedback while drilling occurs.

When the cutting instrument tip 226a travels along the first direction D1 so as to exit the second surface 127b of the second cortex 127, the recent cortex exit point indication 266 may display the distance from the first surface 123a of the first cortex 123 to the second surface 127b of the second cortex 127. Thus, the display 212 may be configured to indicate a fourth distance when the cutting tip 226a exits the second cortex 127, and the fourth distance can represent a bone width of the bone along the first direction D1. The display 212 can be configured to indicate the second distance, the third distance, and the fourth distance at the same time. Further, at the moment that the cutting instrument tip 226a travels through the second surface 127b of the second cortex 127, the recent cortex exit point indication 266 can indicate the same value as the total drill depth indication 264. The depth gauge image 262 can further include a previous cortex exit point indication 268 that displays an indication or value associated with the previous, but not most recent, cortex exit point.

Thus, continuing with the example, when the cutting instrument tip 226a exits the second surface 127b of the second cortex 127, the previous cortex exit point 268 may display the distance from the first surface 123a of the first cortex 123 to the second surface 123b of the first cortex 123. Thus, the value displayed in the recent cortex exit point indication 266 may be moved to the previous cortex exit point indication 268. As the cutting instrument tip 226a travels away from the second surface 127b of the second cortex 127, the total drill depth indication 264 can increase so as to indicate the real-time distance that the cutting instrument tip 226a has traveled with respect to the first surface 123a of the first cortex 123, as exemplified by FIGS. 10B and 11.

The user can view the depth gauge image 262 while the surgical instrument 203 operates, either under user control or autonomously, so as to better perform a drilling operation. For example, the user can view the total drill depth indication 264 while performing a drilling operation, so as to control the surgical instrument based on the total drill depth indication 264. The surgical instrument 203 can be controlled based on the information in the depth gauge image 262 so that the cutting instrument 203 does not enter unwanted portions of the anatomy, such as soft tissue or a far cortex that is not intended to be drilled, either wholly or in part. In some cases, a user can view the depth gauge image 262, in particular the total drill depth indication 264 or the recent cortex exit point indication 266, to match the length of a screw with respective holes that are drilled, instead of having to measure the holes after the drilling operation is performed. In an example, the computing device 204 stores an inventory of available screws, such that a screw is automatically matched to a hole that is drilled, based on the depth of the hole in the anatomical structure 124. In an example, a user can actuate a select screw option on the user interface 216, so that a screw is selected that corresponds to one of the indications on the depth gauge image 262, for instance the recent cortex exit point indication 266 or the total drill depth indication 262.

Thus, in operation, the display 212 can receive and display a plurality of representation images of the anatomical structure in real-time, based on the real time image sensor data. The display 212 can display the orientation image 129 and the depth gauge image 262, in particular the total drill depth indication 262, as the surgical instrument 203 is operated. For example, the depth gauge image 262 can be representative of distances that the cutting instrument 203 as moved. In an embodiment, the representation images, the orientation images, and the depth gauge images are displayed by the display at the same time. As the cutting instrument 203 moves along a drilling direction, the distance displayed by the display may change, so as to update the distance in real-time (e.g., based on the real time image sensor data).

Figure 6A:
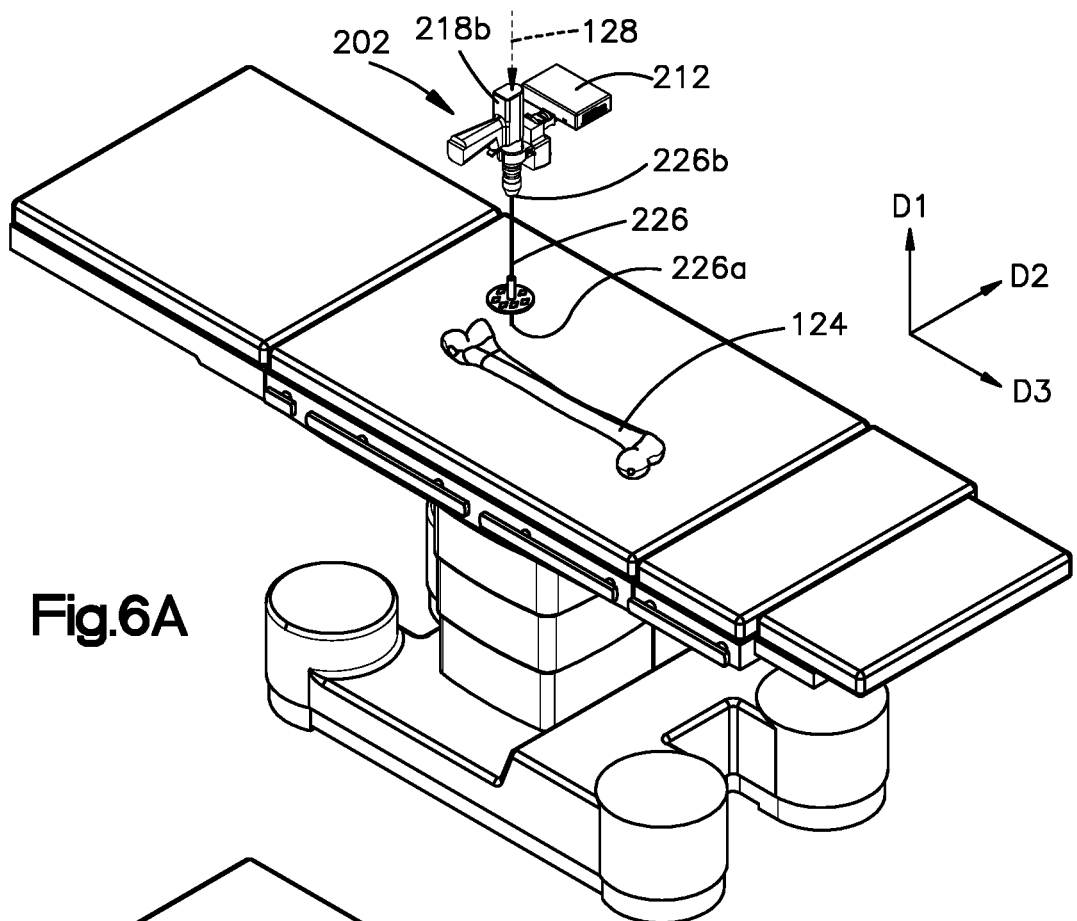
FIG. 6A depicts the example imaging system shown in FIG. 1, showing an example anatomical structure and an example orientation of the surgical instrument assembly.
Figure 6B:
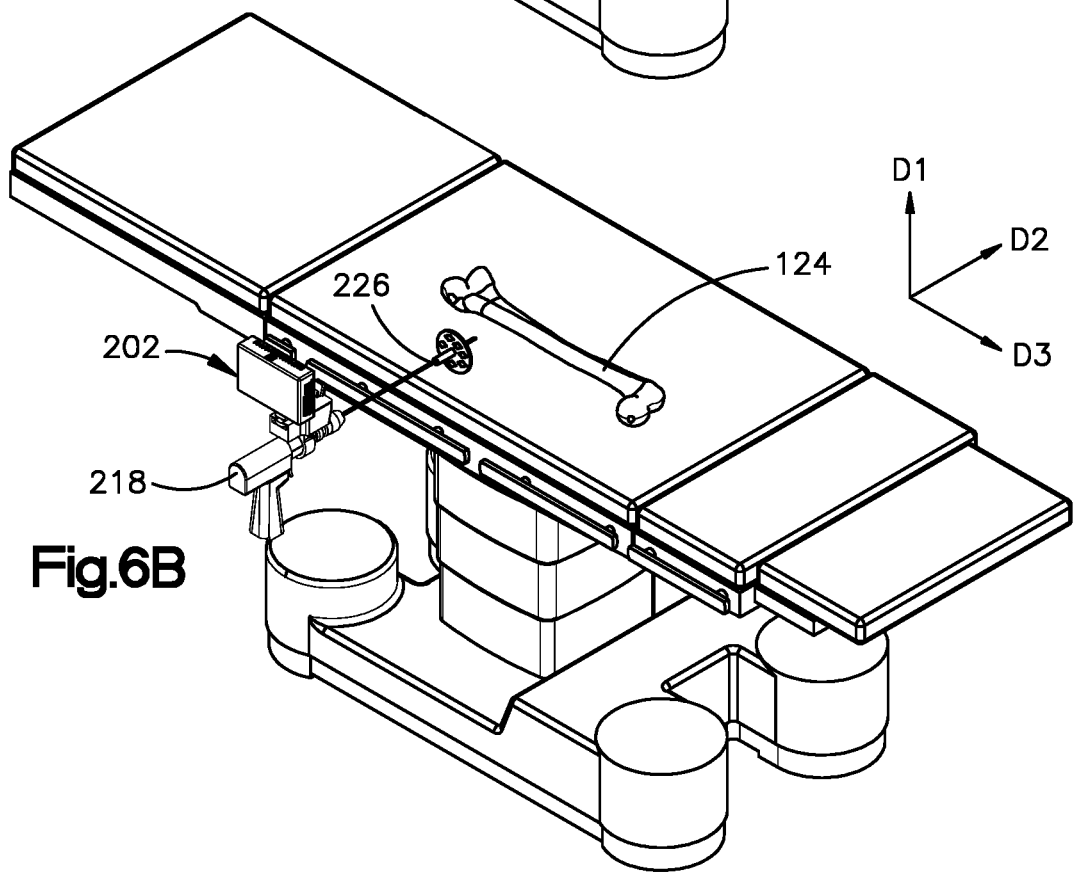
FIG. 6B depicts another example orientation of the surgical instrument assembly in the imaging system shown in FIG. 6A.

In an example, referring to FIG. 6A, the surgical instrument 203 can be operated along the first direction D1 that is parallel to the desired trajectory, so as to drill a hole along the first direction D1. During drilling, for example, as the orientation of the cutting instrument 226 moves away from the zero value, the movable indicator 132 can move away from the static region 130. The movable indicator 132 can move relative to the static region 130 at the same time that the orientation of the cutting instrument 226 moves relative to the zero value, such that the movable indicator 132 provides a real-time representation of the orientation of the cutting instrument 226. For example, as the proximal end 226b of the cutting instrument 226 moves along a second direction D2 relative to the cutting tip 226a of the cutting instrument 226, the movable indicator 132 can move along the second direction D2 (e.g., see FIG. 5A). The second direction D2 can be perpendicular to the first direction D1. Similarly, as the proximal end 226b of the cutting instrument 226 moves along a third direction D3 relative to the cutting tip 226a of the cutting instrument 226, the movable indicator 132 can move along the third direction D3 (e.g., see FIG. 5B). The third direction D3 can be perpendicular to both the first and second directions D1 and D2, respectively. Further, it will be understood that as the proximal end 226b of the cutting instrument 226 moves along both the second and third directions relative to the cutting tip 226a of the cutting instrument 226, the movable indicator 132 can move along both the second and third directions D3. Further, the orientation screens 500a-500c can include a numerical representation 136 of the orientation of the cutting instrument 226 along the second and third directions D2 and D3.

Referring in particular to FIG. 5C, when the cutting instrument 226 is oriented in accordance with the zero value, the movable indicator 132 can be positioned within a boundary defined by the static region 130. Further, in some cases, when the cutting instrument 226 is precisely aligned with the desired trajectory, the numerical representation 136 may indicate that zero values associated with both the second and third directions. By way of an IM nailing example, a medical professional can maintain the orientation image 129 illustrated in FIG. 5C while drilling, so as to drill holes having the appropriate orientation at the target locations 126.

The above processes may be repeated to select or determine a new desired trajectory to drill a new hole. For example, the C-arm may generate a new X-ray image including a new target portion of an implant or anatomy and the fiducials 213a fixed relative to the new target portion. A new desired trajectory may be determined relative to the fiducials 213a and oriented in a world coordinate system based on the new X-ray image data of the new X-ray image. The pose of the cutting instrument 226 relative to the new desired trajectory may be determined based on the real time image sensor data. In an embodiment, the original X-ray image data shows a sufficient amount of the new target portion, and thus the pose of the cutting instrument 226 relative to the new desired trajectory may be determined without the new X-ray image. For example, the user may select the new target portion on the display and set the new desired trajectory without the new X-ray image data.

After drilling is completed, a final X-ray image may be taken of the target portion (or portions) to confirm that the distal locking, for example, completed as desired. In an embodiment, fluoroscopic video of the target portion is taken to confirm completion as desired by the user.

Referring now to FIGS. 21A-21D, a second embodiment of the surgical instrument assembly is shown. It is to be appreciated that the second embodiment can be similar to the first embodiment of the surgical instrument assembly shown in FIGS. 1-2D. Accordingly, the same reference numbers used above with reference to the first embodiment can be also used with a "prime" notation in reference to a second embodiment. It is also to be appreciated that, unless otherwise set forth below, the components (and features thereof) of the surgical instrument assembly 202' of the second embodiment can be similar to those of the first embodiment.

The surgical instrument assembly 202' may include the surgical instrument 203, a computing device 204', an image sensor 209', and an attachment member 218' configured to attach the image sensor 209' to the surgical instrument 203. The computing device 204' may not include a measuring device (e.g., the measuring device 211 described above).

The image sensor 209' may be attached to a top of the attachment member 218', may be attached to the surgical instrument. The image sensor 209' may be configured to face forward, away from the display 212'. For example, the image sensor 209' may face forward along the longitudinal axis A. The image sensor 209' may be rotatably attached to the attachment member 218', such that the image sensor 209' may face forward at a downward angle toward a longitudinal axis A or an upward angle away from the longitudinal axis A. In an embodiment, the image sensor 209' is fixed relative to the attachment member 218' such that the image sensor 209' is not rotatable relative to the attachment member 218'.

Any of the above processing steps may be performed by the processing unit 206 and/or stored as instructions by the memory portion 214. For example, each detecting, determining, generating, and/or outputting step discussed above may be performed by the processing unit 206 and/or stored as instructions by the memory portion 214. The memory portion 214 may be a non-transitory memory portion.

While example embodiments of devices for executing the disclosed techniques are described herein, the underlying concepts can be applied to any computing device, processor, or system capable of communicating and presenting information as described herein. The various techniques described herein can be implemented in connection with hardware or software or, where appropriate, with a combination of both. Thus, the methods and apparatuses described herein can be implemented, or certain aspects or portions thereof, can take the form of program code (i.e., instructions) embodied in tangible non-transitory storage media, such as floppy diskettes, CD-ROMs, hard drives, or any other machine-readable storage medium (computer-readable storage medium), wherein, when the program code is loaded into and executed by a machine, such as a computer, the machine becomes an apparatus for performing the techniques described herein. In the case of program code execution on programmable computers, the computing device will generally include a processor, a storage medium readable by the processor (including volatile and non-volatile memory and/or storage elements), at least one input device, and at least one output device, for instance a display. The display can be configured to display visual information. For instance, the displayed visual information can include fluoroscopic data such as X-ray images, fluoroscopic images, orientation screens, or computer-generated visual representations.

The program(s) can be implemented in assembly or machine language, if desired. The language can be a compiled or interpreted language, and combined with hardware implementations.

The techniques described herein also can be practiced via communications embodied in the form of program code that is transmitted over some transmission medium, such as over electrical wiring or cabling, through fiber optics, or via any other form of transmission. When implemented on a general-purpose processor, the program code combines with the processor to provide a unique apparatus that operates to invoke the functionality described herein. Additionally, any storage techniques used in connection with the techniques described herein can invariably be a combination of hardware and software.

Certain terminology is used in the following description for convenience only and is not limiting. The words "right", "left", "lower" and "upper" designate directions in the drawings to which reference is made. The words "inner", "internal", and "interior" refer to directions towards the geometric center of the anatomical structure and/or the implant, while the words "outer", "external", and "exterior" refer to directions away from the geometric center of the implant or the anatomical structure. The words, "anterior", "posterior", "superior," "inferior," "medial," "lateral," and related words and/or phrases are used to designate various positions and orientations in the human body to which reference is made. When these words are used in relation to the implant or the anatomical structure, they are to be understood as referring to the relative positions of the respective anatomical structure or the implant as implanted in the body as shown in FIG. 9. The terminology includes the above-listed words, derivatives thereof and words of similar import.

What is claimed:

1. A surgical instrument assembly comprising:
   a surgical instrument configured to operate on an anatomical structure, wherein the surgical instrument comprises a distal end and a proximal end spaced proximally from the distal end;
   an image sensor that is attached to the surgical instrument, wherein the image sensor is configured to detect an orientation of at least one fiducial marker relative to the image sensor, and the image sensor is configured to generate image sensor data that is based on the orientation of the at least one fiducial marker detected by the image sensor, wherein a distalmost portion of the image sensor is disposed closer to the proximal end than the distal end;
   a processor;
   a memory in communication with the processor, the memory having stored therein instructions that, upon execution of the processor, cause the processor to 1) receive X-ray image data representing the at least one fiducial marker and representation of the anatomical structure and/or an implant, 2) determine, based on the X-ray image data, a trajectory, relative to the at least one fiducial marker and relative to the anatomical structure and/or the implant, wherein the trajectory extends toward the anatomical structure and/or the implant, and 3) determine an orientation of the surgical instrument relative to the trajectory based on the image sensor data; and
   a display coupled to the processor wherein the display is configured to display a representation of the orientation of the surgical instrument relative to the trajectory.

2. The surgical instrument assembly of claim 1, wherein the display is attached to the surgical instrument.

3. The surgical instrument assembly of claim 1, wherein the instructions, upon execution of the processor, further cause the processor to calculate, based on the image sensor data, depth information representing a depth of the surgical instrument.

4. The surgical instrument assembly of claim 1, wherein the instructions, upon execution of the processor, further cause the processor to:
   determine the orientation and position of the surgical instrument relative to the trajectory based on the image sensor data; and
   generate the representation of the orientation of the surgical instrument relative to the trajectory, wherein the representation of the orientation includes a static region and a movable indicator that are based on the orientation of the surgical instrument relative to the trajectory, wherein the movable indicator moves relative to the static region as the surgical instrument moves relative to the trajectory and the at least one fiducial marker, wherein a zero value represents an alignment of the orientation of the surgical instrument with the trajectory, wherein as the orientation of the surgical instrument moves away from the zero value the movable indicator moves away from the static region, and as the orientation of the surgical instrument moves toward the zero value the movable indicator moves toward the static region.

5. The surgical instrument assembly of claim 1, wherein the trajectory defines a point of entry into the anatomical structure and into an opening of the implant, and wherein the implant is an intramedullary nail and the opening defines a distal locking hole of the intramedullary nail into the anatomical structure.

6. The surgical instrument assembly of claim 1, wherein the X-ray image data represents only a single X-ray image of the same target location.

7. The surgical instrument assembly of claim 1, further comprising an X-ray imaging device configured to detect an orientation of the at least one fiducial marker and the anatomical structure and/or the implant to generate the X-ray image data based on the orientation of the at least one fiducial marker and the anatomical structure and/or the implant.

8. The surgical instrument assembly of claim 1, further comprising the at least one fiducial marker, wherein the at least one fiducial marker is an array of ArUco markers that is detectable by an X-ray imaging device and the image sensor.

9. The surgical instrument assembly of claim 1, wherein the image sensor data represents the at least one fiducial marker, which is at least one first fiducial marker, and the image sensor data represents one or more second fiducial markers that are not represented by the X-ray image data, and wherein the instructions, upon execution of the processor, further cause the processor to determine a pose of the one or more second fiducial markers;
   wherein the image sensor data represents images taken from multiple different viewpoints; and
   wherein the instructions, upon execution of the processor, further cause the processor to daisy-chain the images to determine the pose of the one or more second fiducial markers, such that a pose of a first one of the one or more second fiducial markers is determined based on a pose of a second one of the one or more second fiducial markers.

10. The surgical instrument assembly of claim 1, wherein determining the trajectory comprises determining a pose of a distal locking hole, of an intramedullary nail, relative to the at least one fiducial marker based on the X-ray image data, wherein determining the orientation of the surgical instrument comprises determining a pose of a drill bit, of the surgical instrument, relative to the at least one fiducial marker based on the image sensor data, and wherein the instructions, upon execution of the processor, further cause the processor to display a representation of the pose of the drill bit relative to the locking hole.

11. The surgical instrument assembly of claim 1, wherein the instructions, upon execution of the processor, further cause the processor to determine an orientation of the surgical instrument relative to the trajectory based on the image sensor data, a predetermined pose of the image sensor relative to the surgical instrument, and a predetermined size and shape of the surgical instrument;

wherein the anatomical structure is a bone that includes an intramedullary canal;

wherein the surgical instrument assembly is configured to drill a hole in the bone; and wherein the representation of the trajectory further defines a line along which the hole can be drilled so as to meet the intramedullary canal.

12. The surgical instrument assembly of claim 1, wherein the display is configured to display the representation of the orientation of the surgical instrument relative to the trajectory in real time based upon the image sensor data, which is generated by the image sensor in real time.

13. The surgical instrument assembly of claim 12, wherein the instructions, upon execution of the processor, further cause the processor to 1) determine a world coordinate system that is fixed relative to the at least one fiducial marker, based on the X-ray image data, 2) determine an image sensor coordinate system that is fixed relative to the image sensor, and 3) determine, based on the image sensor data, a real time transformation matrix between the image sensor coordinate system and the world coordinate system, such that the orientation of the surgical instrument relative to the trajectory is determined in real time based on the image sensor data and the real time transformation matrix.

14. The surgical instrument assembly of claim 1, wherein the surgical instrument further includes a cutting instrument that includes a distal cutting tip, and wherein the image sensor is configured to face toward the distal cutting tip and away from the display.

15. The surgical instrument assembly of claim 14, wherein the image sensor has a predetermined orientation relative to the cutting instrument of the surgical instrument, and wherein the memory has stored therein the predetermined orientation of the image sensor; or wherein the image sensor is configured to detect an orientation and/or position of a plate carried by the cutting instrument.

16. A method of displaying an orientation of a surgical instrument that comprises a distal end and a proximal end spaced proximally from the distal end, the method comprising:

receiving an X-ray image data representing at least one fiducial marker and representing an anatomical structure and/or an implant;

determining, based on the X-ray image data, a trajectory, relative to the at least one fiducial marker, that extends toward the anatomical structure and/or the implant;

generating image sensor data, with an image sensor, that is based on an orientation of the at least one fiducial marker relative to the image sensor, wherein a distal-most portion of the image sensor is disposed closer to the proximal end than the distal end;

determining an orientation of the surgical instrument relative to the trajectory based upon the image sensor data; and displaying, with a display, a representation of the orientation of the surgical instrument relative to the trajectory.

17. The method of any one of claim 16, wherein the display displays the representation of the orientation of the surgical instrument relative to the trajectory in real time based upon the image sensor data, which is generated by the image sensor in real time.

18. The method of any one of claim 16, further comprising detecting, with the image sensor, an orientation of the at least one fiducial marker relative to the image sensor.

19. The method of any one of claim 16, wherein the image sensor data represents the at least one fiducial marker, which is at least one first fiducial marker, and the image sensor data represents one or more second fiducial markers that are not represented by the X-ray image data, and wherein the image sensor data represents images taken from multiple different viewpoints; and wherein the method further comprises determining a pose of the one or more second fiducial markers, and daisy-chaining the images to determine the pose of the one or more second fiducial markers, such that a pose of a first one of the one or more second fiducial markers is determined based on a pose of a second one of the one or more second fiducial markers.

20. The method of any one of claim 16, wherein determining the trajectory comprises determining a pose of a distal locking hole, of an intramedullary nail, relative to the at least one fiducial marker based on the X-ray image data;

wherein determining the orientation of the surgical instrument comprises determining a pose of a drill bit, of the surgical instrument, relative to the at least one fiducial marker based on the image sensor data; and wherein displaying the representation of the orientation comprises displaying a representation of the pose of the drill bit relative to the locking hole.

* * * * *